(12) United States Patent
Langlade Demoyen et al.

(10) Patent No.: US 10,138,488 B2
(45) Date of Patent: *Nov. 27, 2018

(54) CANCER VACCINE FOR DOGS

(71) Applicant: INVECTYS, Paris (FR)

(72) Inventors: Pierre Langlade Demoyen, Neuilly-sur-Seine (FR); Simon Wain-Hobson, Montigny-le-Bretonneux (FR); Christelle Liard, Chatillon (FR)

(73) Assignee: INVECTYS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,652

(22) PCT Filed: Mar. 28, 2014

(86) PCT No.: PCT/EP2014/056381
§ 371 (c)(1),
(2) Date: Sep. 28, 2015

(87) PCT Pub. No.: WO2014/154905
PCT Pub. Date: Oct. 2, 2014

(65) Prior Publication Data
US 2016/0046950 A1 Feb. 18, 2016

(30) Foreign Application Priority Data
Mar. 28, 2013 (EP) .................... 13305405

(51) Int. Cl.
| *C12N 15/52* | (2006.01) |
| *C12N 9/12* | (2006.01) |
| *A61K 39/00* | (2006.01) |
| *A61K 38/00* | (2006.01) |

(52) U.S. Cl.
CPC .......... *C12N 15/52* (2013.01); *A61K 39/0011* (2013.01); *C12N 9/1276* (2013.01); *A61K 38/00* (2013.01); *A61K 2039/53* (2013.01); *A61K 2039/552* (2013.01); *C12Y 207/07049* (2013.01)

(58) Field of Classification Search
None
See application file for complete search history.

(56) References Cited

U.S. PATENT DOCUMENTS

| 5,539,084 | A | 7/1996 | Geysen et al. |
| 5,840,839 | A | 11/1998 | Wang et al. |
| 8,003,773 | B2 | 8/2011 | Langlade-Demoyen et al. |
| 8,222,392 | B2 | 7/2012 | Cech et al. |
| 2003/0143228 | A1 | 7/2003 | Chen et al. |
| 2004/0106128 | A1* | 6/2004 | Majumdar ........... C12N 9/1276 435/6.18 |
| 2008/0090778 | A1 | 4/2008 | Scarselli et al. |
| 2009/0175892 | A1 | 7/2009 | Langlade-Demoyen et al. |
| 2009/0269739 | A1 | 10/2009 | Cech et al. |
| 2011/0318380 | A1 | 12/2011 | Brix et al. |
| 2016/0051650 | A1* | 2/2016 | Langlade Demoyen ................... A61K 39/0011 424/185.1 |
| 2016/0347798 | A1 | 12/2016 | Poma et al. |

FOREIGN PATENT DOCUMENTS

| WO | 98/14593 A2 | 4/1998 |
| WO | 2003038047 A2 | 5/2003 |
| WO | 2008043760 A2 | 4/2008 |

OTHER PUBLICATIONS

Velders et al. (J. Immunology 2001 166: 5366-5373).*
Adotevi, Olivier et al. "Immunogenic HLA-B *0702-Restricted Epitopes Derived from Human Telomerase Reverse Transcriptase that Elicit Antitumor Cytotoxic T-Cell Responses" Clin Cancer Res (2006), vol. 12, No. 10, pp. 3158-3167.
Adotevi, Olivier et al., "Targeting human telomerase reverse transcriptase with recombinant lentivector is highly effective to stimulate antitumor CD8 T-cell immunity in vivo" Blood (2010), vol. 115, No. 15, pp. 3025-3032.
Artandi, Steven E. et al. "Telomeres and telomerase in cancer", Carcinogenesis (2010), vol. 31, No. 1, pp. 9-18.
Bevan, Michael J., "Helping the CD8+ T-Cell Response", Nature Reviews Immunology (2004), vol. 4, pp. 595-602.
Godet, Yann et al. "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response", Clinical Cancer Research: An Official Journal of the American Association for Cancer Research (2012), vol. 18No. 10, pp. 2943-2953.
European Search Report and Opinion dated Sep. 24, 2012, which issued during prosecution of European Application No. 12305319.1, 7 pages.
Hanahan, Douglas et al., "Hallmarks of Cancer: The Next Generation" Cell (2011), vol. 144, pp. 646-674.
International Search Report and Written Opinion of the International Searching Authority dated Apr. 12, 2013, which issued during prosecution of International Application No. PCT/EP2013/054592, 10 pages.
International Preliminary Report on Patentability Issued in International Application No. PCT/EP2013/054592 dated Sep. 16, 2014; 5 pages.
International Preliminary Report on Patentability dated Sep. 29, 2015 which issued during prosecution of International Patent Application No. PCT/EP2014/056381, 8 pages.
Kiecker, Felix et al., "Analysis of Antigen-Specific T-Cell Responses With Synthetic Peptides—What Kind of Peptide for Which Purpose?", Human Immunology (2004), vol. 65, pp. 523-536.
Klebanoff, Christopher a. et al., "Therapeutic cancer vaccines: are we there yet?", Immunology Reviews (2011), vol. 239, pp. 27-44.
ri.
Kyte, Jon Amund et al. "Telomerase Peptide Vaccination Combined with Temozolomide: A Clinical Trial in Stage IV Melanoma Patients", Clinical Cancer Research (2011), vol. 7, No. 13, pp. 4568-4580.

(Continued)

*Primary Examiner* — Peter J Reddig
(74) *Attorney, Agent, or Firm* — Troutman Sanders LLP

(57) ABSTRACT

The present invention provides an immunogenic composition comprising a nucleic acid that comprises a sequence encoding a dog telomerase deprived of telomerase catalytic activity, or a fragment thereof.

35 Claims, 19 Drawing Sheets

Specification includes a Sequence Listing.

(56) References Cited

OTHER PUBLICATIONS

Martinez, Paula et at., "Telomeric and extra-telomeric roles for telomerase and the telomere-binding proteins" Nature Reviews Cancer (2011), vol. 11, pp. 161-176.
Osen, Wolfram et al. "Screening of Human Tumor Antigens for CD4+ T Cell Epitopes by Combination of HLA-Transgenic Mice, Recombinant Adenovirus and Antigen Peptide Libraries", PLoS ONE (2010), vol. 5, Issue 11, p. e14137.
Scardino, Antonio et al., "HER-2/neu and hTERT Cryptic Epitopes as Novel Targets for Broad Spectrum Tumor Immunotherapy", The Journal of Immunology (2002), vol. 168, pp. 5900-5906.
Schlapbach, Christoph et al. "Telomerase-specific GV1001 peptide vaccination fails to induce objective tumor response in patients with cutaneous T cell lymphoma" Journal of Dermatological Science (2011), vol. 62, No. 2, pp. 75-83.
Schroers, Roland et al., "Human Telomerase Reverse Transcriptase-Specific T-Helper Responses Induced by Promiscuous Major Histocompatibility Complex Class II-Restricted Epitopes" Clinical Cancer Research: An Official Journal of the American Association for Cancer Research (2003), vol. 9, No. 13, pp. 4743-4755.
Schroers, Roland et al. "Identification of HLA DR7-restricted Epitopes from Human Telomerase Reverse Transcriptase Recognized by CD4+ T-Helper Cells" Cancer Research, American Association for Cancer Research (2002), vol. 62, No. 9. pp. 2600-2605.
Reay, Philip et al., "Use of Global Amino Replacements to Define the Requirements for MHC Binding and T Cell Recognition of Moth Cytochrome c (93-103)", Journal of Immunology (1994), vol. 152, pp. 3946-3957.
Bolonaki, Irini et al. "Vaccination of Patients with Advanced Non-Small-Cell Lung Cancer With an Optimized Cryptic Human Telomerase Reverse Transcriptase Peptide" Journal of Clinical Oncology: Official Journal of the American Society of Clinical Oncology (2007) vol. 25:19, pp. 2727-2734.
Ruden, Maria et al. "Novel anticancer therapeutics targeting telomerase" Cancer Treatment Reviews (2013), vol. 39, No. 5, pp. 444-456.
Yang, Yinhua et al. "Nucleolar Localization of hTERT Protein Is Associated with Telomerase Function" Experimental Cell Research (2002), vol. 277, No. 2, pp. 201-209.
International Search Report and Written Opinion of the International Searching Authority dated Feb. 4, 2015, which issued during prosecution of International Application No. PCT/EP2014/073164, 10 pages.
International Preliminary Report on Patentability Issued in International Application No. PCT/EP2014/073164 dated May 3, 2016, 6 pages.
European Communication Pursuant to Article 94(3) EPC dated Jan. 17, 2017; 5 pages.
International Search Report and Written Opinion of the International Searching Authority dated Jul. 2, 2014, which issued during prosecution of International Application No. PCT/EP2014/056380, 13 pages.
Peruzzi D et al: "Telomerase and HER-2/neu as targets of genetic cancer vaccines in dogs", Vaccine, 2010, vol. 28, No. 5, pp. 1201-1208.
Peruzzi D et al: "A Vaccine Targeting Telomerase Enhances Survival of Dogs Affected by B-cell Lymphoma", Molecular Therapy, 2010, vol. 18, No. 8, pp. 1559-1567.
International Search Report and Written Opinion of the International Searching Authority dated Jul. 2, 2014 which issued during prosecution of International Patent Application No. PCT/EP2014/056381.

Andersson, H. A. et al., "Maximizing Antigen Targeting to the Proteasome for Gene-Based Vaccines", Molecular Therapy (2004), vol. 10, No. 3, pp. 432-446.
Drosopoulos, W. C. et al., "The active site residue Valine 867 in human telomerase reverse transcriptase influences nucleotide incorporation and fidelity", Nucleic Acids Research (2007), vol. 35, No. 4, pp. 1155-1168.
NCBI Sequence NM_198253.2, *Homo sapiens* telomerase reverse transcriptase (TERT), transcript variant 1, mRNA, 8 pages, Oct. 27, 2012.
European Communication Pursuant to Article 94(3) EPC issued in European Pat. Appl. No. EP14790592.1 and dated May 30, 2017, 4 pages.
Wang, Qingmin et al., "Improved Cellular Immune Response Elicited by a Ubiquitin-Fused DNA Vaccine Against *Mycobacterium tuberculosis*", DNA and Cell Biology (2012), vol. 31, No. 4, pp. 489-495.
NCBI Sequence XP_019669508.1, Predicted: Low Quality Protein: telomerase reverse transcriptase, partial [Felis catus], dated Dec. 29, 2016, 2 pages.
Muller, S., "Ubiquitin", Manual of Biological Markers of Disease (1994), B2, 3, pp. 1-11.
NCBI Sequence AAC51724.1, Telomerase catalytic subunit [*Homo sapiens*], dated Aug. 28, 1997, 2 pages.
Delogu, G. et al., "DNA Vaccine Combinations Expressing Either Tissue Plasminogen Activator Signal Sequence Fusion Proteins or Ubiquitin-Conjugated Antigens Induce Sustained Protective Immunity in a Mouse Model of Pulmonary Tuberculosis", Infection and Immunity (2002), vol. 70, No. 1, pp. 292-302.
International Search Report and Written Opinion of the International Searching Authority dated Jul. 23, 2014, which issued in International Patent Application No. PCT/EP2014/056380, 13 pages.
English Translation of Japanese Office Action Issued in JP2016-504709, dated Oct. 10, 2017, 5 pages.
English Translation of Japanese Office Action Issued in JP2016-504710, dated Oct. 10, 2017, 6 pages.
Cadile, C. D. et al., "Telomerase activity as a marker for malignancy in feline tissues", American Journal of Veterinary Research (2001), vol. 62, No. 10, pp. 1578-1581.
Huang, J. J. et al., "Ectopic Expression of a COOH-terminal Fragment of the Human Telomerase Reverse Transcriptase Leads to Telomere Dysfunction and Reduction of Growth and Tumorigenicity in HeLa Cells", Cancer Research (2002), vol. 62, pp. 3226-3232.
Huo, L. et al., "Cancer Immunotherapy Targeting the Telomerase Reverse Transcriptase" Cellular and Molecular Immunology (2006), vol. 3, No. 1, pp. 1-9.
Impellizeri, J. A. et al., "Electro-gene-transfer as a new tool for cancer immunotherapy in animals", Veterinary and Comparative Oncology, Short Communication, (Oct. 24, 2012), vol. 12, issue 4, pp. 1-9; DOI: 10.1111/vco.12006.
Ng, SSM et al., "A novel glioblastoma cancer gene therapy using AAV-mediated long-term expression of human TERT C-terminal polypeptide", Cancer Gene Therapy (2007), vol. 14, pp. 561-572.
Armbruster, B.N. et al., "N-Terminal Domains of the Human Telomerase Catalytic Subunit Required for Enzyme Activity in Vivo" Molecular and Cellular Biology (2001) vol. 21, No. 22, pp. 7775-7786.
European Communication Pursuant to Rule 114(2) EPC issued in EP14790592.1 and dated Jul. 6, 2018, 3 pages total.
Yamano, T. et al., "Immunity Against Breast Cancer by TERT DNA Vaccine Primed with Chemokine CCL21" Cancer Gene Therapy (2007) vol. 14, pp. 451-459.

* cited by examiner

```
     BamHI > Ubiquitin initiator methionine
  1  GGATCCGccgccatgcagatttcgtcaagaccatcacattggaagtggaaccagtgatactatcgaaatgtt       90
  1                M  Q  I  F  V  K  T  I  T  L  E  V  E  P  S  D  T  I  E  N  V    30

91  aaagccaaaatccaggataaggagggcattcctgaccagagacttatttcgcaggacggcagaacattg            180
 31   K  A  K  I  Q  D  K  E  G  I  P  P  D  Q  R  L  I  F  A  G  K  Q  L  E  D  G  R  T  L    60
                                              ubiquitin >< dog telomerase
181  tctgactacaacatccagaaagagcacacttcactggttctccgcctcgtggctcagtgtctgtgtgt            270
 61   S  D  Y  N  I  Q  K  E  S  T  L  H  L  V  L  R  L  R  G  G  R  A  L  V  A  Q  C  L  V  C    90

271  gtcccatggggagcacggccctccaccagcagacctgcctcaaggagtctcgtggccaggtggttcagaga        360
 91   V  P  W  G  A  R  P  P  P  A  A  P  C  F  R  Q  V  S  C  L  K  E  L  V  A  R  V  V  Q  R   120

361  ctctgcgagcggggtgcccggagacgtgctctcgcttttggattcgcactgctggacgctgaggcccaccgtgcctttacaacc  450
121   L  C  E  R  G  A  R  N  V  L  A  F  G  F  A  L  L  D  G  A  R  G  G  P  P  V  A  F  T  T  150

451  agcgtgcggtcatacctgccaacactgtgacagagacactgaggctccggggcttctgttgaggcgcttggcgacgat        540
151   S  V  R  S  Y  L  P  N  T  V  T  E  T  L  R  G  S  G  A  W  G  L  L  R  R  V  G  D  D   180

541  gtgttgacacacctgctcgcgccagtgcgcctaccaagttgcgctggtggccacaggtgtgcggacctccttgtacgac    630
181   V  L  T  H  L  L  A  R  C  A  L  Y  L  L  V  A  P  S  C  A  Y  Q  V  C  G  P  P  L  Y  D   210
```

```
 631 ctctgtgccctgcctctttgcactgcctgcccctgctcctgtcctgctgggactccctgcctgtctgggctgctcggagctgagctggcgcctcc  720
 211  L  C  A  P  A  S  L  P  L  P  A  P  G  L  P  G  L  P  G  L  G  A  G  A  G  A  S                 240
 721 gcagatctcaggctaccccgccaggcacagaatacggagccaggagagatcaggagcccaggttctggctgttctggcgtccccctggctaaaaga  810
 241  A  D  L  R  P  T  R  Q  A  Q  N  S  G  A  R  R  R  G  S  P  G  S  G  V  P  L  A  K  R           270
 811 ccacggagtcagttgcttcccgaaccgagcggggcgcacatcgtctccttcccagagccagagccaccctgtctgaggctccagca              900
 271  P  R  R  S  V  A  S  E  P  E  R  G  A  H  R  S  F  P  P  R  A  Q  P  P  V  S  E  A  P  A        300
 901 gtgacaccggctgtggccgcggcctcatggaaggagccccctgaaccaggccccactacccgcttggcaccctac                        990
 301  V  T  P  A  V  A  A  S  W  E  G  G  P  P  G  T  R  P  T  T  P  A  W  H  P  Y                   330
 991 cctggacccaggcgtcctcatgatcctgctccaactcttccggagcgagccggttctactgcagcgggagtagaacgcttcgccca             1080
 331  P  G  P  Q  G  V  P  H  D  P  A  H  P  E  T  K  R  F  L  Y  C  S  G  G  R  E  R  L  R  P        360
1081 agctttctgctcagcgccctgcctccaacctcttctcggagcccgcatgcgcccactcgtgaagctgctgggaaatcatgcaagttgc           1170
 361  S  F  L  S  A  L  P  P  T  L  S  G  A  R  K  L  V  E  T  I  F  L  G  S  S  A  P  Q  K  P        390
1171 ggagccgctaggcggaarcggtctctgcttcggactgctgcagcgagactgcctactggcgcatgcgcatgaggagctgctggaaatcatgcaagttgc 1260
 391  G  A  A  R  R  M  R  R  L  P  A  R  Y  W  R  M  R  P  L  F  Q  E  L  L  G  N  H  A  R  C        420
1261 ccctatcgggctcttccgactcactgtgcttcgggccccaggaacacggaacgattcaaccggccttgtgcaggcagcagattgttccct          1350
 421  P  Y  R  A  L  L  R  L  H  C  P  L  R  A  M  A  A  K  E  G  S  G  N  Q  A  H  R  G  V  G        450
1351 atctgtccactgcattcctgagcggctcctttggaaatctctcgagccccagatcagctagacagagagcatagttcctt                   1440
 451  I  C  P  L  E  R  P  V  A  A  P  Q  E  Q  T  D  S  T  R  L  V  Q  L  L  R  Q  H  S  S  P        480
1441 tggcaggtgtatgcattcctgagagcgcttgctctgcgcttgtgtggatgcttgccaggcagcagagggcgttcctg                     1530
 481  W  Q  V  Y  A  F  L  R  A  L  C  W  L  V  P  T  G  L  W  G  S  R  H  N  Q  R  R  F  L           510
1531 cggaacgtgaaaagtttatctctcgaaacccagctaagctgacctgaggaactgacctggaagatgaaggtgcggattgtact                1620
 511  R  N  V  K  K  F  I  S  L  G  K  H  A  K  L  S  L  Q  E  L  T  W  K  M  K  V  R  D  C  T        540
1621 tggctccacggcgcttgctggttcctgcggcgcgtgccaggccgttcctcagagcagaaattcctggccaggttccttgctcctcgtg           1710
 541  W  L  H  G  N  P  G  A  C  C  V  P  A  A  E  H  R  R  E  E  I  L  A  R  F  L  V  L  V           570
```

```
1711 gatggccacattacgtggtgaagctgctccgctcttcttacgtcaccgagactacttttcagaaaataggctgttcttctatagg 1800
 571  D  G  H  I  Y  V  V  K  L  L  R  S  F  F  Y  V  T  E  T  F  F  Q  K  N  R  L  F  F  Y  R   600

1801 aaatctgtgtggtcccagctgcagtcagtccggcatcaaccgtgcacttgcactttcaacagtgcagctttcaacttgcactgtgcgggagctccgaagcctcgcggagctccgaggttcgg 1890
 601  K  S  V  W  S  Q  L  Q  S  I  G  I  R  Q  L  E  F  N  S  V  H  L  R  E  L  S  E  A  E  V  R   630

1891 cggcacaaggagaggcaagacacccgcactcttgacatcttaggtcttgccaaagcccagcccgtgcgccgccatcgtcgtcaacatggac 1980
 631  R  H  R  E  A  R  P  A  L  L  T  S  R  L  R  F  L  P  K  P  S  G  L  R  P  I  V  N  M  D   660

1981 tatatcatgggagccagaacttcctcaccgggagaccttccacggtgcagcacctgaagcttctcagttctcaactat 2070
 661  Y  I  M  G  A  R  T  F  H  R  D  K  K  V  Q  H  L  T  S  Q  L  K  T  L  F  S  V  L  N  Y   690

2071 gagagagccagaagacccctcacttctgggcgcaagtatgttgggtatggacgacatcccatagagccgcacttcgtgctgcggatt 2160
 691  E  R  A  R  R  P  S  L  L  G  A  S  M  L  G  M  D  D  I  H  R  A  W  R  F  V  L  R  I   720

2161 agggcccagaatccagagcctactcttcgtgaagtcgacgtgcatatgacgctcccaggaccgcctgtcgaa 2250
 721  R  A  Q  N  P  A  P  Q  L  Y  F  V  K  V  D  V  T  G  A  Y  D  A  L  P  Q  D  R  L  V  E   750

2251 gtgattgccaatgtcattagacctcaggagtctacatactgtgttcgccattatgcgttcagcgttcaggttcagccacgcccgggtcatgtcaga 2340
 751  V  I  A  N  V  I  R  P  Q  E  S  T  Y  C  V  R  H  Y  A  V  V  Q  R  T  A  R  G  H  V  R   780

2341 aaggcctttcaagcgcacacgtctcaacatcgagatctccagcccctacatgagacagttcgtggagagcttcaggaaacaagctgctt 2430
 781  K  A  F  K  R  H  V  S  T  F  A  D  L  Q  P  Y  M  R  Q  F  V  E  R  L  Q  E  T  S  L  L   810

2431 agggacgcagtggtgatcgagcagtccctcaacgaggctggtccaagctcttcttctgaggctggtgcataatcac 2520
 811  R  D  A  V  V  I  E  Q  S  S  L  N  E  A  G  S  S  L  F  H  L  F  L  R  L  V  H  N  H   840

2521 gtggttaggatcgggcgtaaatcctacatccagtgtcaggtgtccccagggaagtatctctgtctactctgtagtctgttac 2610
 841  V  V  R  I  G  G  K  S  Y  I  Q  C  Q  G  V  P  Q  G  S  I  L  S  T  L  L  C  S  L  C  Y   870

(deleted catalytic aspartic acid (D) residues) ΔVDD ><
2611 ggcgacatggagagacggctgttcccggcatcgagcaggacgaggacaggacggcgttctgctcaggctgttctgttggtgactcccatctgactcag 2700
 871  G  D  M  E  R  R  L  F  P  G  I  E  Q  D  G  V  L  L  R  L  F  L  L  V  E  P  H  L  T  Q   900

2701 gcccaggccttcctccgaccctggtcaagggcgtgcccgaatacggcgtgcaacctggtgccaacctgcagaagaccgcagtcaacgcgttaacttccagtg 2790
 901  A  Q  A  F  L  R  T  L  V  K  G  V  P  E  Y  G  C  R  A  N  L  Q  K  T  A  V  N  F  P  V   930
```

FIGURE 1A CONT.

```
2791 gaggacggcgcacttggttctgccgccccattgcagctgcctgctcattgccttttcccttggtgtggcctgctgctggataccagaaca 2880
 931 E  D  G  A  L  G  S  A  A  P  L  Q  L  P  A  H  C  L  F  P  W  C  G  L  L  L  D  T  R  T   960

2881 ctggaagtctcttgcgattattcttcctatgctcacaccagtattcggccagtttgactttttcacagggcgctaaaccaggacgcaat 2970
 961 L  E  V  S  C  D  Y  S  S  Y  A  H  T  S  I  R  A  S  L  T  F  S  Q  G  A  K  P  G  R  N   990

2971 atgagacggaaacttctggccgttttgcggctgaaatgctgtgccctgttcctggatctgcaggtcaatggcattcataccgtttatatg 3060
 991 M  R  R  K  L  L  A  V  L  R  L  K  C  C  A  L  F  L  D  L  Q  V  N  G  I  H  T  V  Y  M   1020

3061 aacgtctataagatcttcctgcttcaggcctacagatttcacgcttgcgtgctgcagctgcccttcaatcagcccgtgcggaaaaacccc 3150
1021 N  V  Y  K  I  F  L  L  Q  A  Y  R  F  H  A  C  V  L  Q  L  P  F  N  Q  P  V  R  K  N  P   1050

3151 agcttctttcttcgcgtcatcgcagatacagcatcctgttgctattccttgcttaaggcaagaaatgctggactgtcactcggtgctaag 3240
1051 S  F  F  L  R  V  I  A  D  T  A  S  C  C  Y  S  L  L  K  A  R  N  A  G  L  S  L  G  A  K   1080

3241 ggtgccagcggcttgtttccaagcgaggctgccaggtggttgtgtcttcacgcattcttgctgaaattggctcaccatagcggcacatat 3330
1081 G  A  S  G  L  F  P  S  E  A  A  R  W  L  C  L  H  A  F  L  L  K  L  A  H  H  S  G  T  Y   1110

3331 aggtgtctgctgggcgccctgcaggctgctaaggctcatctgTCAagacagctcccaagaggcactctcgccgcactggaggccgcagcc 3420
1111 R  C  L  L  G  A  L  Q  A  A  K  A  H  L  S  R  Q  L  P  R  G  T  L  A  A  L  E  A  A  A   1140 dog telomerase >< influenza A A2 epitope
3421 gacccctccctcactgcagattttaagactattctcgataccgagCTTaagTTGtcagactacgagggacgcctgattcagaatAGCctg 3510
1141 D  P  S  L  T  A  D  F  K  T  I  L  D  T  E  L  K  L  S  D  Y  E  G  R  L  I  Q  N  S  L   1170

>< V5 tag                                          > XbaI
3511 acaggcaaacccattcctaatcccctgttgggtttggattccacatgataaTCTAGA   3567
1171 T  G  K  P  I  P  N  P  L  L  G  L  D  S  T  *  *          1185
```

FIGURE 1A CONT.

HindIII > Ubiquitin initiator methionine
1   AAGCTTGCCGCATGCCATGCAGATTTTCGTCAAAACCCTCACCGGCAAGACCATCACATTGGAAGTGGAACCCAGTGATACTATCGAAAATGTT  90
1              M   Q   I   F   V   K   T   L   T   G   K   T   I   T   L   E   V   E   P   S   D   T   I   E   N   V   30

91  AAAGCCAAAATCCAGGATAAGGAGGGCATTCCTCCTGACCAGCAGAGACTTATTTTCGAGGCAAACAGCTGGAGGACGGCAGAACATTG 180
31   K   A   K   I   Q   D   K   E   G   I   P   P   D   Q   Q   R   L   I   F   A   G   K   Q   L   E   D   G   R   T   L   60 ubiquitin >< dog telomerase
181 TCTGACTACAACATCCAGAAAGAGAGCACACTTCACTTGGTTCTCCGCCTTGGCTCCAGTGTCTGGTGTGT 270
61   S   D   Y   N   I   Q   K   E   S   T   L   H   L   V   L   R   L   R   G   G   R   A   L   V   A   Q   C   L   V   C   90

271 GTCCCATGGGGAGCACGGCCTCCACCAGCAGCCCCCTGCTTTAGACAGGTCAGTTGCCTCAAGGAGTCTCGTGCCCAGGTGGTTCAGAGA 360
91   V   P   W   G   A   R   P   P   P   A   A   P   C   F   R   Q   V   S   C   L   K   E   L   V   A   R   V   V   Q   R   120

361 CTCTGCGAGCGGGGTGCCCGGAACGTCCTGGCTTTTGGATTCGCACTGCTGGACGGCGCTCGCGGAGGCCCCACCCGTGGCCTTTACAACC 450
121  L   C   E   R   G   A   R   N   V   L   A   F   G   F   A   L   L   D   G   A   R   G   G   P   P   V   A   F   T   150

451 AGCGTGCGGTCATACCTGCCCAACACTGTGACAGAGACTGAGAGGCTCCGCGCTTGGGCCTTCTGTTGAGGCGCCGTTGGCGACGAT 540
151  S   V   R   S   Y   L   P   N   T   V   T   E   T   L   R   G   S   G   A   W   G   L   L   R   R   V   G   D   D   180

FIGURE 1B

```
 541 GTGTTGACACACTGCTCTGCGCAGGTGTGGCCACTTTACCTGCCTTGGTGGCCCAAGTTGCGCTACCAGGTGTGCGGACTCCTCTTTGTACGAC  630
 181  V  L  T  H  L  L  A  R  C  A  L  Y  L  L  V  A  P  S  C  A  Y  Q  V  C  G  P  P  L  Y  D  210

631 CTCTGCCCCTCTTGCCACTGCTCCTGCCCTGCCTGGACTTCCTGGTCTGCTGGAGCTGGGAGTGGAGCTGGGCGCTCC  720
 211  L  C  P  L  L  P  L  L  P  A  C  L  P  W  S  A  G  L  G  V  L  G  L  G  L  P  P  720
 211  L  C  A  P  A  S  L  P  L  P  A  P  G  L  P  G  L  P  G  L  G  A  G  A  S  240

721 GCAGATCTCAGGCCTACCCGCCAGGACAGAATAGCGGAGCCAGGTCGCCGCCGCCAGGTCTCGGGGTAGCCCCCTGGCTAAAAGA  810
 241  A  D  L  R  P  T  R  Q  A  Q  N  S  G  A  R  R  R  R  G  S  P  G  S  G  V  P  L  A  K  R  270

811 CCACGGAGGTCAGTTGCTTCCGAACCCGAGCGCCACATGCTCCTTCCCAGAGCCGCTGAACCAGCCCCCAGTGTCTGAGGCTCCAGCA  900
 271  P  R  R  S  V  A  S  E  P  E  R  G  A  H  R  S  F  P  R  A  Q  Q  P  P  V  S  E  A  P  A  300

901 GTGACACCCGCTGTGGCCGCCAGCCCTGCGCCCTGGAACCAGGGACCCCTCATGGAAGGAGAGGACCCCCTACTACCCCGCTTGGCACCCCTAC  990
 301  V  T  P  A  V  A  A  S  P  A  A  S  W  E  G  P  P  P  G  T  R  P  T  T  P  A  W  H  P  Y  330

991 CCTGGACCCCCAGGCCAGGGTCCTCCTCATGATCCGCTCACCCAGGGTTCTGTACTGCAGCGAGGTAGAGAACGCTTGCGCCCA 1080
 331  P  G  P  Q  G  P  P  Q  G  V  P  H  D  P  A  H  P  E  T  K  R  E  F  L  Y  C  S  G  R  E  R  L  R  P  360

1081 AGTTTTCTGAGCCTGGCGCCCTCAACTCTTTCGGAGCCATCTTTCTCGTAGCGCCTCCTCAGAAACCA 1170
 361  S  F  L  S  A  L  P  P  T  L  S  G  A  R  K  L  V  E  T  I  F  F  L  G  S  A  P  Q  K  F  390

1171 GGAGCCGCTAGGCGGATGCGCAGACTGCCTGCACGCTACTGGCGCATGCGCTTCCTGCAGGAAATCATGCAAGGTGC 1260
 391  G  A  A  R  R  M  R  R  L  P  A  R  Y  W  R  M  R  F  L  Q  E  I  L  G  N  H  A  R  C  420

1261 CCCTATCGGGCTCTGCTTCGGACTCACTGTCCACTGAGGCTATGGCAGCAAAGGAAGTGGAAAACCAGCCCATAGAGGAGTCGGT 1350
 421  P  Y  R  A  L  L  R  T  H  C  P  L  R  A  M  A  A  K  E  G  S  G  N  Q  A  H  R  G  V  G  450 dog TERT >< cat TERT

1351 ATCTGTCCACTGGAGCCGCCCAGGAACGACCGATTCAACCGCCTTGTGCAGTCTCCTGAGGCAGCACAGTAGCCCA  1440
 451  I  C  P  L  E  R  P  V  A  A  P  Q  E  Q  T  D  S  T  R  L  V  Q  L  L  R  Q  H  S  S  P  480

1441 TGGCAGGTGTATGCTTTTCTTCGCGCTTGTCTGTGCCGCGCTGGTCTGTGTGGGCAGCGGCCACAACAGAAGAGCCTTTTG 1530
 481  W  Q  V  Y  A  F  L  R  A  C  L  C  R  L  V  P  A  G  L  W  G  S  G  H  N  R  R  F  L  510

1531 CGGAATGTGAAAAAGTTCGTGTCCCTGGAAAGCACGCTAAACTGTCATTGCAGGAGCTGACTGACTGGAAGATGCGGGTGCAGGATTGTGCA  1620
 511  R  N  V  K  K  F  V  S  L  G  K  H  A  K  L  S  L  Q  E  L  T  W  K  M  R  V  Q  D  C  A  540
```

FIGURE 1B CONT.

```
1621 TGGCTGAGGGGCTCTCCGGAGCCCGTCCGCCGAGGAGGTGCTCGCAAAGCTCTTGTGCTGG 1710
 541  W  L  R  G  S  P  G  A  R  C  V  P  A  A  E  H  R  R  R  E  E  V  L  A  K  L  L  C  W  L  570

1711 ATGGGAACCTACGTGGTCGAACTGCTGAAATCTTTTTTCTATGTCACTGAGACATTCCAGAAGAATCGCCTGTTCTTTTACCGGAAA 1800
 571  M  G  T  Y  V  V  E  L  L  K  S  F  F  Y  V  T  E  T  F  Q  K  N  R  L  F  F  Y  R  K  600

1801 AGGATCTGGTCCCAGCTTCAGAGCATTGGCATCCGGCAGCATTTTAACTCTGTTCACCTGAGGGAGCTGAGCGAGGCAGAAGTGAGGCGC 1890
 601  R  I  W  S  Q  L  Q  S  I  G  I  R  Q  H  F  N  S  V  H  L  R  E  L  S  E  A  E  V  R  R  630

1891 CATCAGGAGGCCCGCCCCACTCTGCTTACCTCCAAGTCGCGGTTCCTGCCTAAACATCAGGTCTGAGACCCATTGTCAACATGGATTAC 1980
 631  H  Q  E  A  R  P  T  L  L  T  S  K  L  R  F  L  P  K  P  S  G  L  R  P  I  V  N  M  D  Y  660

1981 GTGGTGGGGCCAGAACATTCAGAAGACAAAAAAGGTTCGGCATCTCACCTGTTTTCTGTTCTGAACTACGAA 2070
 661  V  V  G  A  R  T  F  R  R  D  K  K  V  R  H  L  T  S  Q  V  K  N  L  F  S  V  L  N  Y  E  690

2071 AGGGCCAGGAGGCCATCACTGCTGGGTGCCAGTGCTGATGATATTCACAGACGATATTCACAGAGTCTGGCGGAGCTTCGTGCTTCGGGTGAGA 2160
 691  R  A  R  R  P  S  L  L  G  A  S  V  L  G  M  D  D  I  H  R  V  W  R  S  F  V  L  R  V  R  720

2161 GCTCAGGACCCCGCCCCACAGTTGTATTTTGTCAAGGTCGATGTGACTGGTGCTTATGACGCTCTCCCTCAGGACAAATTGGTGGAGGTG 2250
 721  A  Q  D  P  A  P  Q  L  Y  F  V  K  V  D  V  T  G  A  Y  D  A  L  P  Q  D  K  L  V  E  V  750

2251 ATCGCTAATGTCATCCGCCCCCAGGAGAATACATACTGCGTGCGCCATTACGCTGTGGTGCAGCGCACGGCCCAGGGCCACGTGAGGAAA 2340
 751  I  A  N  V  I  R  P  Q  E  N  T  Y  C  V  R  H  Y  A  V  V  Q  R  T  A  Q  G  H  V  R  K  780

2341 TCCTTCAAGCGGCATGTGTCCACCTTCGTCGACCTGCAGCCCTATATGCGCCAGTTTGTGGAGCACCTGCAGGAAACTTCAAGCCTTAGG 2430
 781  S  F  K  R  H  V  S  T  F  V  D  L  Q  P  Y  M  R  Q  F  V  E  H  L  Q  E  T  S  S  L  R  810

2431 GATGCCGTTGTTATCGAGCAGAGTTCTAGTCTCAACGAGACCGGACACAGTCTCTTTCTGAGGCTCGTGCATAATCATGTC 2520
 811  D  A  V  V  I  E  Q  S  S  S  L  N  E  T  G  H  S  L  F  L  R  L  V  H  N  H  V  840

2521 ATCCGCATTGGAGGAAAATCTTATGTTCAGTGCCAGGGCATCCCTCAGGGTTCTATCCTGTCTTTCTGCTCTCTTGTTACGGC 2610
 841  I  R  I  G  G  K  S  Y  V  Q  C  Q  G  I  P  Q  G  S  I  L  S  F  L  L  C  S  L  C  Y  G  870

2611 GATATGGAAAGTAGGCTTTTCTCAGGAATCCAGCAGGACGGCGTCCTGCTGCGGCGTCTTCTTCTTGGTGACACCTCACCTGGACACAGGCC 2700
 871  D  M  E  S  R  L  F  S  G  I  Q  Q  D  G  V  L  L  R  L  F  L  L  V  T  P  H  L  A  Q  A  900
```

(deleted catalytic aspartic acid (D) residues) >< ΔVDD

FIGURE 1B CONT.

```
2701 CAGGCCTTCCTGCGCACACTGGTGAGCGGAGTGCCTGAGTACGGCTGTACCGCCAACCTGCAGAAGACAGCCGTGAATTTTCCAGTGGAC 2790
 901 Q   A   F   L   R   T   L   V   S   G   V   P   E   Y   G   C   T   A   N   L   Q   K   T   A   V   N   F   P   V   D    930

2791 ACCGGTGCTCCGCCAGGCTCCGCCGCCACCTGTCTCTTTCCTTGGTGTGCGGACTGCTGGACACCCGGACTTTG 2880
 931 T   G   A   P   G   S   A   A   P   L   Q   L   P   A   H   C   L   F   P   W   C   G   L   L   D   T   R   T   L    960

2881 GAAGTCTTTTGCGATTACTCCAGCTATGCACAGACAATCATTAGGAGCAGCCTGACATTCAGCAGGTCACACGGCCCGCAATATG 2970
 961 E   V   F   C   D   Y   S   S   Y   A   Q   T   S   I   R   S   S   L   T   F   S   Q   G   T   R   P   G   R   N   M    990

2971 AGGAGAAAGTTGCTCGCCGTTATGAGACTCAAGTGCTGTGCAGTCTTTCTTGATCTGCAGGTCAATTCTATTCATACCGTTACACCAAC 3060
 991 R   R   K   L   L   A   V   M   R   L   K   C   C   A   V   F   L   D   L   Q   V   N   S   I   H   T   V   Y   T   N   1020

3061 ATCTATAAAATTTTCCTGCTCCAGGCATATAGATTTCACGCCGTGTTGCAGTTCCCATTCAATCAGCCCGTTCGGAAGAACCCCAGT 3150
1021 I   Y   K   I   F   L   L   Q   A   Y   R   F   H   A   C   V   L   Q   F   F   N   Q   P   V   R   K   N   P   S   1050

3151 TTCTTTCTCAGGTTATTGCTGATACCGCCTCCCGCTGTTACTCCCTGCTTAAGGCACTTTCATTGGTGCTAAAGGC 3240
1051 F   F   L   R   V   I   A   D   T   A   S   R   C   Y   S   L   L   K   A   K   N   T   G   L   S   L   G   A   R   G   1080

3241 GCCAGTGGACCTTTCCCTTCTGAAGCCGCTCGGTGGCTCCATTCCTTCTGTTTGCACGCATTCTTGAAGTTGGCTAGACACAGTCTACTTACAGA 3330
1081 A   S   G   P   F   P   S   E   A   A   R   W   L   C   L   H   A   F   L   K   L   A   R   H   S   S   T   Y   R   1110
         cat TERT ><  dog TERT
3331 TGCCTTTCTGGGCCCCCTTAGAGCTGCTAAGGCTAAAGCTAAAGCTAAACAAGCTCATCTGTCAAGACAGCTCCCAAGAGGCACTCTCGCCGCACTGGAGGCCGCAGCCGAC 3420
1111 C   L   L   G   P   L   R   A   K   A   H   L   S   R   Q   L   P   R   G   T   L   A   A   L   E   A   A   D   1140
                                                           dog telomerase ><  influenza A A2 epitope
                                                                                                             >
3421 CCCTCCCTCACTGCAGATTTTAAGACTATTCTCGATACCGAGCTTAAGTTGTCAGATTACGAGGACGCCTGATTCAGAATAGCCTGACA 3510
1141 P   S   L   T   A   D   F   K   T   I   L   D   T   E   L   K   L   S   D   Y   E   G   R   L   I   Q   N   S   L   T   1170
         V5 tag
                          >       Xbal
3511 GGCAAACCCATTCCTAATCCCCTGTTTGGGATTCCACATGATAATCTAGA 3564
1171 G   K   P   I   P   N   P   L   L   G   L   D   S   T   *   *   1184
```

FIGURE 1B CONT.

```
   1 MPRAPRCRAV RALLRGRYRE VLPLATFLRR LGPPGRLLVR RGDPAAFRAL VAQCLVCVPW
  61 GARPPPAAPC FRQVSCLKEL VARVVQRLCE RGARNVLAFG FALLDGARGG PPVAFTTSVR
 121 SYLPNTVTET LRGSGAWGLL LRRVGDDVLT HLLARCALYL LVAPSCAYQV CGPPLYDLCA
 181 PASLPLPAPG LPGLPGLPGL GAGAGASADL RPTRQAQNSG ARRRRGSPGS GVPLAKRPRR
 241 SVASEPERGA HRSFPRAQQP PVSEAPAVTP AVAASPAASW EGGPPGTRPT TPAWHPYPGR
 301 QGVPHDPAHP ETKRFLYCSG GRERLRPSEL LSALPPTLSG ARKLVETIFL GSAPQKPGAA
 361 RRMRRLPARY WRMRPLFQEL LGNHARCPYR ALLRTHCFLR AMAAKEGSGN QAHRGVGICP
 421 LERPVAAPQE QTDSTRLVQL LRQHSSPWQV YAFLRACLCW LVPTGLWGSR HNQRRFLRNV
 481 KKFISLGKHA KLSLQELTWK MKVRDCIWLR GNPGACCVPA AEHRRREEIL ARFLVLVDGH
 541 IYVVKLLRSF FYVTETTFQK NRLFFYRKSV WSQLQSIGIR QLFNSVHLRE LSEAEVRRHR
 601 EARPALLTSR LRFLPKPSGL RPIVNMDYIM GARTFHRDKK VQHLTSQLKT LFSVLNYERA
 661 RRPSLLGASM LGMDDIHRAW RTFVLRIRAQ NPAPQLYFVK VDVTGAYDAL PQDRLVEVIA
 721 NVIRPQESTY CVRHYAVVQR TARGHVRKAF KRHVSTFADL QPYMRQFVER LQETSLLRDA
 781 VVIEQSSSLN EAGSSLFHLF LRLVHNHVVR IGGKSYIQCQ GVPQGSILST LLCSLCYGDM
 841 ERRLFPGIEQ DGVLLRLVDD FLLVTPHLTQ AQAFLRTLVK GVPEYGCRAN LQKTAVNFPV
 901 EDGALGSAAP LQLPAHCLFP WCGLLLDTRT LEVSCDYSSY AHTSIRASLT FSQGAKPGRN
 961 MRRKLLAVLR LKCCALFLDL QVNGIHTVYM NVYKIFLLQA YRFHACVLQL PFNQPVRKNP
1021 SFFLRVIADT ASCCYSLLKA RNAGLSLGAK GASGLFPSEA ARWLCLHAFL LKLAHHSGTY
1081 RCLLGALQAA KAHLSRQLPR GTLAALEAAA DPSLTADFKT ILD
```

FIGURE 2B

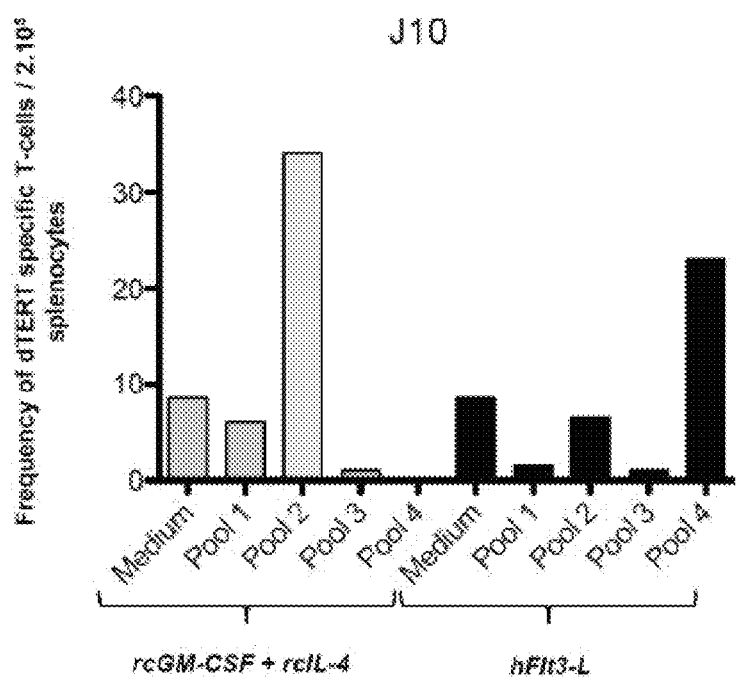
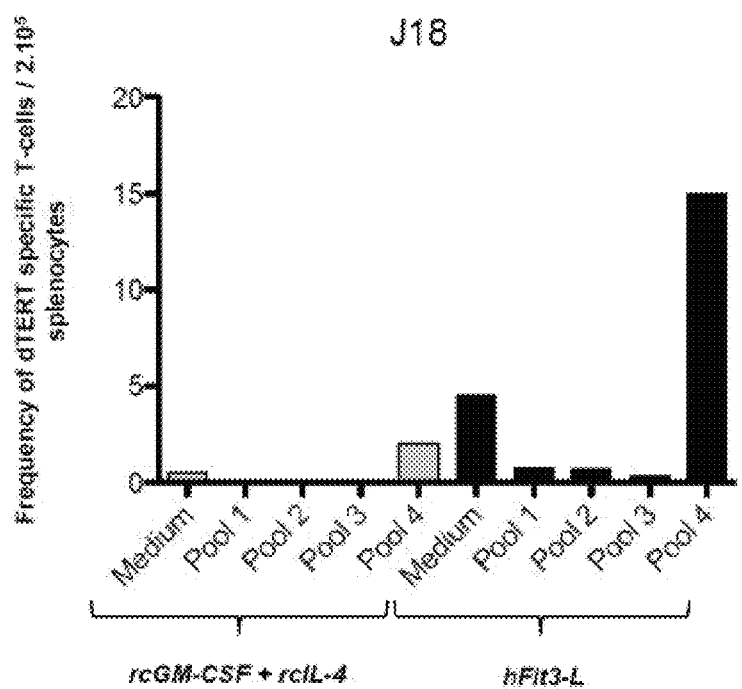
FIGURE 9

SEQUENCE LISTING

```
<160> NUMBER OF SEQ ID NOS: 92

<210> SEQ ID NO 1
<211> LENGTH: 3567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pDUV5 plasmid sequence
<220> FEATURE:
<221> NAME/KEY: CDS
<222> LOCATION: (13)..(3555)

<400> SEQUENCE: 1
ggatccgccg cc atg cag att ttc gtc aaa acc ctc acc ggc aag acc atc          51
              Met Gln Ile Phe Val Lys Thr Leu Thr Gly Lys Thr Ile
                1               5                  10 aca ttg gaa gtg gaa ccc agt gat act atc gaa aat gtt aaa gcc aaa            99
Thr Leu Glu Val Glu Pro Ser Asp Thr Ile Glu Asn Val Lys Ala Lys
     15                  20                  25 atc cag gat aag gag ggc att cct cct gac cag cag aga ctt att ttc           147
Ile Gln Asp Lys Glu Gly Ile Pro Pro Asp Gln Gln Arg Leu Ile Phe
 30                  35                  40                  45 gca ggc aaa cag ctg gag gac ggc aga aca ttg tct gac tac aac atc           195
Ala Gly Lys Gln Leu Glu Asp Gly Arg Thr Leu Ser Asp Tyr Asn Ile
                 50                  55                  60 cag aaa gag agc aca ctt cac ttg gtt ctc cgc ctt cgc gga gga cgg           243
Gln Lys Glu Ser Thr Leu His Leu Val Leu Arg Leu Arg Gly Gly Arg
     65                  70                  75 gcc ctc gtg gct cag tgt ctg gtg tgt gtc cca tgg gga gca cgg cct           291
Ala Leu Val Ala Gln Cys Leu Val Cys Val Pro Trp Gly Ala Arg Pro
 80                  85                  90 cca cca gca gcc ccc tgc ttt aga cag gtc agt tgc ctc aag gag ctc           339
Pro Pro Ala Ala Pro Cys Phe Arg Gln Val Ser Cys Leu Lys Glu Leu
     95                 100                 105 gtg gcc agg gtg gtt cag aga ctc tgc gag cgg ggt gcc cgg aac gtc           387
Val Ala Arg Val Val Gln Arg Leu Cys Glu Arg Gly Ala Arg Asn Val
110                 115                 120                 125 ctc gct ttt gga ttc gca ctg ctg gac ggc gct cgg gga cca ccc               435
Leu Ala Phe Gly Phe Ala Leu Leu Asp Gly Ala Arg Gly Pro Pro
                130                 135                 140 gtg gcc ttt aca acc agc gtg cgg tca tac ctg ccc aac act gtg aca           483
Val Ala Phe Thr Thr Ser Val Arg Ser Tyr Leu Pro Asn Thr Val Thr
                145                 150                 155 gag aca ctg aga ggc tcc ggc gct tgg ggc ctt ctg ttg agg cgc gtt           531
Glu Thr Leu Arg Gly Ser Gly Ala Trp Gly Leu Leu Leu Arg Arg Val
```

```
                 160                 165                 170
ggc gac gat gtg ttg aca cac ctg ctc gcc agg tgc gca ctt tac ctg       579
Gly Asp Asp Val Leu Thr His Leu Leu Ala Arg Cys Ala Leu Tyr Leu
        175                 180                 185 ctg gtg gcc cca agt tgc gcc tac cag gtg tgc gga cct cct ttg tac       627
Leu Val Ala Pro Ser Cys Ala Tyr Gln Val Cys Gly Pro Pro Leu Tyr
190                 195                 200                 205 gac ctc tgt gcc cct gcc tct ttg cca ctg cct gcc cct ggc ctg cct       675
Asp Leu Cys Ala Pro Ala Ser Leu Pro Leu Pro Ala Pro Gly Leu Pro
                210                 215                 220 gga ctt cct ggt ctg cct ggt ctc ggc gct gga gct ggc gcc tcc gca       723
Gly Leu Pro Gly Leu Pro Gly Leu Gly Ala Gly Ala Gly Ala Ser Ala
            225                 230                 235 gat ctc agg cct acc cgc cag gca cag aat agc gga gcc agg cgc cgc       771
Asp Leu Arg Pro Thr Arg Gln Ala Gln Asn Ser Gly Ala Arg Arg Arg
        240                 245                 250 cgg ggt agc cca ggt tct ggc gtc ccc ctg gct aaa aga cca cgg agg       819
Arg Gly Ser Pro Gly Ser Gly Val Pro Leu Ala Lys Arg Pro Arg Arg
255                 260                 265 tca gtt gct tcc gaa ccc gag cgg ggc gca cat cgc tcc ttt ccc aga       867
Ser Val Ala Ser Glu Pro Glu Arg Gly Ala His Arg Ser Phe Pro Arg
270                 275                 280                 285 gcc cag cag cca cct gtg tct gag gct cca gca gtg aca ccc gct gtg       915
Ala Gln Gln Pro Pro Val Ser Glu Ala Pro Ala Val Thr Pro Ala Val
                290                 295                 300 gcc gcc agc cct gcc gcc tca tgg gaa gga gga ccc cct gga acc agg       963
Ala Ala Ser Pro Ala Ala Ser Trp Glu Gly Gly Pro Pro Gly Thr Arg
            305                 310                 315 ccc act acc ccc gct tgg cac ccc tac cct gga ccc cag ggc gtc cct      1011
Pro Thr Thr Pro Ala Trp His Pro Tyr Pro Gly Pro Gln Gly Val Pro
        320                 325                 330 cat gat cct gct cac cca gaa acc aag cgg ttc ctg tac tgc agc gga      1059
His Asp Pro Ala His Pro Glu Thr Lys Arg Phe Leu Tyr Cys Ser Gly
335                 340                 345 ggt aga gaa cgc ttg cgc cca agc ttt ctg ctc agc gcc ctg cct cca      1107
Gly Arg Glu Arg Leu Arg Pro Ser Phe Leu Leu Ser Ala Leu Pro Pro
350                 355                 360                 365 act ctt tcc gga gcc cgg aaa ctc gtg gaa acc atc ttt ctc ggt agc      1155
Thr Leu Ser Gly Ala Arg Lys Leu Val Glu Thr Ile Phe Leu Gly Ser
                370                 375                 380 gct cct cag aaa cca gga gcc gct agg cgg atg cgc aga ctg cct gca      1203
Ala Pro Gln Lys Pro Gly Ala Ala Arg Arg Met Arg Arg Leu Pro Ala
            385                 390                 395 cgc tac tgg cgc atg cgc cca ctc ttt cag gag ctg ctg gga aat cat      1251
Arg Tyr Trp Arg Met Arg Pro Leu Phe Gln Glu Leu Leu Gly Asn His
        400                 405                 410 gca agg tgc ccc tat cgg gct ctg ctt cgg act cac tgt cca ctg aga      1299
Ala Arg Cys Pro Tyr Arg Ala Leu Leu Arg Thr His Cys Pro Leu Arg
415                 420                 425 gct atg gca gca aag gaa gga agt gga aac cag gcc cat aga gga gtc      1347
Ala Met Ala Ala Lys Glu Gly Ser Gly Asn Gln Ala His Arg Gly Val
430                 435                 440                 445 ggt atc tgt cca ctg gag cgc ccc gtt gct gcc ccc cag gaa cag acc      1395
Gly Ile Cys Pro Leu Glu Arg Pro Val Ala Ala Pro Gln Glu Gln Thr
                450                 455                 460 gat tca acc cgc ctt gtg cag ctg ctc agg cag cat agt tcc cct tgg      1443
Asp Ser Thr Arg Leu Val Gln Leu Leu Arg Gln His Ser Ser Pro Trp
            465                 470                 475 cag gtg tat gca ttc ctg aga gct tgc ctg tgc tgg ctg gtg cca acc      1491
```

```
           Gln Val Tyr Ala Phe Leu Arg Ala Cys Leu Cys Trp Leu Val Pro Thr
                   480                 485                 490 ggc ctc tgg ggc agt aga cac aac cag agg cgc ttt ctg cgg aac gtg       1539
Gly Leu Trp Gly Ser Arg His Asn Gln Arg Arg Phe Leu Arg Asn Val
        495                 500                 505 aaa aag ttt atc tct ctc gga aaa cac gct aag ctg agc ctc cag gaa       1587
Lys Lys Phe Ile Ser Leu Gly Lys His Ala Lys Leu Ser Leu Gln Glu
510                 515                 520                 525 ctg acc tgg aag atg aag gtg cgg gat tgt act tgg ctc cac ggc aac       1635
Leu Thr Trp Lys Met Lys Val Arg Asp Cys Thr Trp Leu His Gly Asn
                    530                 535                 540 cca ggc gct tgc tgc gtt cca gct gca gag cac agg agg cgg gaa gaa       1683
Pro Gly Ala Cys Cys Val Pro Ala Ala Glu His Arg Arg Arg Glu Glu
                545                 550                 555 att ctg gcc agg ttc ctt gtc ctc gtg gat ggc cac att tac gtg gtg       1731
Ile Leu Ala Arg Phe Leu Val Leu Val Asp Gly His Ile Tyr Val Val
            560                 565                 570 aag ctg ctc cgc tcc ttc ttt tac gtc acc gag act act ttt cag aaa       1779
Lys Leu Leu Arg Ser Phe Phe Tyr Val Thr Glu Thr Thr Phe Gln Lys
        575                 580                 585 aat agg ctg ttc ttc tat agg aaa tct gtg tgg tcc cag ctg cag tca       1827
Asn Arg Leu Phe Phe Tyr Arg Lys Ser Val Trp Ser Gln Leu Gln Ser
590                 595                 600                 605 atc ggc atc cgg cag ctt ttc aac agt gtg cac ttg cgg gag ctc tcc       1875
Ile Gly Ile Arg Gln Leu Phe Asn Ser Val His Leu Arg Glu Leu Ser
                    610                 615                 620 gaa gcc gag gtt cgg cgg cac agg gag gca aga ccc gca ctc ttg aca       1923
Glu Ala Glu Val Arg Arg His Arg Glu Ala Arg Pro Ala Leu Leu Thr
                625                 630                 635 tct agg ctt agg ttt ttg cca aag ccc agc ggc ctg cgc ccc atc gtc       1971
Ser Arg Leu Arg Phe Leu Pro Lys Pro Ser Gly Leu Arg Pro Ile Val
            640                 645                 650 aac atg gac tat atc atg gga gcc agg acc ttc cac cgg gac aag aag       2019
Asn Met Asp Tyr Ile Met Gly Ala Arg Thr Phe His Arg Asp Lys Lys
        655                 660                 665 gtg cag cac ctg act tct cag ctg aag aca ctg ttc tca gtt ctc aac       2067
Val Gln His Leu Thr Ser Gln Leu Lys Thr Leu Phe Ser Val Leu Asn
670                 675                 680                 685 tat gag aga gcc aga aga ccc tca ctt ctg ggc gca agt atg ttg ggt       2115
Tyr Glu Arg Ala Arg Arg Pro Ser Leu Leu Gly Ala Ser Met Leu Gly
                    690                 695                 700 atg gac gac atc cat aga gcc tgg cgc acc ttc gtg ctg cgg att agg       2163
Met Asp Asp Ile His Arg Ala Trp Arg Thr Phe Val Leu Arg Ile Arg
                705                 710                 715 gcc cag aat cca gcc ccc cag ctc tac ttc gtg aag gtc gac gtg acc       2211
Ala Gln Asn Pro Ala Pro Gln Leu Tyr Phe Val Lys Val Asp Val Thr
            720                 725                 730 ggt gca tat gac gct ctc cct cag gac cgc ctt gtc gaa gtg att gcc       2259
Gly Ala Tyr Asp Ala Leu Pro Gln Asp Arg Leu Val Glu Val Ile Ala
        735                 740                 745 aat gtc att aga cct cag gag tct aca tac tgt gtt cgc cat tat gcc       2307
Asn Val Ile Arg Pro Gln Glu Ser Thr Tyr Cys Val Arg His Tyr Ala
750                 755                 760                 765 gtg gtt cag cgc acc gcc cgg ggt cat gtc aga aag gcc ttc aag cgg       2355
Val Val Gln Arg Thr Ala Arg Gly His Val Arg Lys Ala Phe Lys Arg
                    770                 775                 780 cac gtc tca aca ttc gca gat ctc cag ccc tac atg aga cag ttc gtg       2403
His Val Ser Thr Phe Ala Asp Leu Gln Pro Tyr Met Arg Gln Phe Val
                785                 790                 795
```

```
gag agg ctt cag gaa aca agc ctg ctt agg gac gca gtg gtg atc gag    2451
Glu Arg Leu Gln Glu Thr Ser Leu Leu Arg Asp Ala Val Val Ile Glu
        800                 805                 810 cag agc tct tcc ctt aac gaa gct ggt tcc agc ctg ttc cac ctc ttt    2499
Gln Ser Ser Ser Leu Asn Glu Ala Gly Ser Ser Leu Phe His Leu Phe
815                 820                 825 ctg agg ctg gtg cat aat cac gtg gtt agg atc ggc ggt aaa tcc tac    2547
Leu Arg Leu Val His Asn His Val Val Arg Ile Gly Gly Lys Ser Tyr
830                 835                 840                 845 att cag tgt cag ggt gtc ccc cag gga agt atc ctg tct act ctg ctc    2595
Ile Gln Cys Gln Gly Val Pro Gln Gly Ser Ile Leu Ser Thr Leu Leu
                850                 855                 860 tgt agt ctg tgt tac ggc gac atg gag aga cgg ctg ttt ccc ggc atc    2643
Cys Ser Leu Cys Tyr Gly Asp Met Glu Arg Arg Leu Phe Pro Gly Ile
                865                 870                 875 gag cag gac ggc gtt ctg ctc agg ctg ttt ctg ttg gtg act ccc cat    2691
Glu Gln Asp Gly Val Leu Leu Arg Leu Phe Leu Leu Val Thr Pro His
        880                 885                 890 ctg act cag gcc cag gcc ttc ctc cgc acc ctg tcc aag ggc gtg ccc    2739
Leu Thr Gln Ala Gln Ala Phe Leu Arg Thr Leu Val Lys Gly Val Pro
895                 900                 905 gaa tac gga tgc aga gcc aac ctg cag aag acc gcc gtt aac ttt cca    2787
Glu Tyr Gly Cys Arg Ala Asn Leu Gln Lys Thr Ala Val Asn Phe Pro
910                 915                 920                 925 gtg gag gac ggc gca ctt ggt tct gcc gcc cca ttg cag ctg cct gct    2835
Val Glu Asp Gly Ala Leu Gly Ser Ala Ala Pro Leu Gln Leu Pro Ala
                930                 935                 940 cat tgc ctt ttc cct tgg tgt ggc ctg ctg ctg gat acc aga aca ctg    2883
His Cys Leu Phe Pro Trp Cys Gly Leu Leu Leu Asp Thr Arg Thr Leu
                945                 950                 955 gaa gtc tct tgc gat tat tct tcc tat gct cac acc agt att cgg gcc    2931
Glu Val Ser Cys Asp Tyr Ser Ser Tyr Ala His Thr Ser Ile Arg Ala
        960                 965                 970 agt ttg act ttt tca cag ggc gct aaa cca gga cgc aat atg aga cgg    2979
Ser Leu Thr Phe Ser Gln Gly Ala Lys Pro Gly Arg Asn Met Arg Arg
975                 980                 985 aaa ctt ctg gcc gtt ttg cgg ctg aaa tgc tgt  gcc ctg ttc ctg gat   3027
Lys Leu Leu Ala Val Leu Arg Leu Lys Cys Cys  Ala Leu Phe Leu Asp
990                 995                 1000                1005 ctg cag gtc aat ggc  att cat acc gtt tat  atg aac gtc tat aag      3072
Leu Gln Val Asn Gly  Ile His Thr Val Tyr  Met Asn Val Tyr Lys
                1010                1015                1020 atc ttc ctg ctt cag  gcc tac aga ttt cac  gct tgc gtg ctg cag      3117
Ile Phe Leu Leu Gln  Ala Tyr Arg Phe His  Ala Cys Val Leu Gln
                1025                1030                1035 ctg ccc ttc aat cag  ccc gtg cgg aaa aac  ccc agc ttc ttt ctt      3162
Leu Pro Phe Asn Gln  Pro Val Arg Lys Asn  Pro Ser Phe Phe Leu
                1040                1045                1050 cgc gtc atc gca gat  aca gca tcc tgt tgc  tat tcc ttg ctt aag      3207
Arg Val Ile Ala Asp  Thr Ala Ser Cys Cys  Tyr Ser Leu Leu Lys
                1055                1060                1065 gca aga aat gct gga  ctg tca ctc ggt gct  aag ggt gcc agc ggc      3252
Ala Arg Asn Ala Gly  Leu Ser Leu Gly Ala  Lys Gly Ala Ser Gly
                1070                1075                1080 ttg ttt cca agc gag  gct gcc agg tgg ttg  tgt ctt cac gca ttc      3297
Leu Phe Pro Ser Glu  Ala Ala Arg Trp Leu  Cys Leu His Ala Phe
                1085                1090                1095 ttg ctg aaa ttg gct  cac cat agc ggc aca  tat agg tgt ctg ctg      3342
Leu Leu Lys Leu Ala  His His Ser Gly Thr  Tyr Arg Cys Leu Leu
                1100                1105                1110
```

```
ggc gcc ctg cag gct gct aag gct cat ctg tca aga cag ctc cca    3387
Gly Ala Leu Gln Ala Ala Lys Ala His Leu Ser Arg Gln Leu Pro
                1115            1120            1125 aga ggc act ctc gcc gca ctg gag gcc gca gcc gac ccc tcc ctc    3432
Arg Gly Thr Leu Ala Ala Leu Glu Ala Ala Ala Asp Pro Ser Leu
                1130            1135            1140 act gca gat ttt aag act att ctc gat acc gag ctt aag ttg tca    3477
Thr Ala Asp Phe Lys Thr Ile Leu Asp Thr Glu Leu Lys Leu Ser
                1145            1150            1155 gac tac gag gga cgc ctg att cag aat agc ctg aca ggc aaa ccc    3522
Asp Tyr Glu Gly Arg Leu Ile Gln Asn Ser Leu Thr Gly Lys Pro
                1160            1165            1170 att cct aat ccc ctg ttg ggt ttg gat tcc aca tgataatcta ga      3567
Ile Pro Asn Pro Leu Leu Gly Leu Asp Ser Thr
                1175            1180

<210> SEQ ID NO 2
<211> LENGTH: 1181
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Arg Ala Leu Val
65                  70                  75                  80

Ala Gln Cys Leu Val Cys Val Pro Trp Gly Ala Arg Pro Pro Pro Ala
                85                  90                  95

Ala Pro Cys Phe Arg Gln Val Ser Cys Leu Lys Glu Leu Val Ala Arg
            100                 105                 110

Val Val Gln Arg Leu Cys Glu Arg Gly Ala Arg Asn Val Leu Ala Phe
        115                 120                 125

Gly Phe Ala Leu Leu Asp Gly Ala Arg Gly Gly Pro Pro Val Ala Phe
    130                 135                 140

Thr Thr Ser Val Arg Ser Tyr Leu Pro Asn Thr Val Thr Glu Thr Leu
145                 150                 155                 160

Arg Gly Ser Gly Ala Trp Gly Leu Leu Leu Arg Arg Val Gly Asp Asp
                165                 170                 175

Val Leu Thr His Leu Leu Ala Arg Cys Ala Leu Tyr Leu Leu Val Ala
            180                 185                 190

Pro Ser Cys Ala Tyr Gln Val Cys Gly Pro Pro Leu Tyr Asp Leu Cys
        195                 200                 205

Ala Pro Ala Ser Leu Pro Leu Pro Ala Pro Gly Leu Pro Gly Leu Pro
    210                 215                 220

Gly Leu Pro Gly Leu Gly Ala Gly Ala Gly Ser Ala Asp Leu Arg
225                 230                 235                 240

Pro Thr Arg Gln Ala Gln Asn Ser Gly Ala Arg Arg Arg Gly Ser
                245                 250                 255
```

```
Pro Gly Ser Gly Val Pro Leu Ala Lys Arg Pro Arg Ser Val Ala
            260                 265             270

Ser Glu Pro Glu Arg Gly Ala His Arg Ser Phe Pro Arg Ala Gln Gln
        275                 280             285

Pro Pro Val Ser Glu Ala Pro Val Thr Pro Ala Val Ala Ala Ser
    290                 295             300

Pro Ala Ala Ser Trp Glu Gly Pro Pro Gly Thr Arg Pro Thr Thr
305                 310             315                 320

Pro Ala Trp His Pro Tyr Pro Gly Pro Gln Gly Val Pro His Asp Pro
                325             330             335

Ala His Pro Glu Thr Lys Arg Phe Leu Tyr Cys Ser Gly Gly Arg Glu
            340             345             350

Arg Leu Arg Pro Ser Phe Leu Leu Ser Ala Leu Pro Pro Thr Leu Ser
        355             360             365

Gly Ala Arg Lys Leu Val Glu Thr Ile Phe Leu Gly Ser Ala Pro Gln
    370             375             380

Lys Pro Gly Ala Ala Arg Arg Met Arg Arg Leu Pro Ala Arg Tyr Trp
385             390             395                 400

Arg Met Arg Pro Leu Phe Gln Glu Leu Leu Gly Asn His Ala Arg Cys
                405             410             415

Pro Tyr Arg Ala Leu Leu Arg Thr His Cys Pro Leu Arg Ala Met Ala
            420             425             430

Ala Lys Glu Gly Ser Gly Asn Gln Ala His Arg Gly Val Gly Ile Cys
        435             440             445

Pro Leu Glu Arg Pro Val Ala Ala Pro Gln Glu Gln Thr Asp Ser Thr
    450             455             460

Arg Leu Val Gln Leu Leu Arg Gln His Ser Ser Pro Trp Gln Val Tyr
465             470             475                 480

Ala Phe Leu Arg Ala Cys Leu Cys Trp Leu Val Pro Thr Gly Leu Trp
                485             490             495

Gly Ser Arg His Asn Gln Arg Arg Phe Leu Arg Asn Val Lys Lys Phe
            500             505             510

Ile Ser Leu Gly Lys His Ala Lys Leu Ser Leu Gln Glu Leu Thr Trp
        515             520             525

Lys Met Lys Val Arg Asp Cys Thr Trp Leu His Gly Asn Pro Gly Ala
    530             535             540

Cys Cys Val Pro Ala Ala Glu His Arg Arg Glu Glu Ile Leu Ala
545             550             555             560

Arg Phe Leu Val Leu Val Asp Gly His Ile Tyr Val Lys Leu Leu
                565             570             575

Arg Ser Phe Phe Tyr Val Thr Glu Thr Thr Phe Gln Lys Asn Arg Leu
            580             585             590

Phe Phe Tyr Arg Lys Ser Val Trp Ser Gln Leu Gln Ser Ile Gly Ile
        595             600             605

Arg Gln Leu Phe Asn Ser Val His Leu Arg Glu Leu Ser Glu Ala Glu
    610             615             620

Val Arg Arg His Arg Glu Ala Arg Pro Ala Leu Leu Thr Ser Arg Leu
625             630             635             640

Arg Phe Leu Pro Lys Pro Ser Gly Leu Arg Pro Ile Val Asn Met Asp
                645             650             655

Tyr Ile Met Gly Ala Arg Thr Phe His Arg Asp Lys Lys Val Gln His
            660             665             670
```

-continued

```
Leu Thr Ser Gln Leu Lys Thr Leu Phe Ser Val Leu Asn Tyr Glu Arg
            675                 680                 685

Ala Arg Arg Pro Ser Leu Leu Gly Ala Ser Met Leu Gly Met Asp Asp
    690                 695                 700

Ile His Arg Ala Trp Arg Thr Phe Val Leu Arg Ile Arg Ala Gln Asn
705                 710                 715                 720

Pro Ala Pro Gln Leu Tyr Phe Val Lys Val Asp Val Thr Gly Ala Tyr
                    725                 730                 735

Asp Ala Leu Pro Gln Asp Arg Leu Val Glu Val Ile Ala Asn Val Ile
                740                 745                 750

Arg Pro Gln Glu Ser Thr Tyr Cys Val Arg His Tyr Ala Val Val Gln
            755                 760                 765

Arg Thr Ala Arg Gly His Val Arg Lys Ala Phe Lys Arg His Val Ser
    770                 775                 780

Thr Phe Ala Asp Leu Gln Pro Tyr Met Arg Gln Phe Val Glu Arg Leu
785                 790                 795                 800

Gln Glu Thr Ser Leu Leu Arg Asp Ala Val Val Ile Glu Gln Ser Ser
                    805                 810                 815

Ser Leu Asn Glu Ala Gly Ser Ser Leu Phe His Leu Phe Leu Arg Leu
                820                 825                 830

Val His Asn His Val Val Arg Ile Gly Gly Lys Ser Tyr Ile Gln Cys
            835                 840                 845

Gln Gly Val Pro Gln Gly Ser Ile Leu Ser Thr Leu Leu Cys Ser Leu
    850                 855                 860

Cys Tyr Gly Asp Met Glu Arg Arg Leu Phe Pro Gly Ile Glu Gln Asp
865                 870                 875                 880

Gly Val Leu Leu Arg Leu Phe Leu Leu Val Thr Pro His Leu Thr Gln
                    885                 890                 895

Ala Gln Ala Phe Leu Arg Thr Leu Val Lys Gly Val Pro Glu Tyr Gly
                900                 905                 910

Cys Arg Ala Asn Leu Gln Lys Thr Ala Val Asn Phe Pro Val Glu Asp
            915                 920                 925

Gly Ala Leu Gly Ser Ala Ala Pro Leu Gln Leu Pro Ala His Cys Leu
    930                 935                 940

Phe Pro Trp Cys Gly Leu Leu Leu Asp Thr Arg Thr Leu Glu Val Ser
945                 950                 955                 960

Cys Asp Tyr Ser Ser Tyr Ala His Thr Ser Ile Arg Ala Ser Leu Thr
                    965                 970                 975

Phe Ser Gln Gly Ala Lys Pro Gly Arg Asn Met Arg Arg Lys Leu Leu
                980                 985                 990

Ala Val Leu Arg Leu Lys Cys Cys Ala Leu Phe Leu Asp Leu Gln Val
            995                 1000                1005

Asn Gly Ile His Thr Val Tyr Met Asn Val Tyr Lys Ile Phe Leu
    1010                1015                1020

Leu Gln Ala Tyr Arg Phe His Ala Cys Val Leu Gln Leu Pro Phe
    1025                1030                1035

Asn Gln Pro Val Arg Lys Asn Pro Ser Phe Phe Leu Arg Val Ile
    1040                1045                1050

Ala Asp Thr Ala Ser Cys Cys Tyr Ser Leu Leu Lys Ala Arg Asn
    1055                1060                1065

Ala Gly Leu Ser Leu Gly Ala Lys Gly Ala Ser Gly Leu Phe Pro
    1070                1075                1080

Ser Glu Ala Ala Arg Trp Leu Cys Leu His Ala Phe Leu Leu Lys
```

| | | | | | | | | | | | |
|---|---|---|---|---|---|---|---|---|---|---|---|
| | | 1085 | | | | 1090 | | | | 1095 | |
| Leu | Ala | His | His | Ser | Gly | Thr | Tyr | Arg | Cys | Leu | Leu | Gly Ala Leu |

Leu Ala His His Ser Gly Thr Tyr Arg Cys Leu Leu Gly Ala Leu
     1100                       1105                      1110

Gln Ala Ala Lys Ala His Leu Ser Arg Gln Leu Pro Arg Gly Thr
     1115                       1120                      1125

Leu Ala Ala Leu Glu Ala Ala Ala Asp Pro Ser Leu Thr Ala Asp
     1130                       1135                      1140

Phe Lys Thr Ile Leu Asp Thr Glu Leu Lys Leu Ser Asp Tyr Glu
     1145                       1150                      1155

Gly Arg Leu Ile Gln Asn Ser Leu Thr Gly Lys Pro Ile Pro Asn
     1160                       1165                      1170

Pro Leu Leu Gly Leu Asp Ser Thr
     1175                       1180

```
<210> SEQ ID NO 3
<211> LENGTH: 3564
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pCDT plasmid sequence
<220> FEATURE:
<221> NAME/KEY: CDS
<222> LOCATION: (13)..(3552)

<400> SEQUENCE: 3
aagcttgccg cc atg cag att ttc gtc aaa acc ctc acc ggc aag acc atc      51
              Met Gln Ile Phe Val Lys Thr Leu Thr Gly Lys Thr Ile
                1               5                  10 aca ttg gaa gtg gaa ccc agt gat act atc gaa aat gtt aaa gcc aaa       99
Thr Leu Glu Val Glu Pro Ser Asp Thr Ile Glu Asn Val Lys Ala Lys
 15                  20                  25 atc cag gat aag gag ggc att cct cct gac cag cag aga ctt att ttc      147
Ile Gln Asp Lys Glu Gly Ile Pro Pro Asp Gln Gln Arg Leu Ile Phe
 30                  35                  40                  45 gca ggc aaa cag ctg gag gac ggc aga aca ttg tct gac tac aac atc      195
Ala Gly Lys Gln Leu Glu Asp Gly Arg Thr Leu Ser Asp Tyr Asn Ile
                 50                  55                  60 cag aaa gag agc aca ctt cac ttg gtt ctc cgc ctt cgc gga gga cgg      243
Gln Lys Glu Ser Thr Leu His Leu Val Leu Arg Leu Arg Gly Gly Arg
             65                  70                  75 gcc ctc gtg gct cag tgt ctg gtg tgt gtc cca tgg gga gca cgg cct      291
Ala Leu Val Ala Gln Cys Leu Val Cys Val Pro Trp Gly Ala Arg Pro
         80                  85                  90 cca cca gca gcc ccc tgc ttt aga cag gtc agt tgc ctc aag gag ctc      339
Pro Pro Ala Ala Pro Cys Phe Arg Gln Val Ser Cys Leu Lys Glu Leu
     95                 100                 105 gtg gcc agg gtg gtt cag aga ctc tgc gag cgg ggt gcc cgg aac gtc      387
Val Ala Arg Val Val Gln Arg Leu Cys Glu Arg Gly Ala Arg Asn Val
110                 115                 120                 125 ctc gct ttt gga ttc gca ctg ctg gac ggc gct cgg gga ggc cca ccc      435
Leu Ala Phe Gly Phe Ala Leu Leu Asp Gly Ala Arg Gly Gly Pro Pro
                130                 135                 140 gtg gcc ttt aca acc agc gtg cgg tca tac ctg ccc aac act gtg aca      483
Val Ala Phe Thr Thr Ser Val Arg Ser Tyr Leu Pro Asn Thr Val Thr
            145                 150                 155 gag aca ctg aga ggc tcc ggc gct tgg ggc ctt ctg ttg agg cgc gtt      531
Glu Thr Leu Arg Gly Ser Gly Ala Trp Gly Leu Leu Leu Arg Arg Val
        160                 165                 170
```

| | |
|---|---|
| ggc gac gat gtg ttg aca cac ctg ctc gcc agg tgc gca ctt tac ctg<br>Gly Asp Asp Val Leu Thr His Leu Leu Ala Arg Cys Ala Leu Tyr Leu<br>175                           180                     185 | 579 |
| ctg gtg gcc cca agt tgc gcc tac cag gtg tgc gga cct cct ttg tac<br>Leu Val Ala Pro Ser Cys Ala Tyr Gln Val Cys Gly Pro Pro Leu Tyr<br>190                           195                    200                    205 | 627 |
| gac ctc tgt gcc cct gcc tct ttg cca ctg cct gcc cct ggc ctg cct<br>Asp Leu Cys Ala Pro Ala Ser Leu Pro Leu Pro Ala Pro Gly Leu Pro<br>                    210                    215                    220 | 675 |
| gga ctt cct ggt ctg cct ggt ctc ggc gct gga gct ggc gcc tcc gca<br>Gly Leu Pro Gly Leu Pro Gly Leu Gly Ala Gly Ala Gly Ala Ser Ala<br>               225                         230                    235 | 723 |
| gat ctc agg cct acc cgc cag gca cag aat agc gga gcc agg cgc cgc<br>Asp Leu Arg Pro Thr Arg Gln Ala Gln Asn Ser Gly Ala Arg Arg Arg<br>         240                    245                    250 | 771 |
| cgg ggt agc cca ggt tct ggc gtc ccc ctg gct aaa aga cca cgg agg<br>Arg Gly Ser Pro Gly Ser Gly Val Pro Leu Ala Lys Arg Pro Arg Arg<br>255                         260                    265 | 819 |
| tca gtt gct tcc gaa ccc gag cgg ggc gca cat cgc tcc ttt ccc aga<br>Ser Val Ala Ser Glu Pro Glu Arg Gly Ala His Arg Ser Phe Pro Arg<br>270                         275                  280                  285 | 867 |
| gcc cag cag cca cct gtg tct gag gct cca gca gtg aca ccc gct gtg<br>Ala Gln Gln Pro Pro Val Ser Glu Ala Pro Ala Val Thr Pro Ala Val<br>                    290                    295                    300 | 915 |
| gcc gcc agc cct gcc gcc tca tgg gaa gga gga ccc cct gga acc agg<br>Ala Ala Ser Pro Ala Ala Ser Trp Glu Gly Gly Pro Pro Gly Thr Arg<br>               305                         310                    315 | 963 |
| ccc act acc ccc gct tgg cac ccc tac cct gga ccc cag ggc gtc cct<br>Pro Thr Thr Pro Ala Trp His Pro Tyr Pro Gly Pro Gln Gly Val Pro<br>         320                    325                    330 | 1011 |
| cat gat cct gct cac cca gaa acc aag cgg ttc ctg tac tgc agc gga<br>His Asp Pro Ala His Pro Glu Thr Lys Arg Phe Leu Tyr Cys Ser Gly<br>335                         340                  345 | 1059 |
| ggt aga gaa cgc ttg cgc cca agt ttt ctg ctc agc gcc ctg cct cca<br>Gly Arg Glu Arg Leu Arg Pro Ser Phe Leu Leu Ser Ala Leu Pro Pro<br>350                         355                  360                  365 | 1107 |
| act ctt tcc gga gcc cgg aaa ctc gtg gaa acc atc ttt ctc ggt agc<br>Thr Leu Ser Gly Ala Arg Lys Leu Val Glu Thr Ile Phe Leu Gly Ser<br>                    370                    375                    380 | 1155 |
| gct cct cag aaa cca gga gcc gct agg cgg atg cgc aga ctg cct gca<br>Ala Pro Gln Lys Pro Gly Ala Ala Arg Arg Met Arg Arg Leu Pro Ala<br>               385                         390                    395 | 1203 |
| cgc tac tgg cgc atg cgc cca ctc ttt cag gag ctg ctg gga aat cat<br>Arg Tyr Trp Arg Met Arg Pro Leu Phe Gln Glu Leu Leu Gly Asn His<br>         400                    405                    410 | 1251 |
| gca agg tgc ccc tat cgg gct ctg ctt cgg act cac tgt cca ctg aga<br>Ala Arg Cys Pro Tyr Arg Ala Leu Leu Arg Thr His Cys Pro Leu Arg<br>415                         420                  425 | 1299 |
| gct atg gca gca aag gaa gga agt gga aac cag gcc cat aga gga gtc<br>Ala Met Ala Ala Lys Glu Gly Ser Gly Asn Gln Ala His Arg Gly Val<br>430                         435                  440                    445 | 1347 |
| ggt atc tgt cca ctg gag cgc ccc gtt gct gcc ccc cag gaa cag acc<br>Gly Ile Cys Pro Leu Glu Arg Pro Val Ala Ala Pro Gln Glu Gln Thr<br>                    450                    455                    460 | 1395 |
| gat tca acc cgc ctt gtg cag ctc ctg agg cag cac agt agc cca tgg<br>Asp Ser Thr Arg Leu Val Gln Leu Leu Arg Gln His Ser Ser Pro Trp<br>               465                         470                    475 | 1443 |
| cag gtg tat gct ttt ctt cgc gct tgt ctg tgc cgc ctc gtg ccc gcc<br>Gln Val Tyr Ala Phe Leu Arg Ala Cys Leu Cys Arg Leu Val Pro Ala | 1491 |

-continued

```
              480             485             490
ggt ctg tgg ggc agc ggc cac aac aga aga cgc ttt ttg cgg aat gtg    1539
Gly Leu Trp Gly Ser Gly His Asn Arg Arg Arg Phe Leu Arg Asn Val
    495             500             505 aaa aag ttc gtg tcc ctg gga aag cac gct aaa ctg tca ttg cag gag    1587
Lys Lys Phe Val Ser Leu Gly Lys His Ala Lys Leu Ser Leu Gln Glu
510             515             520             525 ctg acc tgg aag atg cgg gtg cag gat tgt gca tgg ctg agg ggc tct    1635
Leu Thr Trp Lys Met Arg Val Gln Asp Cys Ala Trp Leu Arg Gly Ser
                530             535             540 ccc gga gcc cgc tgc gtc cca gcc gcc gaa cac aga cgg cgc gag gag    1683
Pro Gly Ala Arg Cys Val Pro Ala Ala Glu His Arg Arg Arg Glu Glu
            545             550             555 gtg ctc gca aag ctc ttg tgc tgg ctg atg gga acc tac gtg gtc gaa    1731
Val Leu Ala Lys Leu Leu Cys Trp Leu Met Gly Thr Tyr Val Val Glu
        560             565             570 ctg ctg aaa tct ttt ttc tat gtc act gag act aca ttc cag aag aat    1779
Leu Leu Lys Ser Phe Phe Tyr Val Thr Glu Thr Thr Phe Gln Lys Asn
575             580             585 cgc ctg ttc ttt tac cgg aaa agg atc tgg tcc cag ctt cag agc att    1827
Arg Leu Phe Phe Tyr Arg Lys Arg Ile Trp Ser Gln Leu Gln Ser Ile
590             595             600             605 ggc atc cgg cag cat ttt aac tct gtt cac ctg agg gag ctg agc gag    1875
Gly Ile Arg Gln His Phe Asn Ser Val His Leu Arg Glu Leu Ser Glu
                610             615             620 gca gaa gtg agg cgc cat cag gag gcc cgc ccc act ctg ctt acc tcc    1923
Ala Glu Val Arg Arg His Gln Glu Ala Arg Pro Thr Leu Leu Thr Ser
            625             630             635 aag ctg cgg ttc ctg cct aaa cca tca ggt ctg aga ccc att gtc aac    1971
Lys Leu Arg Phe Leu Pro Lys Pro Ser Gly Leu Arg Pro Ile Val Asn
        640             645             650 atg gat tac gtg gtg ggc gcc aga aca ttc aga aga gac aaa aag gtt    2019
Met Asp Tyr Val Val Gly Ala Arg Thr Phe Arg Arg Asp Lys Lys Val
655             660             665 cgg cat ctc acc tca cag gtt aaa aac ctg ttt tct gtt ctg aac tac    2067
Arg His Leu Thr Ser Gln Val Lys Asn Leu Phe Ser Val Leu Asn Tyr
670             675             680             685 gaa agg gcc agg agg cca tca ctg ctg ggt gcc agt gtg ctg gga atg    2115
Glu Arg Ala Arg Arg Pro Ser Leu Leu Gly Ala Ser Val Leu Gly Met
                690             695             700 gac gat att cac aga gtc tgg cgg agc ttc gtg ctt cgg gtg aga gct    2163
Asp Asp Ile His Arg Val Trp Arg Ser Phe Val Leu Arg Val Arg Ala
            705             710             715 cag gac ccc gcc cca cag ttg tat ttt gtc aag gtc gat gtg act ggt    2211
Gln Asp Pro Ala Pro Gln Leu Tyr Phe Val Lys Val Asp Val Thr Gly
        720             725             730 gct tat gac gct ctc cct cag gac aaa ttg gtg gag gtg atc gct aat    2259
Ala Tyr Asp Ala Leu Pro Gln Asp Lys Leu Val Glu Val Ile Ala Asn
735             740             745 gtc atc cgc ccc cag gaa aat aca tac tgc gtg cgg cat tac gct gtg    2307
Val Ile Arg Pro Gln Glu Asn Thr Tyr Cys Val Arg His Tyr Ala Val
750             755             760             765 gtg cag cgc acc gca cag ggc cac gtg agg aaa tcc ttc aag cgg cat    2355
Val Gln Arg Thr Ala Gln Gly His Val Arg Lys Ser Phe Lys Arg His
                770             775             780 gtg tcc acc ttc gtc gac ctc cag cca tat atg cgc cag ttt gtg gag    2403
Val Ser Thr Phe Val Asp Leu Gln Pro Tyr Met Arg Gln Phe Val Glu
            785             790             795 cac ctg cag gaa act tca agc ctt agg gat gcc gtt gtt atc gag cag    2451
```

```
                His Leu Gln Glu Thr Ser Ser Leu Arg Asp Ala Val Ile Glu Gln
                            800                 805                 810 agt tct agt ctc aac gag acc gga cac agt ctc ttc cac ctc ttt ctg           2499
Ser Ser Ser Leu Asn Glu Thr Gly His Ser Leu Phe His Leu Phe Leu
815                 820                 825 agg ctc gtg cat aat cat gtc atc cgc att gga gga aaa tct tat gtt           2547
Arg Leu Val His Asn His Val Ile Arg Ile Gly Gly Lys Ser Tyr Val
830                 835                 840                 845 cag tgc cag ggc atc cct cag ggt tct atc ctg tca act ctg ctc tgc           2595
Gln Cys Gln Gly Ile Pro Gln Gly Ser Ile Leu Ser Thr Leu Leu Cys
                    850                 855                 860 tcc ttg tgt tac ggc gat atg gaa agt agg ctt ttc tca gga atc cag           2643
Ser Leu Cys Tyr Gly Asp Met Glu Ser Arg Leu Phe Ser Gly Ile Gln
                865                 870                 875 cag gac ggc gtc ctg ctg cgg ctg ttt ctt ctg gtg aca cct cac ctg           2691
Gln Asp Gly Val Leu Leu Arg Leu Phe Leu Leu Val Thr Pro His Leu
            880                 885                 890 gca cag gcc cag gcc ttc ctg cgc aca ctg gtg agc gga gtg cct gag           2739
Ala Gln Ala Gln Ala Phe Leu Arg Thr Leu Val Ser Gly Val Pro Glu
        895                 900                 905 tac ggc tgt acc gcc aac ctg cag aag aca gcc gtg aat ttt cca gtg           2787
Tyr Gly Cys Thr Ala Asn Leu Gln Lys Thr Ala Val Asn Phe Pro Val
910                 915                 920                 925 gac acc ggt gct cca ggc tcc gcc gca cct ctg cag ttg ccc gca cat           2835
Asp Thr Gly Ala Pro Gly Ser Ala Ala Pro Leu Gln Leu Pro Ala His
                    930                 935                 940 tgt ctc ttt cct tgg tgt ggc ctg ctc ctc gac acc cgg act ttg gaa           2883
Cys Leu Phe Pro Trp Cys Gly Leu Leu Leu Asp Thr Arg Thr Leu Glu
                945                 950                 955 gtc ttt tgc gat tac tcc agc tat gca cag aca tcc att agg agc agc           2931
Val Phe Cys Asp Tyr Ser Ser Tyr Ala Gln Thr Ser Ile Arg Ser Ser
            960                 965                 970 ctg aca ttc agc cag ggc aca cgg ccc ggc cgc aat atg agg aga aag           2979
Leu Thr Phe Ser Gln Gly Thr Arg Pro Gly Arg Asn Met Arg Arg Lys
        975                 980                 985 ttg ctc gcc gtt atg aga ctc aag tgc tgt gca gtc ttt ctt gat ctg           3027
Leu Leu Ala Val Met Arg Leu Lys Cys Cys Ala Val Phe Leu Asp Leu
990                 995                 1000                1005 cag gtc aat tct att cat acc gtt tac acc aac atc tat aaa att               3072
Gln Val Asn Ser Ile His Thr Val Tyr Thr Asn Ile Tyr Lys Ile
                    1010                1015                1020 ttc ctg ctc cag gca tat aga ttt cac gcc tgc gtg ttg cag ttc               3117
Phe Leu Leu Gln Ala Tyr Arg Phe His Ala Cys Val Leu Gln Phe
                1025                1030                1035 cca ttc aat cag ccc gtt cgg aag aac ccc agt ttc ttt ctc agg               3162
Pro Phe Asn Gln Pro Val Arg Lys Asn Pro Ser Phe Phe Leu Arg
            1040                1045                1050 gtt att gct gat acc gcc tcc cgc tgt tac tcc ctg ctt aag gcc               3207
Val Ile Ala Asp Thr Ala Ser Arg Cys Tyr Ser Leu Leu Lys Ala
        1055                1060                1065 aag aac aca gga ctt tca ttg ggt gct aaa ggc gcc agt gga cct               3252
Lys Asn Thr Gly Leu Ser Leu Gly Ala Lys Gly Ala Ser Gly Pro
    1070                1075                1080 ttc cct tct gaa gcc gct cgg tgg ctc tgt ttg cac gca ttc ctt               3297
Phe Pro Ser Glu Ala Ala Arg Trp Leu Cys Leu His Ala Phe Leu
                1085                1090                1095 ctg aag ttg gct aga cac agc tct act tac aga tgc ctt ctg ggc               3342
Leu Lys Leu Ala Arg His Ser Ser Thr Tyr Arg Cys Leu Leu Gly
                1100                1105                1110
```

| | | | | | | | | | | | | | | |
|---|---|---|---|---|---|---|---|---|---|---|---|---|---|---|
| ccc | ctt | aga | gct | gct | aag | gct | cat | ctg | tca | aga | cag | ctc | cca | aga | 3387 |
| Pro | Leu | Arg | Ala | Ala | Lys | Ala | His | Leu | Ser | Arg | Gln | Leu | Pro | Arg | |
| | | | 1115 | | | | | 1120 | | | | | 1125 | | |
| ggc | act | ctc | gcc | gca | ctg | gag | gcc | gca | gcc | gac | ccc | tcc | ctc | act | 3432 |
| Gly | Thr | Leu | Ala | Ala | Leu | Glu | Ala | Ala | Ala | Asp | Pro | Ser | Leu | Thr | |
| | 1130 | | | | | | 1135 | | | | | | 1140 | | |
| gca | gat | ttt | aag | act | att | ctc | gat | acc | gag | ctt | aag | ttg | tca | gac | 3477 |
| Ala | Asp | Phe | Lys | Thr | Ile | Leu | Asp | Thr | Glu | Leu | Lys | Leu | Ser | Asp | |
| | | | 1145 | | | | | 1150 | | | | | 1155 | | |
| tac | gag | gga | cgc | ctg | att | cag | aat | agc | ctg | aca | ggc | aaa | ccc | att | 3522 |
| Tyr | Glu | Gly | Arg | Leu | Ile | Gln | Asn | Ser | Leu | Thr | Gly | Lys | Pro | Ile | |
| | 1160 | | | | | | 1165 | | | | | | 1170 | | |
| cct | aat | ccc | ctg | ttg | ggt | ttg | gat | tcc | aca | tgataatcta | ga | | | | 3564 |
| Pro | Asn | Pro | Leu | Leu | Gly | Leu | Asp | Ser | Thr | | | | | | |
| | | 1175 | | | | | | 1180 | | | | | | | |

<210> SEQ ID NO 4
<211> LENGTH: 1180
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Arg Ala Leu Val
65                  70                  75                  80

Ala Gln Cys Leu Val Cys Val Pro Trp Gly Ala Arg Pro Pro Pro Ala
                85                  90                  95

Ala Pro Cys Phe Arg Gln Val Ser Cys Leu Lys Glu Leu Val Ala Arg
            100                 105                 110

Val Val Gln Arg Leu Cys Glu Arg Gly Ala Arg Asn Val Leu Ala Phe
        115                 120                 125

Gly Phe Ala Leu Leu Asp Gly Ala Arg Gly Gly Pro Pro Val Ala Phe
    130                 135                 140

Thr Thr Ser Val Arg Ser Tyr Leu Pro Asn Thr Val Thr Glu Thr Leu
145                 150                 155                 160

Arg Gly Ser Gly Ala Trp Gly Leu Leu Leu Arg Arg Val Gly Asp Asp
                165                 170                 175

Val Leu Thr His Leu Leu Ala Arg Cys Ala Leu Tyr Leu Leu Val Ala
            180                 185                 190

Pro Ser Cys Ala Tyr Gln Val Cys Gly Pro Pro Leu Tyr Asp Leu Cys
        195                 200                 205

Ala Pro Ala Ser Leu Pro Leu Pro Ala Pro Gly Leu Pro Gly Leu Pro
    210                 215                 220

Gly Leu Pro Gly Leu Gly Ala Gly Ala Gly Ala Ser Ala Asp Leu Arg
225                 230                 235                 240

Pro Thr Arg Gln Ala Gln Asn Ser Gly Ala Arg Arg Arg Gly Ser
                245                 250                 255
```

-continued

```
Pro Gly Ser Gly Val Pro Leu Ala Lys Arg Pro Arg Ser Val Ala
            260                 265                 270

Ser Glu Pro Glu Arg Gly Ala His Arg Ser Phe Pro Arg Ala Gln Gln
        275                 280                 285

Pro Pro Val Ser Glu Ala Pro Ala Val Thr Pro Ala Val Ala Ala Ser
    290                 295                 300

Pro Ala Ala Ser Trp Glu Gly Gly Pro Pro Gly Thr Arg Pro Thr Thr
305                 310                 315                 320

Pro Ala Trp His Pro Tyr Pro Gly Pro Gln Gly Val Pro His Asp Pro
                325                 330                 335

Ala His Pro Glu Thr Lys Arg Phe Leu Tyr Cys Ser Gly Gly Arg Glu
            340                 345                 350

Arg Leu Arg Pro Ser Phe Leu Leu Ser Ala Leu Pro Pro Thr Leu Ser
        355                 360                 365

Gly Ala Arg Lys Leu Val Glu Thr Ile Phe Leu Gly Ser Ala Pro Gln
    370                 375                 380

Lys Pro Gly Ala Ala Arg Arg Met Arg Arg Leu Pro Ala Arg Tyr Trp
385                 390                 395                 400

Arg Met Arg Pro Leu Phe Gln Glu Leu Leu Gly Asn His Ala Arg Cys
                405                 410                 415

Pro Tyr Arg Ala Leu Leu Arg Thr His Cys Pro Leu Arg Ala Met Ala
            420                 425                 430

Ala Lys Glu Gly Ser Gly Asn Gln Ala His Arg Gly Val Gly Ile Cys
        435                 440                 445

Pro Leu Glu Arg Pro Val Ala Pro Gln Gln Thr Asp Ser Thr
    450                 455                 460

Arg Leu Val Gln Leu Leu Arg Gln His Ser Ser Pro Trp Gln Val Tyr
465                 470                 475                 480

Ala Phe Leu Arg Ala Cys Leu Cys Arg Leu Val Pro Ala Gly Leu Trp
                485                 490                 495

Gly Ser Gly His Asn Arg Arg Phe Leu Arg Asn Val Lys Lys Phe
            500                 505                 510

Val Ser Leu Gly Lys His Ala Lys Leu Ser Leu Gln Glu Leu Thr Trp
        515                 520                 525

Lys Met Arg Val Gln Asp Cys Ala Trp Leu Arg Gly Ser Pro Gly Ala
    530                 535                 540

Arg Cys Val Pro Ala Ala Glu His Arg Arg Glu Glu Val Leu Ala
545                 550                 555                 560

Lys Leu Leu Cys Trp Leu Met Gly Thr Tyr Val Val Glu Leu Leu Lys
                565                 570                 575

Ser Phe Phe Tyr Val Thr Glu Thr Thr Phe Gln Lys Asn Arg Leu Phe
            580                 585                 590

Phe Tyr Arg Lys Arg Ile Trp Ser Gln Leu Gln Ser Ile Gly Ile Arg
        595                 600                 605

Gln His Phe Asn Ser Val His Leu Arg Glu Leu Ser Glu Ala Glu Val
    610                 615                 620

Arg Arg His Gln Glu Ala Arg Pro Thr Leu Leu Thr Ser Lys Leu Arg
625                 630                 635                 640

Phe Leu Pro Lys Pro Ser Gly Leu Arg Pro Ile Val Asn Met Asp Tyr
                645                 650                 655

Val Val Gly Ala Arg Thr Phe Arg Arg Asp Lys Lys Val Arg His Leu
            660                 665                 670

Thr Ser Gln Val Lys Asn Leu Phe Ser Val Leu Asn Tyr Glu Arg Ala
```

```
                675                 680                 685
Arg Arg Pro Ser Leu Leu Gly Ala Ser Val Leu Gly Met Asp Asp Ile
    690                 695                 700
His Arg Val Trp Arg Ser Phe Val Leu Arg Val Arg Ala Gln Asp Pro
705                 710                 715                 720
Ala Pro Gln Leu Tyr Phe Val Lys Val Asp Val Thr Gly Ala Tyr Asp
                725                 730                 735
Ala Leu Pro Gln Asp Lys Leu Val Glu Val Ile Ala Asn Val Ile Arg
            740                 745                 750
Pro Gln Glu Asn Thr Tyr Cys Val Arg His Tyr Ala Val Val Gln Arg
        755                 760                 765
Thr Ala Gln Gly His Val Arg Lys Ser Phe Lys Arg His Val Ser Thr
    770                 775                 780
Phe Val Asp Leu Gln Pro Tyr Met Arg Gln Phe Val Glu His Leu Gln
785                 790                 795                 800
Glu Thr Ser Ser Leu Arg Asp Ala Val Val Ile Glu Gln Ser Ser Ser
                805                 810                 815
Leu Asn Glu Thr Gly His Ser Leu Phe His Leu Phe Leu Arg Leu Val
            820                 825                 830
His Asn His Val Ile Arg Ile Gly Gly Lys Ser Tyr Val Gln Cys Gln
        835                 840                 845
Gly Ile Pro Gln Gly Ser Ile Leu Ser Thr Leu Leu Cys Ser Leu Cys
    850                 855                 860
Tyr Gly Asp Met Glu Ser Arg Leu Phe Ser Gly Ile Gln Gln Asp Gly
865                 870                 875                 880
Val Leu Leu Arg Leu Phe Leu Leu Val Thr Pro His Leu Ala Gln Ala
                885                 890                 895
Gln Ala Phe Leu Arg Thr Leu Val Ser Gly Val Pro Glu Tyr Gly Cys
            900                 905                 910
Thr Ala Asn Leu Gln Lys Thr Ala Val Asn Phe Pro Val Asp Thr Gly
        915                 920                 925
Ala Pro Gly Ser Ala Ala Pro Leu Gln Leu Pro Ala His Cys Leu Phe
    930                 935                 940
Pro Trp Cys Gly Leu Leu Leu Asp Thr Arg Thr Leu Glu Val Phe Cys
945                 950                 955                 960
Asp Tyr Ser Ser Tyr Ala Gln Thr Ser Ile Arg Ser Ser Leu Thr Phe
                965                 970                 975
Ser Gln Gly Thr Arg Pro Gly Arg Asn Met Arg Arg Lys Leu Leu Ala
            980                 985                 990
Val Met Arg Leu Lys Cys Cys Ala Val Phe Leu Asp Leu Gln Val Asn
        995                 1000                1005
Ser Ile His Thr Val Tyr Thr Asn Ile Tyr Lys Ile Phe Leu Leu
    1010                1015                1020
Gln Ala Tyr Arg Phe His Ala Cys Val Leu Gln Phe Pro Phe Asn
    1025                1030                1035
Gln Pro Val Arg Lys Asn Pro Ser Phe Phe Leu Arg Val Ile Ala
    1040                1045                1050
Asp Thr Ala Ser Arg Cys Tyr Ser Leu Leu Lys Ala Lys Asn Thr
    1055                1060                1065
Gly Leu Ser Leu Gly Ala Lys Gly Ala Ser Gly Pro Phe Pro Ser
    1070                1075                1080
Glu Ala Ala Arg Trp Leu Cys Leu His Ala Phe Leu Leu Lys Leu
    1085                1090                1095
```

Ala Arg His Ser Ser Thr Tyr Arg Cys Leu Leu Gly Pro Leu Arg
    1100            1105            1110

Ala Ala Lys Ala His Leu Ser Arg Gln Leu Pro Arg Gly Thr Leu
    1115            1120            1125

Ala Ala Leu Glu Ala Ala Ala Asp Pro Ser Leu Thr Ala Asp Phe
    1130            1135            1140

Lys Thr Ile Leu Asp Thr Glu Leu Lys Leu Ser Asp Tyr Glu Gly
    1145            1150            1155

Arg Leu Ile Gln Asn Ser Leu Thr Gly Lys Pro Ile Pro Asn Pro
    1160            1165            1170

Leu Leu Gly Leu Asp Ser Thr
    1175            1180

<210> SEQ ID NO 5
<211> LENGTH: 1123
<212> TYPE: PRT
<213> ORGANISM: Canis familiaris

<400> SEQUENCE: 5

Met Pro Arg Ala Pro Arg Cys Arg Ala Val Arg Ala Leu Leu Arg Gly
1               5                   10                  15

Arg Tyr Arg Glu Val Leu Pro Leu Ala Thr Phe Leu Arg Arg Leu Gly
            20                  25                  30

Pro Pro Gly Arg Leu Leu Val Arg Gly Asp Pro Ala Ala Phe Arg
            35                  40                  45

Ala Leu Val Ala Gln Cys Leu Val Cys Val Pro Trp Gly Ala Arg Pro
    50                  55                  60

Pro Pro Ala Ala Pro Cys Phe Arg Gln Val Ser Cys Leu Lys Glu Leu
65                  70                  75                  80

Val Ala Arg Val Val Gln Arg Leu Cys Glu Arg Gly Ala Arg Asn Val
                85                  90                  95

Leu Ala Phe Gly Phe Ala Leu Leu Asp Gly Ala Arg Gly Gly Pro Pro
            100                 105                 110

Val Ala Phe Thr Thr Ser Val Arg Ser Tyr Leu Pro Asn Thr Val Thr
        115                 120                 125

Glu Thr Leu Arg Gly Ser Gly Ala Trp Gly Leu Leu Leu Arg Arg Val
    130                 135                 140

Gly Asp Asp Val Leu Thr His Leu Leu Ala Arg Cys Ala Leu Tyr Leu
145                 150                 155                 160

Leu Val Ala Pro Ser Cys Ala Tyr Gln Val Cys Gly Pro Pro Leu Tyr
                165                 170                 175

Asp Leu Cys Ala Pro Ala Ser Leu Pro Leu Pro Ala Pro Gly Leu Pro
            180                 185                 190

Gly Leu Pro Gly Leu Pro Gly Leu Gly Ala Gly Ala Gly Ala Ser Ala
        195                 200                 205

Asp Leu Arg Pro Thr Arg Gln Ala Gln Asn Ser Gly Ala Arg Arg Arg
    210                 215                 220

Arg Gly Ser Pro Gly Ser Gly Val Pro Leu Ala Lys Arg Pro Arg Arg
225                 230                 235                 240

Ser Val Ala Ser Glu Pro Glu Arg Gly Ala His Arg Ser Phe Pro Arg
                245                 250                 255

Ala Gln Gln Pro Pro Val Ser Glu Ala Pro Ala Val Thr Pro Ala Val
            260                 265                 270

Ala Ala Ser Pro Ala Ala Ser Trp Glu Gly Gly Pro Pro Gly Thr Arg

-continued

```
            275                 280                 285
Pro Thr Thr Pro Ala Trp His Pro Tyr Pro Gly Pro Gln Gly Val Pro
290                 295                 300
His Asp Pro Ala His Pro Glu Thr Lys Arg Phe Leu Tyr Cys Ser Gly
305                 310                 315                 320
Gly Arg Glu Arg Leu Arg Pro Ser Phe Leu Leu Ser Ala Leu Pro Pro
                325                 330                 335
Thr Leu Ser Gly Ala Arg Lys Leu Val Glu Thr Ile Phe Leu Gly Ser
                340                 345                 350
Ala Pro Gln Lys Pro Gly Ala Ala Arg Arg Met Arg Arg Leu Pro Ala
                355                 360                 365
Arg Tyr Trp Arg Met Arg Pro Leu Phe Gln Glu Leu Leu Gly Asn His
370                 375                 380
Ala Arg Cys Pro Tyr Arg Ala Leu Leu Arg Thr His Cys Pro Leu Arg
385                 390                 395                 400
Ala Met Ala Ala Lys Glu Gly Ser Gly Asn Gln Ala His Arg Gly Val
                405                 410                 415
Gly Ile Cys Pro Leu Glu Arg Pro Val Ala Ala Pro Gln Glu Gln Thr
                420                 425                 430
Asp Ser Thr Arg Leu Val Gln Leu Leu Arg Gln His Ser Ser Pro Trp
                435                 440                 445
Gln Val Tyr Ala Phe Leu Arg Ala Cys Leu Cys Trp Leu Val Pro Thr
                450                 455                 460
Gly Leu Trp Gly Ser Arg His Asn Gln Arg Arg Phe Leu Arg Asn Val
465                 470                 475                 480
Lys Lys Phe Ile Ser Leu Gly Lys His Ala Lys Leu Ser Leu Gln Glu
                485                 490                 495
Leu Thr Trp Lys Met Lys Val Arg Asp Cys Thr Trp Leu His Gly Asn
                500                 505                 510
Pro Gly Ala Cys Cys Val Pro Ala Ala Glu His Arg Arg Arg Glu Glu
                515                 520                 525
Ile Leu Ala Arg Phe Leu Val Leu Val Asp Gly His Ile Tyr Val Val
530                 535                 540
Lys Leu Leu Arg Ser Phe Phe Tyr Val Thr Glu Thr Thr Phe Gln Lys
545                 550                 555                 560
Asn Arg Leu Phe Phe Tyr Arg Lys Ser Val Trp Ser Gln Leu Gln Ser
                565                 570                 575
Ile Gly Ile Arg Gln Leu Phe Asn Ser Val His Leu Arg Glu Leu Ser
                580                 585                 590
Glu Ala Glu Val Arg Arg His Arg Glu Ala Arg Pro Ala Leu Leu Thr
                595                 600                 605
Ser Arg Leu Arg Phe Leu Pro Lys Pro Ser Gly Leu Arg Pro Ile Val
                610                 615                 620
Asn Met Asp Tyr Ile Met Gly Ala Arg Thr Phe His Arg Asp Lys Lys
625                 630                 635                 640
Val Gln His Leu Thr Ser Gln Leu Lys Thr Leu Phe Ser Val Leu Asn
                645                 650                 655
Tyr Glu Arg Ala Arg Arg Pro Ser Leu Leu Gly Ala Ser Met Leu Gly
                660                 665                 670
Met Asp Asp Ile His Arg Ala Trp Arg Thr Phe Val Leu Arg Ile Arg
                675                 680                 685
Ala Gln Asn Pro Ala Pro Gln Leu Tyr Phe Val Lys Val Asp Val Thr
690                 695                 700
```

```
Gly Ala Tyr Asp Ala Leu Pro Gln Asp Arg Leu Val Glu Val Ile Ala
705                 710                 715                 720

Asn Val Ile Arg Pro Gln Glu Ser Thr Tyr Cys Val Arg His Tyr Ala
            725                 730                 735

Val Val Gln Arg Thr Ala Arg Gly His Val Arg Lys Ala Phe Lys Arg
        740                 745                 750

His Val Ser Thr Phe Ala Asp Leu Gln Pro Tyr Met Arg Gln Phe Val
    755                 760                 765

Glu Arg Leu Gln Glu Thr Ser Leu Leu Arg Asp Ala Val Val Ile Glu
770                 775                 780

Gln Ser Ser Ser Leu Asn Glu Ala Gly Ser Ser Leu Phe His Leu Phe
785                 790                 795                 800

Leu Arg Leu Val His Asn His Val Val Arg Ile Gly Gly Lys Ser Tyr
                805                 810                 815

Ile Gln Cys Gln Gly Val Pro Gln Gly Ser Ile Leu Ser Thr Leu Leu
        820                 825                 830

Cys Ser Leu Cys Tyr Gly Asp Met Glu Arg Arg Leu Phe Pro Gly Ile
        835                 840                 845

Glu Gln Asp Gly Val Leu Leu Arg Leu Val Asp Asp Phe Leu Leu Val
850                 855                 860

Thr Pro His Leu Thr Gln Ala Gln Ala Phe Leu Arg Thr Leu Val Lys
865                 870                 875                 880

Gly Val Pro Glu Tyr Gly Cys Arg Ala Asn Leu Gln Lys Thr Ala Val
                885                 890                 895

Asn Phe Pro Val Glu Asp Gly Ala Leu Gly Ser Ala Ala Pro Leu Gln
            900                 905                 910

Leu Pro Ala His Cys Leu Phe Pro Trp Cys Gly Leu Leu Leu Asp Thr
        915                 920                 925

Arg Thr Leu Glu Val Ser Cys Asp Tyr Ser Ser Tyr Ala His Thr Ser
930                 935                 940

Ile Arg Ala Ser Leu Thr Phe Ser Gln Gly Ala Lys Pro Gly Arg Asn
945                 950                 955                 960

Met Arg Arg Lys Leu Leu Ala Val Leu Arg Leu Lys Cys Cys Ala Leu
                965                 970                 975

Phe Leu Asp Leu Gln Val Asn Gly Ile His Thr Val Tyr Met Asn Val
            980                 985                 990

Tyr Lys Ile Phe Leu Leu Gln Ala  Tyr Arg Phe His Ala  Cys Val Leu
        995                 1000                1005

Gln Leu  Pro Phe Asn Gln Pro  Val Arg Lys Asn Pro  Ser Phe Phe
    1010                1015                1020

Leu Arg  Val Ile Ala Asp Thr  Ala Ser Cys Cys Tyr  Ser Leu Leu
    1025                1030                1035

Lys Ala  Arg Asn Ala Gly Leu  Ser Leu Gly Ala Lys  Gly Ala Ser
    1040                1045                1050

Gly Leu  Phe Pro Ser Glu Ala  Ala Arg Trp Leu Cys  Leu His Ala
    1055                1060                1065

Phe Leu  Leu Lys Leu Ala His  His Ser Gly Thr Tyr  Arg Cys Leu
    1070                1075                1080

Leu Gly  Ala Leu Gln Ala Ala  Lys Ala His Leu Ser  Arg Gln Leu
    1085                1090                1095

Pro Arg  Gly Thr Leu Ala Ala  Leu Glu Ala Ala  Asp Pro Ser
    1100                1105                1110
```

```
Leu Thr Ala Asp Phe Lys Thr Ile Leu Asp
    1115                1120
```

<210> SEQ ID NO 6
<211> LENGTH: 1073
<212> TYPE: PRT
<213> ORGANISM: Canis familiaris

<400> SEQUENCE: 6

```
Arg Ala Leu Val Ala Gln Cys Leu Val Cys Val Pro Trp Gly Ala Arg
1               5                   10                  15

Pro Pro Pro Ala Ala Pro Cys Phe Arg Gln Val Ser Cys Leu Lys Glu
            20                  25                  30

Leu Val Ala Arg Val Val Gln Arg Leu Cys Glu Arg Gly Ala Arg Asn
        35                  40                  45

Val Leu Ala Phe Gly Phe Ala Leu Leu Asp Gly Ala Arg Gly Gly Pro
    50                  55                  60

Pro Val Ala Phe Thr Thr Ser Val Arg Ser Tyr Leu Pro Asn Thr Val
65                  70                  75                  80

Thr Glu Thr Leu Arg Gly Ser Gly Ala Trp Gly Leu Leu Arg Arg
                85                  90                  95

Val Gly Asp Asp Val Leu Thr His Leu Leu Ala Arg Cys Ala Leu Tyr
            100                 105                 110

Leu Leu Val Ala Pro Ser Cys Ala Tyr Gln Val Cys Gly Pro Pro Leu
        115                 120                 125

Tyr Asp Leu Cys Ala Pro Ala Ser Leu Pro Leu Pro Ala Pro Gly Leu
    130                 135                 140

Pro Gly Leu Pro Gly Leu Pro Gly Leu Gly Ala Gly Ala Gly Ala Ser
145                 150                 155                 160

Ala Asp Leu Arg Pro Thr Arg Gln Ala Gln Asn Ser Gly Ala Arg Arg
                165                 170                 175

Arg Arg Gly Ser Pro Gly Ser Gly Val Pro Leu Ala Lys Arg Pro Arg
            180                 185                 190

Arg Ser Val Ala Ser Glu Pro Glu Arg Gly Ala His Arg Ser Phe Pro
        195                 200                 205

Arg Ala Gln Gln Pro Pro Val Ser Glu Ala Pro Ala Val Thr Pro Ala
    210                 215                 220

Val Ala Ala Ser Pro Ala Ala Ser Trp Glu Gly Gly Pro Pro Gly Thr
225                 230                 235                 240

Arg Pro Thr Thr Pro Ala Trp His Pro Tyr Pro Gly Pro Gln Gly Val
                245                 250                 255

Pro His Asp Pro Ala His Pro Glu Thr Lys Arg Phe Leu Tyr Cys Ser
            260                 265                 270

Gly Gly Arg Glu Arg Leu Arg Pro Ser Phe Leu Leu Ser Ala Leu Pro
        275                 280                 285

Pro Thr Leu Ser Gly Ala Arg Lys Leu Val Glu Thr Ile Phe Leu Gly
    290                 295                 300

Ser Ala Pro Gln Lys Pro Gly Ala Ala Arg Met Arg Arg Leu Pro
305                 310                 315                 320

Ala Arg Tyr Trp Arg Met Arg Pro Leu Phe Gln Glu Leu Leu Gly Asn
                325                 330                 335

His Ala Arg Cys Pro Tyr Arg Ala Leu Leu Arg Thr His Cys Pro Leu
            340                 345                 350

Arg Ala Met Ala Ala Lys Glu Gly Ser Gly Asn Gln Ala His Arg Gly
        355                 360                 365
```

```
Val Gly Ile Cys Pro Leu Glu Arg Pro Val Ala Ala Pro Gln Glu Gln
        370                 375                 380

Thr Asp Ser Thr Arg Leu Val Gln Leu Leu Arg Gln His Ser Ser Pro
385                 390                 395                 400

Trp Gln Val Tyr Ala Phe Leu Arg Ala Cys Leu Cys Trp Leu Val Pro
                405                 410                 415

Thr Gly Leu Trp Gly Ser Arg His Asn Gln Arg Arg Phe Leu Arg Asn
                420                 425                 430

Val Lys Lys Phe Ile Ser Leu Gly Lys His Ala Lys Leu Ser Leu Gln
        435                 440                 445

Glu Leu Thr Trp Lys Met Lys Val Arg Asp Cys Thr Trp Leu His Gly
450                 455                 460

Asn Pro Gly Ala Cys Cys Val Pro Ala Ala Glu His Arg Arg Arg Glu
465                 470                 475                 480

Glu Ile Leu Ala Arg Phe Leu Val Leu Val Asp Gly His Ile Tyr Val
                485                 490                 495

Val Lys Leu Leu Arg Ser Phe Phe Tyr Val Thr Glu Thr Thr Phe Gln
        500                 505                 510

Lys Asn Arg Leu Phe Phe Tyr Arg Lys Ser Val Trp Ser Gln Leu Gln
        515                 520                 525

Ser Ile Gly Ile Arg Gln Leu Phe Asn Ser Val His Leu Arg Glu Leu
530                 535                 540

Ser Glu Ala Glu Val Arg Arg His Arg Glu Ala Arg Pro Ala Leu Leu
545                 550                 555                 560

Thr Ser Arg Leu Arg Phe Leu Pro Lys Pro Ser Gly Leu Arg Pro Ile
                565                 570                 575

Val Asn Met Asp Tyr Ile Met Gly Ala Arg Thr Phe Arg His Arg Asp Lys
        580                 585                 590

Lys Val Gln His Leu Thr Ser Gln Leu Lys Thr Leu Phe Ser Val Leu
        595                 600                 605

Asn Tyr Glu Arg Ala Arg Arg Pro Ser Leu Leu Gly Ala Ser Met Leu
610                 615                 620

Gly Met Asp Asp Ile His Arg Ala Trp Arg Thr Phe Val Leu Arg Ile
625                 630                 635                 640

Arg Ala Gln Asn Pro Ala Pro Gln Leu Tyr Phe Val Lys Val Asp Val
                645                 650                 655

Thr Gly Ala Tyr Asp Ala Leu Pro Gln Asp Arg Leu Val Glu Val Ile
                660                 665                 670

Ala Asn Val Ile Arg Pro Gln Glu Ser Thr Tyr Cys Val Arg His Tyr
        675                 680                 685

Ala Val Val Gln Arg Thr Ala Arg Gly His Val Arg Lys Ala Phe Lys
        690                 695                 700

Arg His Val Ser Thr Phe Ala Asp Leu Gln Pro Tyr Met Arg Gln Phe
705                 710                 715                 720

Val Glu Arg Leu Gln Glu Thr Ser Leu Leu Arg Asp Ala Val Val Ile
                725                 730                 735

Glu Gln Ser Ser Ser Leu Asn Glu Ala Gly Ser Ser Leu Phe His Leu
                740                 745                 750

Phe Leu Arg Leu Val His Asn His Val Val Arg Ile Gly Gly Lys Ser
        755                 760                 765

Tyr Ile Gln Cys Gln Gly Val Pro Gln Gly Ser Ile Leu Ser Thr Leu
        770                 775                 780
```

-continued

Leu Cys Ser Leu Cys Tyr Gly Asp Met Glu Arg Leu Phe Pro Gly
785                 790                 795                 800

Ile Glu Gln Asp Gly Val Leu Leu Arg Leu Phe Leu Leu Val Thr Pro
                805                 810                 815

His Leu Thr Gln Ala Gln Ala Phe Leu Arg Thr Leu Val Lys Gly Val
            820                 825                 830

Pro Glu Tyr Gly Cys Arg Ala Asn Leu Gln Lys Thr Ala Val Asn Phe
        835                 840                 845

Pro Val Glu Asp Gly Ala Leu Gly Ser Ala Ala Pro Leu Gln Leu Pro
    850                 855                 860

Ala His Cys Leu Phe Pro Trp Cys Gly Leu Leu Leu Asp Thr Arg Thr
865                 870                 875                 880

Leu Glu Val Ser Cys Asp Tyr Ser Ser Tyr Ala His Thr Ser Ile Arg
                885                 890                 895

Ala Ser Leu Thr Phe Ser Gln Gly Ala Lys Pro Gly Arg Asn Met Arg
            900                 905                 910

Arg Lys Leu Leu Ala Val Leu Arg Leu Lys Cys Cys Ala Leu Phe Leu
        915                 920                 925

Asp Leu Gln Val Asn Gly Ile His Thr Val Tyr Met Asn Val Tyr Lys
    930                 935                 940

Ile Phe Leu Leu Gln Ala Tyr Arg Phe His Ala Cys Val Leu Gln Leu
945                 950                 955                 960

Pro Phe Asn Gln Pro Val Arg Lys Asn Pro Ser Phe Phe Leu Arg Val
                965                 970                 975

Ile Ala Asp Thr Ala Ser Cys Cys Tyr Ser Leu Leu Lys Ala Arg Asn
            980                 985                 990

Ala Gly Leu Ser Leu Gly Ala Lys  Gly Ala Ser Gly Leu  Phe Pro Ser
        995                 1000                1005

Glu Ala  Ala Arg Trp Leu Cys  Leu His Ala Phe Leu  Leu Lys Leu
    1010                1015                1020

Ala His  His Ser Gly Thr Tyr  Arg Cys Leu Leu Gly  Ala Leu Gln
    1025                1030                1035

Ala Ala  Lys Ala His Leu Ser  Arg Gln Leu Pro Arg  Gly Thr Leu
    1040                1045                1050

Ala Ala  Leu Glu Ala Ala Ala  Asp Pro Ser Leu Thr  Ala Asp Phe
    1055                1060                1065

Lys Thr  Ile Leu Asp
    1070

<210> SEQ ID NO 7
<211> LENGTH: 1024
<212> TYPE: PRT
<213> ORGANISM: Felis catus

<400> SEQUENCE: 7

Asn Val Leu Ala Phe Gly Phe Ala Leu Leu Asp Gly Ala Arg Gly Gly
1               5                   10                  15

Pro Pro Val Val Phe Thr Thr Ser Val Arg Ser Tyr Leu Pro Asn Thr
                20                  25                  30

Val Thr Glu Thr Leu Arg Gly Ser Gly Ala Trp Gly Leu Leu Leu Arg
            35                  40                  45

Arg Val Gly Asp Asp Val Leu Ala His Leu Leu Thr Arg Cys Ala Leu
        50                  55                  60

Tyr Val Leu Val Ala Pro Ser Cys Ala Tyr Gln Val Cys Gly Pro Pro
65                  70                  75                  80

```
Leu Tyr Asp Leu Cys Ala Pro Ala Ala Thr Arg Pro Leu Ala Thr Ser
                85                  90                  95

Gly His Arg Pro Gly Thr Arg Met Asp Leu Arg Pro Thr Arg Gln Ala
            100                 105                 110

Arg Asn Ala Gly Ala Arg Arg Arg Gly Ala Gly Ser Ser Pro
        115                 120                 125

Pro Leu Ala Lys Arg Pro Arg His Asp Val Lys Thr Pro Glu Pro Glu
130                 135                 140

Arg Gly Pro Ala Ser Pro Ser Ser Arg His Pro Pro Gly Arg Ala His
145                 150                 155                 160

Gly Leu Ser Gly Gly Glu Pro Gly Ala Val Thr Ser Ala Arg Ala Ala
                165                 170                 175

Ala Glu Ala Asn Ser Gly Glu Gly Gly Pro Gly Thr Arg Leu Thr
            180                 185                 190

Ser Ala Gly Ala Gln Leu Ser Arg Pro Gln Gly Val Pro Leu Ser His
        195                 200                 205

Leu Ser His Pro Glu Thr Lys His Phe Leu Tyr Cys Pro Gly Gly Lys
210                 215                 220

Glu Arg Leu Arg Pro Ser Phe Leu Leu Ser Ala Leu Arg Pro Ser Leu
225                 230                 235                 240

Thr Gly Ala Arg Thr Leu Leu Glu Ala Ile Phe Leu Gly Ser Lys Ser
                245                 250                 255

Pro Arg Pro Gly Ala Ala Arg Arg Thr Arg Arg Leu Pro Ala Arg Tyr
                260                 265                 270

Trp Arg Met Arg Pro Leu Phe Arg Glu Leu Leu Ala Asn His Ala Arg
            275                 280                 285

Cys Pro Tyr Asp Ala Leu Leu Arg Thr His Cys Pro Leu Arg Ala Pro
        290                 295                 300

Ala Pro Ala Glu Gly Ser Ser Arg Gly Val Gly Gly Ala Gly Gly
305                 310                 315                 320

Cys Ala Leu Gly Arg Pro Gly Ala Pro Gln Glu Gln Thr Asp Ser
                325                 330                 335

Thr Arg Leu Val Gln Leu Leu Arg Gln His Ser Ser Pro Trp Gln Val
            340                 345                 350

Tyr Ala Phe Leu Arg Ala Cys Leu Cys Arg Leu Val Pro Ala Gly Leu
        355                 360                 365

Trp Gly Ser Gly His Asn Arg Arg Phe Leu Arg Asn Val Lys Lys
    370                 375                 380

Phe Val Ser Leu Gly Lys His Ala Lys Leu Ser Leu Gln Glu Leu Thr
385                 390                 395                 400

Trp Lys Met Arg Val Gln Asp Cys Ala Trp Leu Arg Gly Ser Pro Gly
                405                 410                 415

Ala Arg Cys Val Pro Ala Ala Glu His Arg Arg Arg Glu Glu Val Leu
            420                 425                 430

Ala Lys Leu Leu Cys Trp Leu Met Gly Thr Tyr Val Glu Leu Leu
        435                 440                 445

Lys Ser Phe Phe Tyr Val Thr Glu Thr Thr Phe Gln Lys Asn Arg Leu
450                 455                 460

Phe Phe Tyr Arg Lys Arg Ile Trp Ser Gln Leu Gln Ser Ile Gly Ile
465                 470                 475                 480

Arg Gln His Phe Asn Ser Val His Leu Arg Glu Leu Ser Glu Ala Glu
                485                 490                 495
```

-continued

Val Arg Arg His Gln Glu Ala Arg Pro Thr Leu Leu Thr Ser Lys Leu
            500                 505                 510

Arg Phe Leu Pro Lys Pro Ser Gly Leu Arg Pro Ile Val Asn Met Asp
        515                 520                 525

Tyr Val Val Gly Ala Arg Thr Phe Arg Arg Asp Lys Lys Val Arg His
    530                 535                 540

Leu Thr Ser Gln Val Lys Asn Leu Phe Ser Val Leu Asn Tyr Glu Arg
545                 550                 555                 560

Ala Arg Arg Pro Ser Leu Leu Gly Ala Ser Val Leu Gly Met Asp Asp
                565                 570                 575

Ile His Arg Val Trp Arg Ser Phe Val Leu Arg Val Arg Ala Gln Asp
            580                 585                 590

Pro Ala Pro Gln Leu Tyr Phe Val Lys Val Asp Val Thr Gly Ala Tyr
        595                 600                 605

Asp Ala Leu Pro Gln Asp Lys Leu Val Glu Val Ile Ala Asn Val Ile
    610                 615                 620

Arg Pro Gln Glu Asn Thr Tyr Cys Val Arg His Tyr Ala Val Val Gln
625                 630                 635                 640

Arg Thr Ala Gln Gly His Val Arg Lys Ser Phe Lys Arg His Val Ser
                645                 650                 655

Thr Phe Val Asp Leu Gln Pro Tyr Met Arg Gln Phe Val Glu His Leu
            660                 665                 670

Gln Glu Thr Ser Ser Leu Arg Asp Ala Val Val Ile Glu Gln Ser Ser
        675                 680                 685

Ser Leu Asn Glu Thr Gly His Ser Leu Phe His Leu Phe Leu Arg Leu
    690                 695                 700

Val His Asn His Val Ile Arg Ile Gly Gly Lys Ser Tyr Val Gln Cys
705                 710                 715                 720

Gln Gly Ile Pro Gln Gly Ser Ile Leu Ser Thr Leu Leu Cys Ser Leu
                725                 730                 735

Cys Tyr Gly Asp Met Glu Ser Arg Leu Phe Ser Gly Ile Gln Gln Asp
            740                 745                 750

Gly Val Leu Leu Arg Leu Val Asp Asp Phe Leu Leu Val Thr Pro His
        755                 760                 765

Leu Ala Gln Ala Gln Ala Phe Leu Arg Thr Leu Val Ser Gly Val Pro
    770                 775                 780

Glu Tyr Gly Cys Thr Ala Asn Leu Gln Lys Thr Ala Val Asn Phe Pro
785                 790                 795                 800

Val Asp Thr Gly Ala Pro Gly Ser Ala Ala Pro Leu Gln Leu Pro Ala
                805                 810                 815

His Cys Leu Phe Pro Trp Cys Gly Leu Leu Leu Asp Thr Arg Thr Leu
            820                 825                 830

Glu Val Phe Cys Asp Tyr Ser Ser Tyr Ala Gln Thr Ser Ile Arg Ser
        835                 840                 845

Ser Leu Thr Phe Ser Gln Gly Thr Arg Pro Gly Arg Asn Met Arg Arg
    850                 855                 860

Lys Leu Leu Ala Val Met Arg Leu Lys Cys Cys Ala Val Phe Leu Asp
865                 870                 875                 880

Leu Gln Val Asn Ser Ile His Thr Val Tyr Thr Asn Ile Tyr Lys Ile
                885                 890                 895

Phe Leu Leu Gln Ala Tyr Arg Phe His Ala Cys Val Leu Gln Phe Pro
            900                 905                 910

Phe Asn Gln Pro Val Arg Lys Asn Pro Ser Phe Phe Leu Arg Val Ile

```
                915                 920                 925
Ala Asp Thr Ala Ser Arg Cys Tyr Ser Leu Leu Lys Ala Lys Asn Thr
    930                 935                 940

Gly Leu Ser Leu Gly Ala Lys Gly Ala Ser Gly Pro Phe Pro Ser Glu
945                 950                 955                 960

Ala Ala Arg Trp Leu Cys Leu His Ala Phe Leu Leu Lys Leu Ala Arg
                965                 970                 975

His Ser Ser Thr Tyr Arg Cys Leu Leu Gly Pro Leu Arg Ala Ala Lys
            980                 985                 990

Ala Gln Leu Arg Arg Gln Leu Pro  Arg Ala Thr Leu Asp  Ala Leu Glu
        995                 1000                1005

Ala Ala  Ala Ser Pro Gly Leu  Pro Ala Asp Phe Arg  Thr Ile Leu
    1010                1015                1020

Asp

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H2-restricted peptide

<400> SEQUENCE: 8

Arg Pro Ile Val Asn Met Asp Tyr Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H2-restricted peptide

<400> SEQUENCE: 9

Arg Gln Leu Phe Asn Ser Val His Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H2-restricted peptide

<400> SEQUENCE: 10

Thr Val Tyr Met Asn Val Tyr Lys Ile
1               5

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: H2-restricted peptide

<400> SEQUENCE: 11

Cys Leu Leu Gly Pro Leu Arg Ala Ala Lys Ala His Leu Ser Arg
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H2-restricted peptide

<400> SEQUENCE: 12

Arg Cys Leu Leu Gly Pro Leu Arg Ala Ala Lys Ala His Leu Ser
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H2-restricted peptide

<400> SEQUENCE: 13

Tyr Ser Ser Tyr Ala Gln Thr Ser Ile Arg Ser Ser Leu Thr Phe
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H2-restricted peptide

<400> SEQUENCE: 14

Gly Pro Leu Arg Ala Ala Lys Ala His Leu Ser Arg Gln Leu Pro
1               5                   10                  15

<210> SEQ ID NO 15
<211> LENGTH: 15
<212> TYPE: PRT
<213> ORGANISM: Canis familiaris

<400> SEQUENCE: 15

Pro Gln Lys Pro Gly Ala Ala Arg Arg Met Arg Arg Leu Pro Ala
1               5                   10                  15

<210> SEQ ID NO 16
<211> LENGTH: 15
<212> TYPE: PRT
<213> ORGANISM: Canis familiaris

<400> SEQUENCE: 16

Gly Ala Ala Arg Arg Met Arg Arg Leu Pro Ala Arg Tyr Trp Arg
1               5                   10                  15

<210> SEQ ID NO 17
```

```
<211> LENGTH: 15
<212> TYPE: PRT
<213> ORGANISM: Canis familiaris

<400> SEQUENCE: 17

Arg Met Arg Arg Leu Pro Ala Arg Tyr Trp Arg Met Arg Pro Leu
1               5                   10                  15

<210> SEQ ID NO 18
<211> LENGTH: 15
<212> TYPE: PRT
<213> ORGANISM: Canis familiaris

<400> SEQUENCE: 18

Leu Pro Ala Arg Tyr Trp Arg Met Arg Pro Leu Phe Gln Glu Leu
1               5                   10                  15

<210> SEQ ID NO 19
<211> LENGTH: 15
<212> TYPE: PRT
<213> ORGANISM: Canis familiaris

<400> SEQUENCE: 19

Tyr Trp Arg Met Arg Pro Leu Phe Gln Glu Leu Leu Gly Asn His
1               5                   10                  15

<210> SEQ ID NO 20
<211> LENGTH: 15
<212> TYPE: PRT
<213> ORGANISM: Canis familiaris

<400> SEQUENCE: 20

Arg Pro Leu Phe Gln Glu Leu Leu Gly Asn His Ala Arg Cys Pro
1               5                   10                  15

<210> SEQ ID NO 21
<211> LENGTH: 15
<212> TYPE: PRT
<213> ORGANISM: Canis familiaris

<400> SEQUENCE: 21

Gln Glu Leu Leu Gly Asn His Ala Arg Cys Pro Tyr Arg Ala Leu
1               5                   10                  15

<210> SEQ ID NO 22
<211> LENGTH: 15
<212> TYPE: PRT
<213> ORGANISM: Canis familiaris

<400> SEQUENCE: 22

Gly Asn His Ala Arg Cys Pro Tyr Arg Ala Leu Leu Arg Thr His
1               5                   10                  15

<210> SEQ ID NO 23
<211> LENGTH: 15
<212> TYPE: PRT
<213> ORGANISM: Canis familiaris

<400> SEQUENCE: 23

Arg Cys Pro Tyr Arg Ala Leu Leu Arg Thr His Cys Pro Leu Arg
1               5                   10                  15

<210> SEQ ID NO 24
<211> LENGTH: 15
<212> TYPE: PRT
```

<213> ORGANISM: Canis familiaris

<400> SEQUENCE: 24

Arg Ala Leu Leu Arg Thr His Cys Pro Leu Arg Ala Met Ala Ala
1               5                   10                  15

<210> SEQ ID NO 25
<211> LENGTH: 15
<212> TYPE: PRT
<213> ORGANISM: Canis familiaris

<400> SEQUENCE: 25

Arg Thr His Cys Pro Leu Arg Ala Met Ala Ala Lys Glu Gly Ser
1               5                   10                  15

<210> SEQ ID NO 26
<211> LENGTH: 15
<212> TYPE: PRT
<213> ORGANISM: Canis familiaris

<400> SEQUENCE: 26

Pro Leu Arg Ala Met Ala Ala Lys Glu Gly Ser Gly Asn Gln Ala
1               5                   10                  15

<210> SEQ ID NO 27
<211> LENGTH: 15
<212> TYPE: PRT
<213> ORGANISM: Canis familiaris

<400> SEQUENCE: 27

Met Ala Ala Lys Glu Gly Ser Gly Asn Gln Ala His Arg Gly Val
1               5                   10                  15

<210> SEQ ID NO 28
<211> LENGTH: 15
<212> TYPE: PRT
<213> ORGANISM: Canis familiaris

<400> SEQUENCE: 28

Glu Gly Ser Gly Asn Gln Ala His Arg Gly Val Gly Ile Cys Pro
1               5                   10                  15

<210> SEQ ID NO 29
<211> LENGTH: 15
<212> TYPE: PRT
<213> ORGANISM: Canis familiaris

<400> SEQUENCE: 29

Asn Gln Ala His Arg Gly Val Gly Ile Cys Pro Leu Glu Arg Pro
1               5                   10                  15

<210> SEQ ID NO 30
<211> LENGTH: 15
<212> TYPE: PRT
<213> ORGANISM: Canis familiaris

<400> SEQUENCE: 30

Arg Gly Val Gly Ile Cys Pro Leu Glu Arg Pro Val Ala Ala Pro
1               5                   10                  15

<210> SEQ ID NO 31
<211> LENGTH: 15
<212> TYPE: PRT
<213> ORGANISM: Canis familiaris

```
<400> SEQUENCE: 31

Ile Cys Pro Leu Glu Arg Pro Val Ala Ala Pro Gln Glu Gln Thr
1               5                   10                  15

<210> SEQ ID NO 32
<211> LENGTH: 15
<212> TYPE: PRT
<213> ORGANISM: Canis familiaris

<400> SEQUENCE: 32

Pro Gln Lys Pro Gly Ala Ala Arg Arg Met Arg Arg Leu Pro Ala
1               5                   10                  15

<210> SEQ ID NO 33
<211> LENGTH: 15
<212> TYPE: PRT
<213> ORGANISM: Canis familiaris

<400> SEQUENCE: 33

Ala Lys Leu Ser Leu Gln Glu Leu Thr Trp Lys Met Lys Val Arg
1               5                   10                  15

<210> SEQ ID NO 34
<211> LENGTH: 15
<212> TYPE: PRT
<213> ORGANISM: Canis familiaris

<400> SEQUENCE: 34

Leu Gln Glu Leu Thr Trp Lys Met Lys Val Arg Asp Cys Thr Trp
1               5                   10                  15

<210> SEQ ID NO 35
<211> LENGTH: 15
<212> TYPE: PRT
<213> ORGANISM: Canis familiaris

<400> SEQUENCE: 35

Thr Trp Lys Met Lys Val Arg Asp Cys Thr Trp Leu His Gly Asn
1               5                   10                  15

<210> SEQ ID NO 36
<211> LENGTH: 15
<212> TYPE: PRT
<213> ORGANISM: Canis familiaris

<400> SEQUENCE: 36

Lys Val Arg Asp Cys Thr Trp Leu His Gly Asn Pro Gly Ala Cys
1               5                   10                  15

<210> SEQ ID NO 37
<211> LENGTH: 15
<212> TYPE: PRT
<213> ORGANISM: Canis familiaris

<400> SEQUENCE: 37

Cys Thr Trp Leu His Gly Asn Pro Gly Ala Cys Cys Val Pro Ala
1               5                   10                  15

<210> SEQ ID NO 38
<211> LENGTH: 15
<212> TYPE: PRT
<213> ORGANISM: Canis familiaris

<400> SEQUENCE: 38
```

His Gly Asn Pro Gly Ala Cys Cys Val Pro Ala Ala Glu His Arg
1               5                   10                  15

<210> SEQ ID NO 39
<211> LENGTH: 15
<212> TYPE: PRT
<213> ORGANISM: Canis familiaris

<400> SEQUENCE: 39

Gly Ala Cys Cys Val Pro Ala Ala Glu His Arg Arg Arg Glu Glu
1               5                   10                  15

<210> SEQ ID NO 40
<211> LENGTH: 15
<212> TYPE: PRT
<213> ORGANISM: Canis familiaris

<400> SEQUENCE: 40

Val Pro Ala Ala Glu His Arg Arg Arg Glu Glu Ile Leu Ala Arg
1               5                   10                  15

<210> SEQ ID NO 41
<211> LENGTH: 15
<212> TYPE: PRT
<213> ORGANISM: Canis familiaris

<400> SEQUENCE: 41

Glu His Arg Arg Arg Glu Glu Ile Leu Ala Arg Phe Leu Val Leu
1               5                   10                  15

<210> SEQ ID NO 42
<211> LENGTH: 15
<212> TYPE: PRT
<213> ORGANISM: Canis familiaris

<400> SEQUENCE: 42

Arg Glu Glu Ile Leu Ala Arg Phe Leu Val Leu Val Asp Gly His
1               5                   10                  15

<210> SEQ ID NO 43
<211> LENGTH: 15
<212> TYPE: PRT
<213> ORGANISM: Canis familiaris

<400> SEQUENCE: 43

Leu Ala Arg Phe Leu Val Leu Val Asp Gly His Ile Tyr Val Val
1               5                   10                  15

<210> SEQ ID NO 44
<211> LENGTH: 15
<212> TYPE: PRT
<213> ORGANISM: Canis familiaris

<400> SEQUENCE: 44

Leu Val Leu Val Asp Gly His Ile Tyr Val Val Lys Leu Leu Arg
1               5                   10                  15

<210> SEQ ID NO 45
<211> LENGTH: 15
<212> TYPE: PRT
<213> ORGANISM: Canis familiaris

<400> SEQUENCE: 45

Asp Gly His Ile Tyr Val Val Lys Leu Leu Arg Ser Phe Phe Tyr
1               5                   10                  15

```
<210> SEQ ID NO 46
<211> LENGTH: 15
<212> TYPE: PRT
<213> ORGANISM: Canis familiaris

<400> SEQUENCE: 46

Tyr Val Val Lys Leu Leu Arg Ser Phe Phe Tyr Val Thr Glu Thr
1               5                   10                  15

<210> SEQ ID NO 47
<211> LENGTH: 15
<212> TYPE: PRT
<213> ORGANISM: Canis familiaris

<400> SEQUENCE: 47

Leu Leu Arg Ser Phe Phe Tyr Val Thr Glu Thr Thr Phe Gln Lys
1               5                   10                  15

<210> SEQ ID NO 48
<211> LENGTH: 15
<212> TYPE: PRT
<213> ORGANISM: Canis familiaris

<400> SEQUENCE: 48

Phe Phe Tyr Val Thr Glu Thr Thr Phe Gln Lys Asn Arg Leu Phe
1               5                   10                  15

<210> SEQ ID NO 49
<211> LENGTH: 15
<212> TYPE: PRT
<213> ORGANISM: Canis familiaris

<400> SEQUENCE: 49

Thr Glu Thr Thr Phe Gln Lys Asn Arg Leu Phe Phe Tyr Arg Lys
1               5                   10                  15

<210> SEQ ID NO 50
<211> LENGTH: 14
<212> TYPE: PRT
<213> ORGANISM: Canis familiaris

<400> SEQUENCE: 50

Phe Gln Lys Asn Arg Leu Phe Phe Tyr Arg Lys Ser Val Trp
1               5                   10

<210> SEQ ID NO 51
<211> LENGTH: 15
<212> TYPE: PRT
<213> ORGANISM: Canis familiaris

<400> SEQUENCE: 51

Glu Gly Gly Pro Pro Gly Thr Arg Pro Thr Thr Pro Ala Trp His
1               5                   10                  15

<210> SEQ ID NO 52
<211> LENGTH: 15
<212> TYPE: PRT
<213> ORGANISM: Canis familiaris

<400> SEQUENCE: 52

Pro Gly Thr Arg Pro Thr Thr Pro Ala Trp His Pro Tyr Pro Gly
1               5                   10                  15
```

```
<210> SEQ ID NO 53
<211> LENGTH: 15
<212> TYPE: PRT
<213> ORGANISM: Canis familiaris

<400> SEQUENCE: 53

Pro Thr Thr Pro Ala Trp His Pro Tyr Pro Gly Pro Gln Gly Val
1               5                   10                  15

<210> SEQ ID NO 54
<211> LENGTH: 15
<212> TYPE: PRT
<213> ORGANISM: Canis familiaris

<400> SEQUENCE: 54

Ala Trp His Pro Tyr Pro Gly Pro Gln Gly Val Pro His Asp Pro
1               5                   10                  15

<210> SEQ ID NO 55
<211> LENGTH: 15
<212> TYPE: PRT
<213> ORGANISM: Canis familiaris

<400> SEQUENCE: 55

Tyr Pro Gly Pro Gln Gly Val Pro His Asp Pro Ala His Pro Glu
1               5                   10                  15

<210> SEQ ID NO 56
<211> LENGTH: 15
<212> TYPE: PRT
<213> ORGANISM: Canis familiaris

<400> SEQUENCE: 56

Gln Gly Val Pro His Asp Pro Ala His Pro Glu Thr Lys Arg Phe
1               5                   10                  15

<210> SEQ ID NO 57
<211> LENGTH: 15
<212> TYPE: PRT
<213> ORGANISM: Canis familiaris

<400> SEQUENCE: 57

His Asp Pro Ala His Pro Glu Thr Lys Arg Phe Leu Tyr Cys Ser
1               5                   10                  15

<210> SEQ ID NO 58
<211> LENGTH: 15
<212> TYPE: PRT
<213> ORGANISM: Canis familiaris

<400> SEQUENCE: 58

His Pro Glu Thr Lys Arg Phe Leu Tyr Cys Ser Gly Gly Arg Glu
1               5                   10                  15

<210> SEQ ID NO 59
<211> LENGTH: 15
<212> TYPE: PRT
<213> ORGANISM: Canis familiaris

<400> SEQUENCE: 59

Lys Arg Phe Leu Tyr Cys Ser Gly Gly Arg Glu Arg Leu Arg Pro
1               5                   10                  15

<210> SEQ ID NO 60
<211> LENGTH: 15
```

```
<212> TYPE: PRT
<213> ORGANISM: Canis familiaris

<400> SEQUENCE: 60

Tyr Cys Ser Gly Gly Arg Glu Arg Leu Arg Pro Ser Phe Leu Leu
1               5                   10                  15

<210> SEQ ID NO 61
<211> LENGTH: 15
<212> TYPE: PRT
<213> ORGANISM: Canis familiaris

<400> SEQUENCE: 61

Gly Arg Glu Arg Leu Arg Pro Ser Phe Leu Leu Ser Ala Leu Pro
1               5                   10                  15

<210> SEQ ID NO 62
<211> LENGTH: 15
<212> TYPE: PRT
<213> ORGANISM: Canis familiaris

<400> SEQUENCE: 62

Leu Arg Pro Ser Phe Leu Leu Ser Ala Leu Pro Pro Thr Leu Ser
1               5                   10                  15

<210> SEQ ID NO 63
<211> LENGTH: 15
<212> TYPE: PRT
<213> ORGANISM: Canis familiaris

<400> SEQUENCE: 63

Phe Leu Leu Ser Ala Leu Pro Pro Thr Leu Ser Gly Ala Arg Lys
1               5                   10                  15

<210> SEQ ID NO 64
<211> LENGTH: 15
<212> TYPE: PRT
<213> ORGANISM: Canis familiaris

<400> SEQUENCE: 64

Ala Leu Pro Pro Thr Leu Ser Gly Ala Arg Lys Leu Val Glu Thr
1               5                   10                  15

<210> SEQ ID NO 65
<211> LENGTH: 15
<212> TYPE: PRT
<213> ORGANISM: Canis familiaris

<400> SEQUENCE: 65

Asp Cys Thr Trp Leu His Gly Asn Pro Gly Ala Cys Cys Val Pro
1               5                   10                  15

<210> SEQ ID NO 66
<211> LENGTH: 15
<212> TYPE: PRT
<213> ORGANISM: Canis familiaris

<400> SEQUENCE: 66

Leu His Gly Asn Pro Gly Ala Cys Cys Val Pro Ala Ala Glu His
1               5                   10                  15

<210> SEQ ID NO 67
<211> LENGTH: 15
<212> TYPE: PRT
<213> ORGANISM: Canis familiaris
```

<400> SEQUENCE: 67

Pro Gly Ala Cys Cys Val Pro Ala Ala Glu His Arg Arg Arg Glu
1               5                   10                  15

<210> SEQ ID NO 68
<211> LENGTH: 15
<212> TYPE: PRT
<213> ORGANISM: Canis familiaris

<400> SEQUENCE: 68

Cys Val Pro Ala Ala Glu His Arg Arg Arg Glu Glu Ile Leu Ala
1               5                   10                  15

<210> SEQ ID NO 69
<211> LENGTH: 15
<212> TYPE: PRT
<213> ORGANISM: Canis familiaris

<400> SEQUENCE: 69

Ala Glu His Arg Arg Arg Glu Glu Ile Leu Ala Arg Phe Leu Val
1               5                   10                  15

<210> SEQ ID NO 70
<211> LENGTH: 15
<212> TYPE: PRT
<213> ORGANISM: Canis familiaris

<400> SEQUENCE: 70

Arg Arg Glu Glu Ile Leu Ala Arg Phe Leu Val Leu Val Asp Gly
1               5                   10                  15

<210> SEQ ID NO 71
<211> LENGTH: 15
<212> TYPE: PRT
<213> ORGANISM: Canis familiaris

<400> SEQUENCE: 71

Ile Leu Ala Arg Phe Leu Val Leu Val Asp Gly His Ile Tyr Val
1               5                   10                  15

<210> SEQ ID NO 72
<211> LENGTH: 15
<212> TYPE: PRT
<213> ORGANISM: Canis familiaris

<400> SEQUENCE: 72

Phe Leu Val Leu Val Asp Gly His Ile Tyr Val Val Lys Leu Leu
1               5                   10                  15

<210> SEQ ID NO 73
<211> LENGTH: 15
<212> TYPE: PRT
<213> ORGANISM: Canis familiaris

<400> SEQUENCE: 73

Val Asp Gly His Ile Tyr Val Val Lys Leu Leu Arg Ser Phe Phe
1               5                   10                  15

<210> SEQ ID NO 74
<211> LENGTH: 15
<212> TYPE: PRT
<213> ORGANISM: Canis familiaris

<400> SEQUENCE: 74

Ile Tyr Val Val Lys Leu Leu Arg Ser Phe Phe Tyr Val Thr Glu
1               5                   10                  15

<210> SEQ ID NO 75
<211> LENGTH: 15
<212> TYPE: PRT
<213> ORGANISM: Canis familiaris

<400> SEQUENCE: 75

Lys Leu Leu Arg Ser Phe Phe Tyr Val Thr Glu Thr Thr Phe Gln
1               5                   10                  15

<210> SEQ ID NO 76
<211> LENGTH: 15
<212> TYPE: PRT
<213> ORGANISM: Canis familiaris

<400> SEQUENCE: 76

Ser Phe Phe Tyr Val Thr Glu Thr Thr Phe Gln Lys Asn Arg Leu
1               5                   10                  15

<210> SEQ ID NO 77
<211> LENGTH: 15
<212> TYPE: PRT
<213> ORGANISM: Canis familiaris

<400> SEQUENCE: 77

Val Thr Glu Thr Thr Phe Gln Lys Asn Arg Leu Phe Phe Tyr Arg
1               5                   10                  15

<210> SEQ ID NO 78
<211> LENGTH: 15
<212> TYPE: PRT
<213> ORGANISM: Canis familiaris

<400> SEQUENCE: 78

Thr Phe Gln Lys Asn Arg Leu Phe Phe Tyr Arg Lys Ser Val Trp
1               5                   10                  15

<210> SEQ ID NO 79
<211> LENGTH: 15
<212> TYPE: PRT
<213> ORGANISM: Canis familiaris

<400> SEQUENCE: 79

Gln Leu Pro Phe Asn Gln Pro Val Arg Lys Asn Pro Ser Phe Phe
1               5                   10                  15

<210> SEQ ID NO 80
<211> LENGTH: 15
<212> TYPE: PRT
<213> ORGANISM: Canis familiaris

<400> SEQUENCE: 80

Asn Gln Pro Val Arg Lys Asn Pro Ser Phe Phe Leu Arg Val Ile
1               5                   10                  15

<210> SEQ ID NO 81
<211> LENGTH: 15
<212> TYPE: PRT
<213> ORGANISM: Canis familiaris

<400> SEQUENCE: 81

Arg Lys Asn Pro Ser Phe Phe Leu Arg Val Ile Ala Asp Thr Ala

<210> SEQ ID NO 82
<211> LENGTH: 15
<212> TYPE: PRT
<213> ORGANISM: Canis familiaris

<400> SEQUENCE: 82

Ser Phe Phe Leu Arg Val Ile Ala Asp Thr Ala Ser Cys Cys Tyr
1               5                   10                  15

<210> SEQ ID NO 83
<211> LENGTH: 15
<212> TYPE: PRT
<213> ORGANISM: Canis familiaris

<400> SEQUENCE: 83

Arg Val Ile Ala Asp Thr Ala Ser Cys Cys Tyr Ser Leu Leu Lys
1               5                   10                  15

<210> SEQ ID NO 84
<211> LENGTH: 15
<212> TYPE: PRT
<213> ORGANISM: Canis familiaris

<400> SEQUENCE: 84

Asp Thr Ala Ser Cys Cys Tyr Ser Leu Leu Lys Ala Arg Asn Ala
1               5                   10                  15

<210> SEQ ID NO 85
<211> LENGTH: 15
<212> TYPE: PRT
<213> ORGANISM: Canis familiaris

<400> SEQUENCE: 85

Cys Cys Tyr Ser Leu Leu Lys Ala Arg Asn Ala Gly Leu Ser Leu
1               5                   10                  15

<210> SEQ ID NO 86
<211> LENGTH: 15
<212> TYPE: PRT
<213> ORGANISM: Canis familiaris

<400> SEQUENCE: 86

Leu Leu Lys Ala Arg Asn Ala Gly Leu Ser Leu Gly Ala Lys Gly
1               5                   10                  15

<210> SEQ ID NO 87
<211> LENGTH: 15
<212> TYPE: PRT
<213> ORGANISM: Canis familiaris

<400> SEQUENCE: 87

Arg Asn Ala Gly Leu Ser Leu Gly Ala Lys Gly Ala Ser Gly Leu
1               5                   10                  15

<210> SEQ ID NO 88
<211> LENGTH: 15
<212> TYPE: PRT
<213> ORGANISM: Canis familiaris

<400> SEQUENCE: 88

Leu Ser Leu Gly Ala Lys Gly Ala Ser Gly Leu Phe Pro Ser Glu
1               5                   10                  15

```
<210> SEQ ID NO 89
<211> LENGTH: 15
<212> TYPE: PRT
<213> ORGANISM: Canis familiaris

<400> SEQUENCE: 89

Ala Lys Gly Ala Ser Gly Leu Phe Pro Ser Glu Ala Ala Arg Trp
1               5                   10                  15

<210> SEQ ID NO 90
<211> LENGTH: 15
<212> TYPE: PRT
<213> ORGANISM: Canis familiaris

<400> SEQUENCE: 90

Ser Gly Leu Phe Pro Ser Glu Ala Ala Arg Trp Leu Cys Leu His
1               5                   10                  15

<210> SEQ ID NO 91
<211> LENGTH: 14
<212> TYPE: PRT
<213> ORGANISM: Canis familiaris

<400> SEQUENCE: 91

Pro Ser Glu Ala Ala Arg Trp Leu Cys Leu His Ala Phe Leu
1               5                   10

<210> SEQ ID NO 92
<211> LENGTH: 15
<212> TYPE: PRT
<213> ORGANISM: Canis familiaris

<400> SEQUENCE: 92

Ala Arg Trp Leu Cys Leu His Ala Phe Leu Leu Lys Leu Ala His
1               5                   10                  15
```

CANCER VACCINE FOR DOGS

The present invention relates to cancer vaccination in dogs.

This application is the U.S. National Phase of International Patent Application Serial No. PCT/EP2014/056381, filed on Mar. 28, 2014, which claims priority to European Patent Application No. EP 13305405.6, filed on Mar. 28, 2013, both of which applications are herein incorporated by reference in their entirety.

SEQUENCE LISTING

The instant application contains a Sequence Listing which has been submitted electronically in ASCII format and is hereby incorporated by reference in its entirety. Said ASCII copy, created on Apr. 10, 2018, is named 246393_000004_SL.txt and is 100,731 bytes in size.

BACKGROUND OF THE INVENTION

Like their human counterparts, dogs that live in developed countries have seen their life expectancy consistently prolonged. Therefore, the global burden of cancers continues to increase largely because of the aging and growing dog population.

The incidence rate of cancers in the canine population is estimated to be between 282.2 to 958 per 100,000 dogs (Merlo et al. 2008, Vascellari et al. 2009). The most frequent tumors in dogs are mammary tumors in females (70.5% of all cancers), non-Hodgkin's lymphomas (8.4% in females and 20.1% in males) and skin tumors (4% in females and 19.9% in males). Moreover, according to the European Society of Veterinary Oncology 50% of dogs over ten years are going to die from a cancer-related problem.

The panel of treatments available against veterinary cancer is substantially reduced compared with those available in human oncology.

Surgery remains the best way to treat animal tumors. This method presents the advantage of being accessible for many veterinarians, and, in many cases, it can be curative. However, to be curative, surgery must be bold. However in some cases the tumor is too large, too dispersed or just not accessible enough to be entirely removed. If not totally curative, surgery can still be a palliative solution to improve the animal's comfort and prolong its life expectancy.

Radiotherapy is another important means to treat certain types of cancers in the veterinary field. It is of particular interest for tumors which are hardly accessible for surgery like cerebral tumors (de Fornel et al. 2007). Furthermore, recent studies in humans have demonstrated that ionizing radiation (IR) could act as an immunomodulator by inducing substantial changes in the tumor microenvironment, including triggering an inflammatory process. Furthermore, the cost and the availability of the material make access to radiation therapy complicated for companion animals.

Chemotherapy is more and more used in animal oncology (Marconato 2011). Taking advantages of medical advances in human cancer therapy, there are more and more molecules available like vincristine, cyclophosphamide, carboplatin or cisplatin, to treat companion animals. In the veterinary field, anticancer drugs are particularly used in the treatment of tumors derived from hematopoietic tissue (lymphomas, leukemias). For example the CHOP protocol, combining cyclophosphamide, doxorubicin, vincristine and prednisone is currently used in the treatment of numerous lymphomas (Chun 2009). Chemotherapeutic agents can be particularly efficient in prolonging the life span of a cancerous animal from a few weeks to several months (the median survival time of dogs treated with the CHOP protocol is 13 months). Interestingly, the side effects dreaded by human patients, such as vomiting, diarrhea, hair loss, are usually less frequent in companion animals. Unfortunately, most of the time chemotherapy is not curative in pets and the tumor often escapes treatment.

Therefore, just as in human medicine, targeted therapies are in development in veterinary medicine. Thus, some drugs are already available in the clinics like "Masitinib", an inhibitor of the tyrosine kinase c-kit (Gentilini 2010). Other treatments, including immunotherapies, are under investigation (Manley et al. 2011). These immunotherapeutic treatments are all based on the fact that it is possible to activate the immune system of the host against cancer cells. The relationship between the host immune system and cancer is dynamic and complex. Each type of tumor cell harbors a multitude of somatic mutations and epigenetically deregulated genes, the products of which are potentially recognizable as foreign antigens by immune cells (MUC-1, β-catenin, telomerase . . . ) (Fridman et al. 2012). Growing tumors contain infiltrating lymphocytes called TILs (Tumor Infiltrating Lymphocytes). These killer cells are often ineffective at tumor elimination in vivo but can exert specific functions in vitro, that is to say outside the immunosuppressive tumor microenvironment (Restifo et al. 2012). This is because the tumor stroma contains many suppressive elements including regulatory T cells (Tregs) and myeloid-derived suppressor cells (MDCs); soluble factors such as interleukin 6 (IL-6), IL-10, vascular endothelial growth factor (VEGF), and transforming growth factor beta (TGFβ) that down modulate antitumor immunity (Finn 2008, Hanahan and Weinberg 2011). Consequently, the choice of a pertinent tumor associated antigen (TAA) and the bypass of cancer associated immunosuppression are two critical points for a therapeutic vaccine to succeed (Disis et al. 2009).

Recent introduction of active cancer immunotherapy (also referred to cancer vaccines) in the clinical cancer practice emphasizes the role of immune responses in cancer prognosis and has led to a growing interest to extend this approach to several human and companion animal cancers (Dillman 2011, Topalian et al. 2011) (Jourdier et al. 2003).

In this context, there is still a need for an innovative cancer vaccine strategy for dogs, which would overcome the challenge of breaking tolerance and inducing an immune response in the animal.

SUMMARY OF THE INVENTION

The inventors now propose a cancer vaccine strategy for dogs, based on the telomerase reverse transcriptase (TERT).

A subject of the invention is thus an immunogenic composition comprising a nucleic acid that comprises a sequence encoding (i) a dog TERT deprived of telomerase catalytic activity, or (ii) a fragment thereof. The nucleic acid is preferably DNA, preferably in form of a plasmid.

In a preferred embodiment, the nucleic acid that comprises a sequence encoding a dog telomerase reverse transcriptase (TERT) deprived of telomerase catalytic activity, wherein the sequence encoding dog TERT is further deprived of a nucleolar localization signal.

In a particular embodiment, the nucleic acid further comprises a non-dog TERT antigenic fragment.

A further subject of the invention is a nucleic acid that comprises a sequence encoding (i) a dog TERT deprived of telomerase catalytic activity, or (ii) a fragment thereof, and optionally further comprises a non-dog TERT antigenic fragment.

The immunogenic composition or the nucleic acid is useful in triggering an immune response in a dog, against cells that over-express telomerase, such as dysplasia cells or tumor cells.

The immunogenic composition or the nucleic acid is thus particularly useful in treating a tumor in a dog, preferably by intradermal or intramuscular route.

Such treatment can be referred to as an active immunotherapy or a therapeutic vaccination, as it triggers an immune response against the tumor, especially a cytotoxic CD8 T cell response, along with a specific CD4 T cell response.

The invention makes it possible to induce dTERT specific responses in dogs with neoplasias and so can be used for immunotherapeutic treatments of the neoplasias in a clinical setting. The invention is also useful to induce dTERT specific responses in healthy dogs that could be at risk for cancer, e.g. by genetic predisposition, or in healthy dogs from a certain age (e.g. more than 10 years, preferably more than 12 years old), so as to prevent the onset of cancer.

Generally speaking, the treatment of the invention may induce long term immune memory responses in healthy dogs, dogs at risk of developing a cancer and those presenting a cancer.

BRIEF DESCRIPTION OF THE FIGURES

FIG. 1A shows pDUV5 nucleotide sequence (SEQ ID NO: 1) and corresponding amino acid sequence comprising dog TERT (dTERT) amino acid sequence (SEQ ID NO: 2). The plasmid pDUV5 encodes a near full length dog TERT nucleotide sequence. The nucleotide sequence encoding 3 key amino acids in the catalytic site of the protein have been deleted (VDD). Moreover, the sequence controlling the importation into the nucleoli (Nucleolar addressing signal) has been deleted (nucleotide sequence encoding 47 first Amino Acids in the N-term sequence of dTERT protein). Moreover the DNA sequence encoding the human ubiquitin has been added upstream the dTERT sequence. Presence of the ubiquitin protein enhances the addressing of the dTERT protein to the proteasome and increases class I presentation of derived peptides. However, as the human and dog ubiquitin sequences are identical at the protein level, there is no biological incompatibility. Downstream the dTERT sequence, the sequence of the V5 peptide of the flu was inserted to facilitate the detection of the protein.

Nucleotides 1-6 HindIII restriction site for subcloning
Nucleotides 13-240 ubiquitin
Nucleotides 241-3459 dog TERT
Nucleotides 2670-2671 inactivating deletion of 9 bp encoding VDD residues
Nucleotides 3460-3513 influenza A A2 epitope
Nucleotides 3514-3555 SV5 V5 tag
Nucleotides 3556-3561 two stop codons
Nucleotides 3562-3567 Xba1 restriction site for subcloning FIG. 1B shows pCDT nucleotide sequence (SEQ ID NO: 3) and corresponding amino acid sequence containing cat/dog hybrid TERT amino acid sequence (SEQ ID NO:4).

The plasmid pCDT encodes the cat/dog hybrid TERT (hyTERT) comprising 54.4% from the cat TERT and 35.9% from the dog TERT. The nucleotide sequence encoding 3 key amino acids in the catalytic site of the protein have been deleted (VDD). Moreover, the sequence controlling the importation into the nucleoli (Nucleolar addressing signal) has been depleted (nucleotide sequence encoding 47 first Amino Acids in the Nter sequence of hyTERT protein). The DNA sequence encoding the human ubiquitin has been added upstream the hyTERT sequence. The presence of the ubiquitin protein enhances the addressing of the hyTERT protein to the proteasome and increases class I presentation of the derived peptides. Downstream the hyTERT sequence, the sequence of the V5 peptide of the flu was inserted to facilitate the detection of the protein.

Figure 2A:
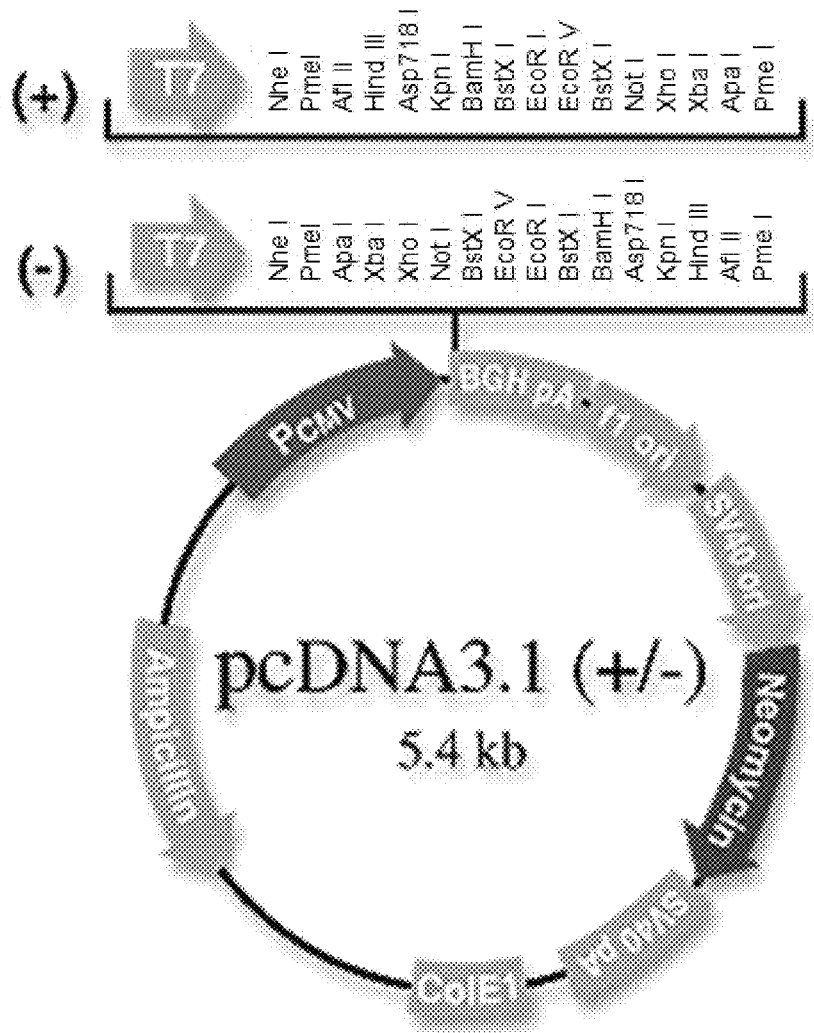

Nucleotides 1-6 HindIII restriction site for subcloning
Nucleotides 13-240 ubiquitin
Nucleotides 241-1413 dog TERT (35.9% of TERT sequences)
Nucleotides 1414-3351 cat TERT (54.4% of TERT sequences)
Nucleotides 3352-3456 dog TERT last exon
Nucleotides 3457-3510 influenza A2 epitope
Nucleotides 3511-3552 SV5 V5 tag
Nucleotides 2667-2668 inactivating deletion of 9 bp encoding VDD residues
Nucleotides 3553-3558 two stop codons
Nucleotides 3559-3564 Xba1 restriction site for subcloning FIG. 2A shows a simplified map of pcDNA3.1 expression plasmid into which the dog or hybrid TERT nucleic acid sequences are cloned.

FIG. 2B shows dog TERT protein sequence (SEQ ID NO: 5). The region covered by the dTERT 15mer peptide pool overlapping by 11 residues (70 peptides in total) that is used for in vitro immunization studies and ELIspot assays in dog PBMCs is shown in grey.

Figure 3:
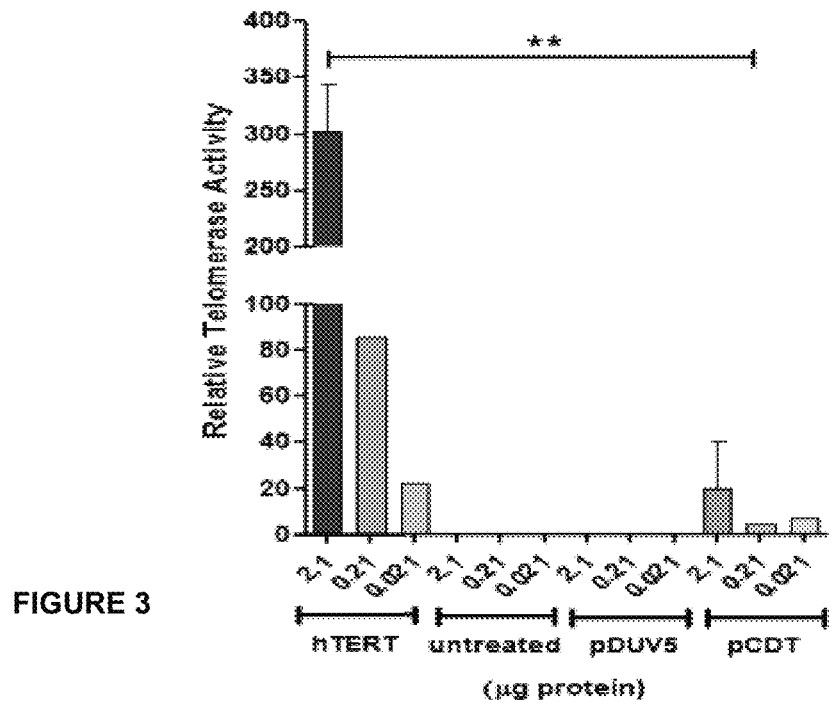

FIG. 3 shows that pDNA constructs are safe (Trapeze). Lysates obtained from CrFK cells transfected with hTERT, pCDT, or pDUV5 plasmids were analyzed for telomerase activity by the TRAP assay. The level of telomerase activity is shown as relative telomerase activity compared with that of control template measured in each kit and with the activity of a wild type human telomerase (hTERT). All samples at 2.1 µg protein concentration were measured in triplicate, error bars are standard error of the mean (SEM), (**P=0.0032, hTERT vs pDUV5 unpaired t test).

Figure 4:
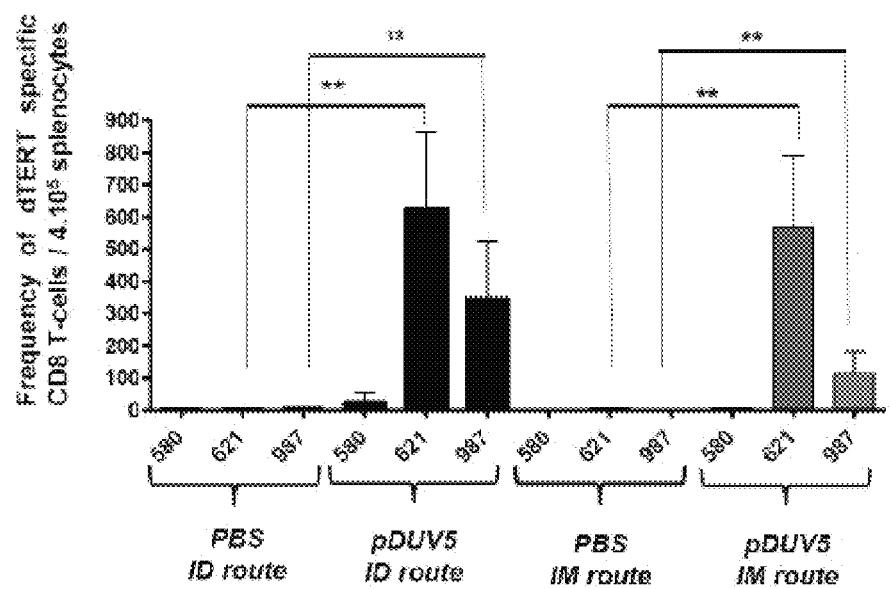

FIG. 4 is a graph showing that mice immunized with pDUV5 mount specific interferon-γ-secreting CD8 T-cell responses against H2 restricted dog TERT peptides.

7 week-old C57/B16 female mice were immunized intradermally (ID) or intramuscularly (IM) (10 mice per group) with 100 µg pDUV5 plasmid at day 0 and boost 14 days later. At the same time, control mice received PBS via ID or IM route (6 mice per group). Ten days after boost, spleens of all mice were harvested. Splenocytes were Ficoll purified and stimulated in triplicates with 5 ng/mL of relevant class I peptides (p580, p621 or p987) for 19 hours. Spots were revealed with a biotin-conjugated detection antibody followed by streptavidin-AP and BCIP/NBT substrate solution. Results are the mean±standard deviation. Mann Whitney non parametric test, * p-value<0.05, **: p-value<0.01.

Figure 5:
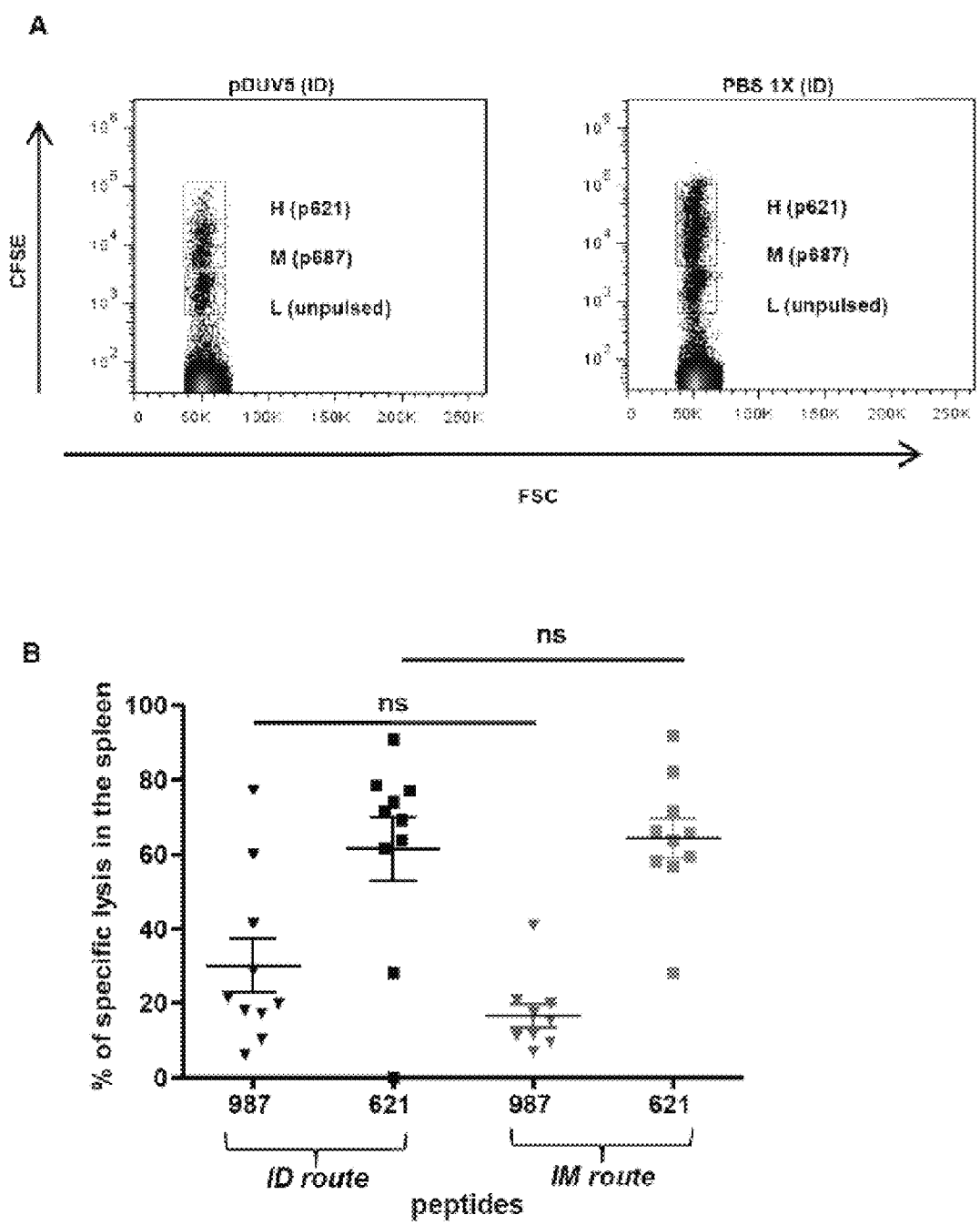

FIGS. 5A and 5B show that ID or IM immunization of mice with pDUV5 plasmid results in a dog TERT specific cytotoxic T-lymphocyte (CTL) response measurable in vivo by elimination of transferred target cells which were pulsed with dog TERT peptides restricted to H2.

Seven week-old C57/B16 female mice were immunized intradermally (ID) or intramuscularly (IM) with 100 µg pDUV5 plasmid at day 0 and day 14 post-priming. At day 9 post-boost injection, syngeneic splenocytes, pulsed with individual dTERT peptides restricted to H2 (either p987 or p621) or left unpulsed were labeled with carboxyfluorescein-diacetate succinimidyl ester (CFSE) at three different concentrations: high=1 μM (p621), medium=0.5 μM (p987) and low=0.1 μM (unpulsed). The same number of high, medium or low CFSE labeled cells was transferred IV to vaccinated mice. After 15-18 hours, the disappearance of peptide-pulsed cells was determined by fluorescence-activated cell-sorting analysis in the spleen. The percentage of specific lysis was calculated by comparing the ratio of pulsed to un-pulsed cells in vaccinated versus control mice.

(A) Example of the in vivo CTL assay showing the elimination of target cells pulsed with p987 (medium, M)/or p621 peptide (High, H) in the spleen of mice injected via the ID route (left panel). No such disappearing is observed in control mice injected ID with PBS 1× (right panel). H=high, M=Medium, L=Low (B) Percentage of specific lysis for each mouse against each individual peptide in the spleen after IM or ID vaccination with pDUV5. Horizontal bars show average percentage of lysis per peptide and per immunization route. Standard deviations are also plotted. Representative data from 2 independent experiments (n=10 individual animals/group). Kruskal-Wallis analysis with Dunn's multiple comparison test, ns: not significant. Statistical significance is set at p-value<0.05.

Figure 6:
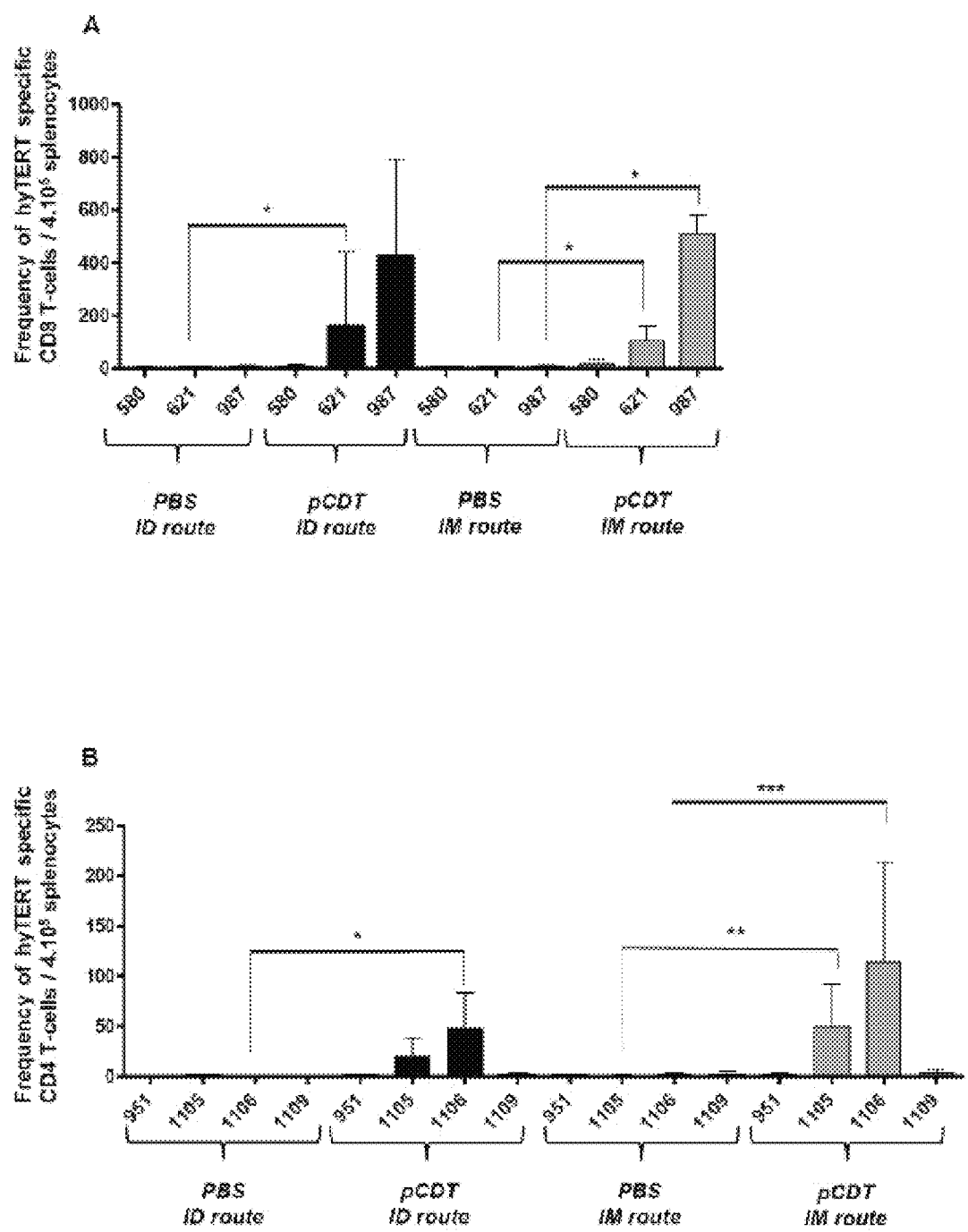

FIGS. 6A and 6B show IFNγ+ specific CD8 and CD4 T-cell responses against H2 restricted hyTERT peptides in mice immunized with pCDT.

Seven week-old female mice were immunized intradermally (ID) or intramuscularly (IM) with either 100 μg pCDT plasmid or PBS at day 0 and boost 14 days later. Ten day post-boost, spleens were harvested. Splenocytes were Ficoll-purified and stimulated in triplicates with 5 μg/mL of relevant peptides for 19 hours. Spots were revealed with a biotin-conjugated detection antibody followed by streptavidin-AP and BCIP/NBT substrate solution.

(A) Plasmid vaccinated groups were composed of five C57/B16 mice, and control groups, of three mice. Splenocytes were stimulated with class I peptides p580, p621 and p987. Results show the frequency of peptide specific IFN-γ producing CD8 T cells.

(B) Plasmid vaccinated groups were composed of 9 Balb/cBy mice immunized IM and 5 ID. Control groups of 8 Balb/cBy mice injected IM and 4 ID. Splenocytes were stimulated with class II peptides p951, p1105, p1106 and p1109. Results show the frequency of peptide specific IFN-γ producing CD4 T cells.

Results are the mean±standard deviation. Mann Whitney non parametric test, * p-value<0.05, **: p-value<0.01.

Figure 7:
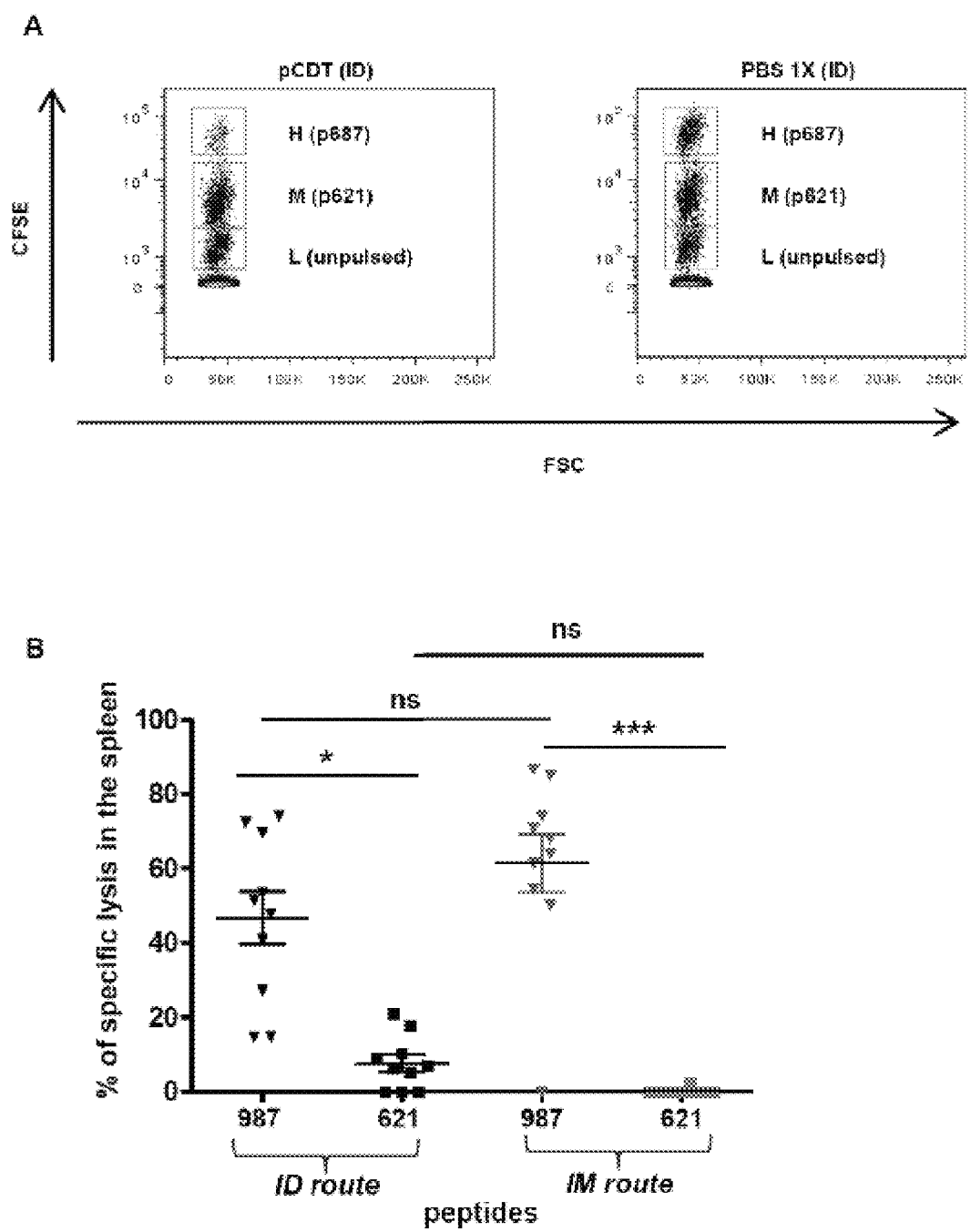

FIGS. 7A and 7B show hyTERT specific cytotoxic T-lymphocyte (CTL) response in mice immunized with pCDT plasmid, measurable in vivo by elimination of transferred target cells which were pulsed with hybrid TERT peptides restricted to H2.

7 week-old C57/B16 female mice were immunized ID or IM with 100 μg pCDT plasmid at day 0 and day 14 post-priming. At day 9 post-boost injection, syngeneic splenocytes, pulsed with individual dTERT peptides restricted to H2 (either p987 or p621) or left unpulsed were labeled with carboxyfluorescein-diacetate succinimidyl ester (CFSE) at three different concentrations: high=1 μM (p987), medium=0.5 μM (p621) and low=0.1 μM (unpulsed). The same number of high, medium or low CFSE labeled cells was transferred IV to vaccinated mice. After 15-18 hours, the disappearance of peptide-pulsed cells was determined by fluorescence-activated cell-sorting analysis in the spleen. The percentage of specific lysis was calculated by comparing the ratio of pulsed to un-pulsed cells in vaccinated versus control mice.

(A) Example of the in vivo CTL assay showing the elimination of target cells pulsed with p621 peptide (High, H) or p987 peptide (Medium, M) in the spleen of a mouse vaccinated ID (left panel) with pCDT. No such disappearing is observed in control mice injected ID with PBS 1× (right panel).

(B) Percentage of specific lysis for each mouse against each individual peptide in the spleen after IM or ID vaccination with pCDT. Horizontal bars show average percentage of lysis per peptide and per immunization route. Standard deviations are also plotted. Representative data from 2 independent experiments (n=10 individual animals/group). Kruskal-Wallis analysis with Dunn's multiple comparison test, * p<0,1, *** p<0,001, ns: not significant. Statistical significance is set at p-value<0.05.

Figure 8:
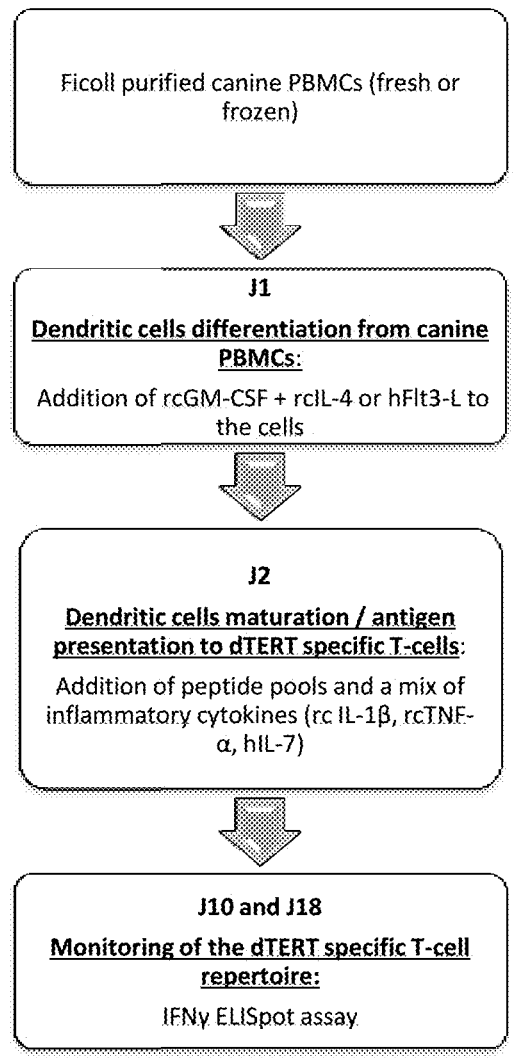

FIG. 8 shows principle of in vitro immunization in dog PBMCs Frozen dog PBMCs were incubated with recombinant canine GM-CSF (rcGM-CSF) and canine IL-4 (rcIL-4) or human FlT3 (hFlT3) ligand for 24 h. Maturation stimuli (rcTNFα, hIL-7 and rcIL-1β) were then added with dTERT overlapping peptides pools for 3 days. Eleven or 18 days of culture were performed and, TERT specific T cells were then detected via an IFN-γ ELISpot assay.

FIGS. 9A and 9B show a repertoire of dTERT specific IFN-γ secreting T cells in PBMCs from a naïve dog Frozen PBMCs incubated during 24 hours with either rcGM-CSF and rcIL-4 or hFlT3 ligand and matured 3 day long with dTERT overlapping peptides pools and maturation cytokines (rcTNFα, hIL-7 and caIL-1β were harvested after 11 or 18 days of culture to perform an ELISpot IFN-γ. Results show the frequency of peptide specific IFN-γ producing T cells/$10^6$ canine PBMC after 11 days (A) or 18 days (B) of culture.

Figure 10A:
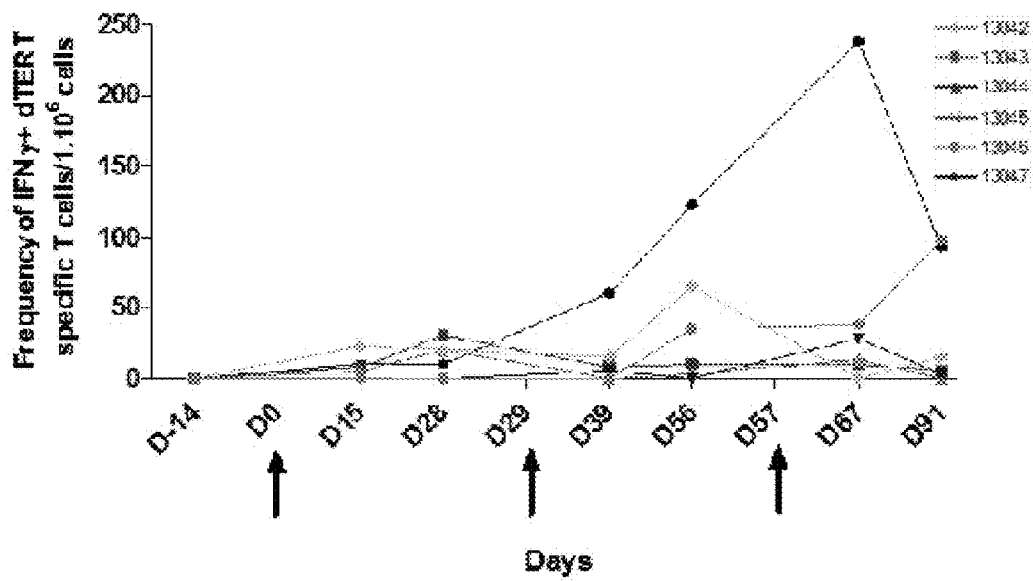
Figure 10B:
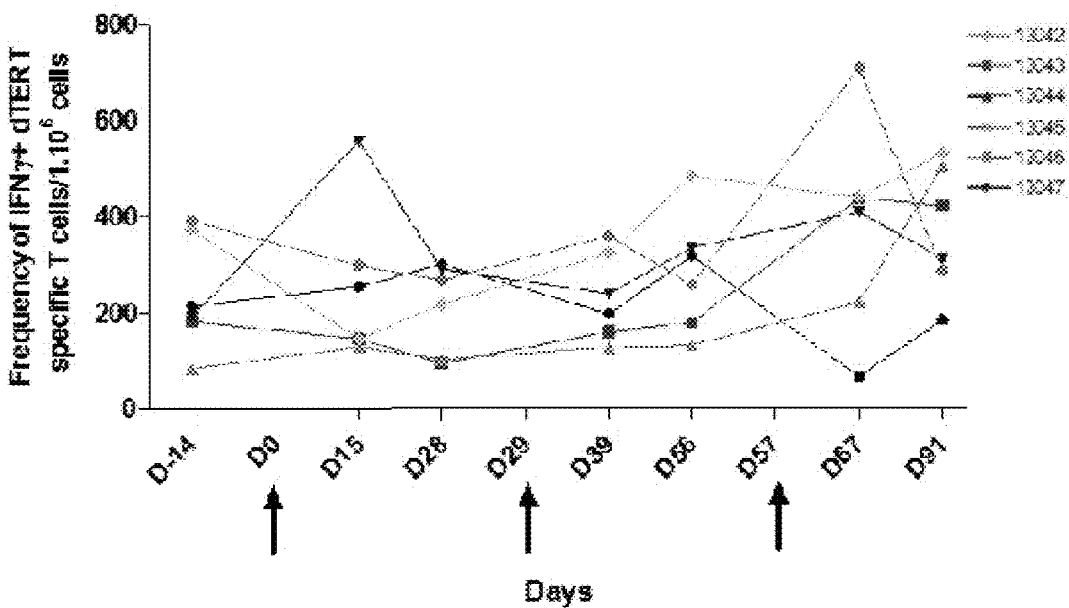

FIGS. 10A and 10B show the kinetics of the specific IFNγ T cell response against a first pool of dTERT peptides (pool 6), and a second pool of dTERT peptides (pool 19), respectively.

Six naïve beagle healthy dogs were injected intradermally with 400 μg of pDUV5 DNA followed by electroporation, at days 0, 29, 57 and 142. Peripheral blood was drawn and mononuclear cells tested for dog telomerase specific peptides belonging either to pool 6 or pool 19 peptides according to the method of Martinuzzi et al., 2011. IFNγ specific T cell responses were detected by ELISPOT assay, for pool 6 and 10 dTERT peptides, all of which above baseline readings.

Figure 11A:
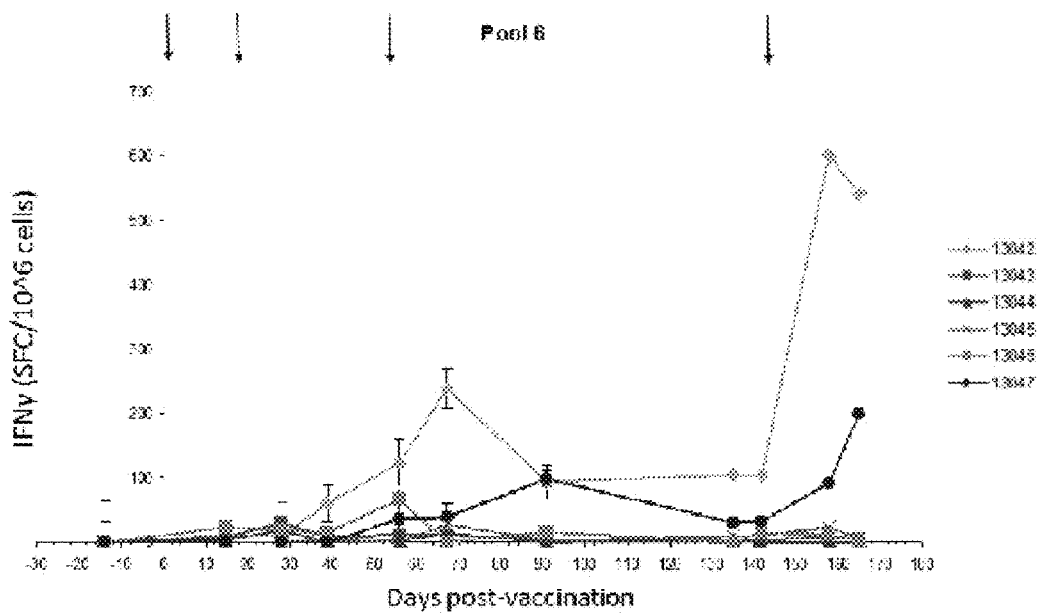
Figure 11B:
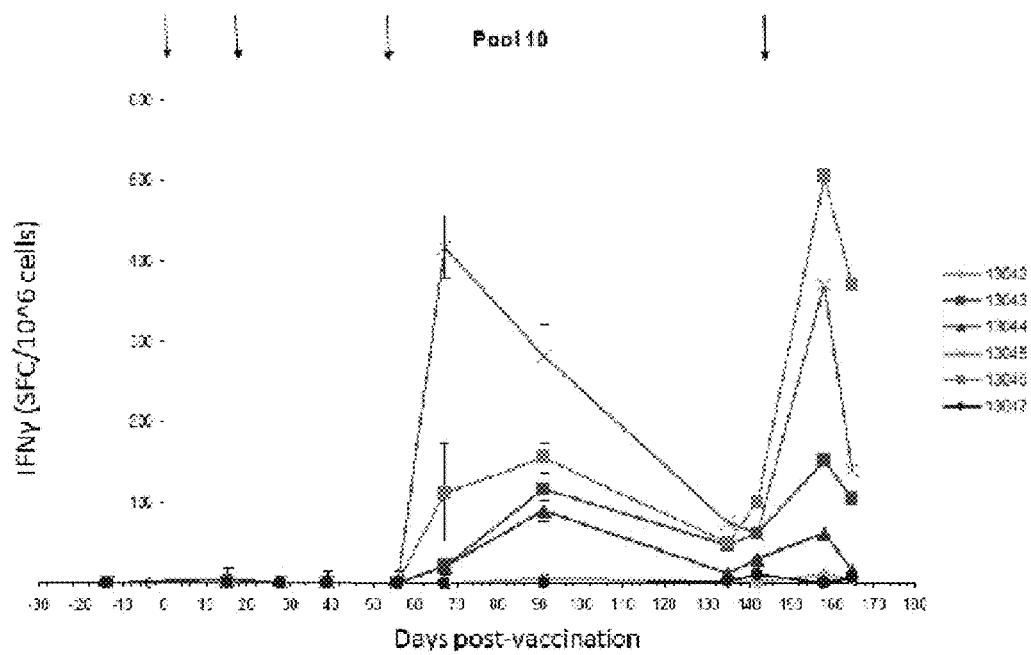

FIGS. 11A and 11B show the kinetics of the specific IFNγ T cell response against pool 6 dTERT peptides, and pool 10 dTERT peptides, respectively.

pDUV5 DNA vaccination at days 57 and 142 show classical long term memory responses, that is rising sharply and decaying more slowly.

Figure 12:
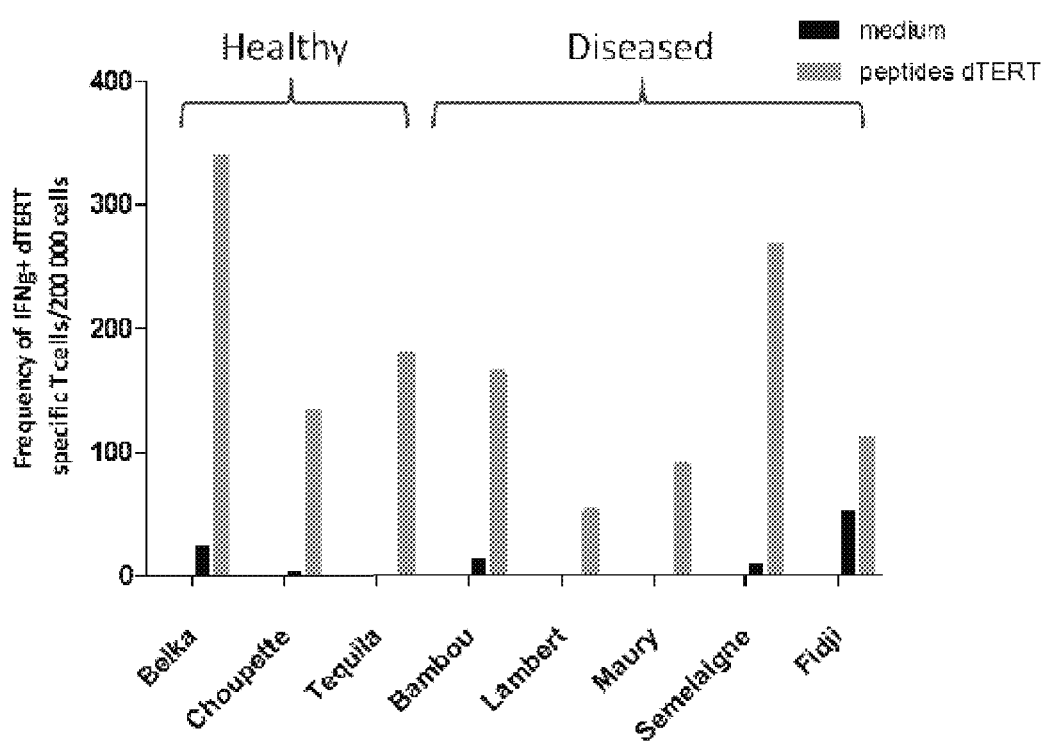

FIG. 12 shows that tumor bearing dogs and healthy dogs have dTERT specific T lymphocytes (pool 4 peptides). Peripheral blood was drawn and in vitro stimulation protocol was performed as described Martinuzzi et al, 2011.

DETAILED DESCRIPTION OF THE INVENTION

Definitions

The telomerase consists of an RNA template and protein components including a reverse transcriptase, designated "Telomerase Reverse Transcriptase" (TERT), which is the major determinant of telomerase activity. Unless otherwise specified, in the present specification, the term "telomerase" refers to TERT.

In the present invention, the term "dog TERT" refers to the TERT sequence of any domestic dog (also designated *Canis familiaris* or *Canis lupus familiaris*). A dog TERT mRNA sequence is available with NCBI accession number NM_001031630 (XM_545191). Dog TERT amino acid sequence is shown as SEQ ID NO:5.

The invention can make also use of non-dog telomerase (TERT) sequence, which can be from any human or non-human mammal, e.g. from cat. The term "cat TERT" refers to the TERT sequence of any domestic cat (also designated as *Felis catus* or *Felis silvestris catus*). Partial molecular cloning of the cat TERT gene (237 bp of mRNA) has been reported by Yazawa et al. 2003. The inventors herein provide a longer sequence of *Felis catus* TERT. The corresponding amino acid sequence is shown as SEQ ID NO:7.

The "telomerase catalytic activity" refers to the activity of TERT as a telomerase reverse transcriptase. The term "deprived of telomerase catalytic activity" means that the nucleic acid sequence encodes a mutant TERT, which is inactive.

The term "hybrid" or "chimeric" amino acid or nucleotide sequence means that part of the sequence originates from one animal species and at least another part of the sequence is xenogeneic, i.e. it originates from at least one other animal species.

When referring to a protein, the term"fragment" preferably refers to fragment of at least 10 amino acids, preferably at least 20 amino acids, still preferably at least 30, 40, 50, 60, 70, 80 amino acid fragments.

In the context of the invention, the term "antigenic fragment" refers to an amino acid sequence comprising one or several epitopes that induce T cell response in the animal, preferably cytotoxic T lymphocytes (CTLs). An epitope is a specific site which binds to a T-cell receptor or specific antibody, and typically comprises about 3 amino acid residues to about 30 amino acid residues, preferably 8 or 9 amino acids as far as class I MHC epitopes are concerned, and preferably 11 to 25 amino acids as far as class II MHC epitopes are concerned.

The term "immunogenic" means that the composition or construct to which it refers is capable of inducing an immune response upon administration (preferably in a dog). "Immune response" in a subject refers to the development of a humoral immune response, a cellular immune response, or a humoral and a cellular immune response to an antigen. A "humoral immune response" refers to one that is mediated by antibodies. A "cellular immune response" is one mediated by T-lymphocytes. It includes the production of cytokines, chemokines and similar molecules produced by activated T-cells. Immune responses can be determined using standard immunoassays and neutralization assays for monitoring specifically the humoral immune response, which are known in the art. In the context of the invention, the immune response preferably encompasses stimulation or proliferation of cytotoxic CD8 T cells and/or CD4 T cells.

As used herein, the term "treatment" or "therapy" includes curative treatment. More particularly, curative treatment refers to any of the alleviation, amelioration and/or elimination, reduction and/or stabilization (e.g., failure to progress to more advanced stages) of a symptom, as well as delay in progression of the tumor or dysplasia or of a symptom thereof.

As used herein, the term "prevention" or "preventing" refers to the alleviation, amelioration and/or elimination, reduction and/or stabilization (e.g., failure to progress to more advanced stages) of a prodrome, i.e. any alteration or early symptom (or set of symptoms) that might indicate the start of a disease before specific symptoms occur. A cell that "overexpresses telomerase" refers to a cell in a subject, which either expresses telomerase, e.g. upon mutation or infection, whereas it does usually not, under normal conditions, or to a cell in a subject which expresses a higher level of telomerase (e.g. upon mutation or infection), when compared to normal conditions. Preferably the cell that overexpresses telomerase shows an increase of expression of at least 5%, at least 10%, at least 20%, 30%, 40%, 50%, 60%, 70%, 80%, or more.

Nucleic Acid Constructs

It is herein provided a nucleic acid that comprises a sequence encoding (i) a dog telomerase reverse transcriptase (TERT) deprived of telomerase catalytic activity, or (ii) a fragment thereof.

The nucleic acid may be DNA or RNA, but is preferably DNA, still preferably double stranded DNA.

As a first safety key, the TERT sequence is deprived of telomerase catalytic activity. In a preferred embodiment, the sequence that encodes dog TERT contains mutations that provide inactivation of the catalytic activity. The term "mutation" includes substitution of one or several amino acids, a deletion of one or several aminoacids, and/or an insertion of one of several amino acids. Preferably the sequence shows a deletion, preferably a deletion of amino acids VDD, as shown on FIG. 1A or 1B.

As a second safety key, the sequence encoding dog TERT can further be deprived of a nucleolar localization signal. This nucleolar localization signal is correlated with the enzymatic activity of TERT. This signal corresponds to the N-terminal 47 amino acids at the N-terminus of the TERT sequence.

Preferably the sequence encoding dog TERT is deleted of N-terminal 47 amino acids with respect to the full-length dog TERT sequence.

Dog TERT sequence deleted of amino acids VDD and of the N-terminal 47 amino acids is shown as SEQ ID NO: 6.

In a particular embodiment, the nucleic acid may encode dog TERT sequence or a fragment thereof only, which preferably corresponds to at least 50%, 55%, 60%, 65%, 70%, 75%, 80%, 85%, 90%, or at least 95% of the dog TERT sequence deleted of the N-terminal 47 amino acids.

Preferably the nucleic acid encodes dog TERT amino acid sequence comprising, or consisting of, SEQ ID NO: 5 or SEQ ID NO: 6.

The nucleic acid may further encode a non-dog TERT antigenic fragment. This embodiment is preferred, to favor breakage of tolerance towards a self-antigen, and induce an efficient immune response along, with an immune memory response in the dog. The presence of non-dog TERT fragment(s) advantageously engages certain subtypes of CD4$^+$ T cells, providing help for anti-tumor immunity, and reversing potential regulation by secreting certain cytokines called Th1 cytokines.

The dog and non-dog TERT sequences or fragments thereof are preferably fused, to be expressed as a hybrid or chimeric protein. Alternatively, the dog and non-dog TERT sequences or fragments thereof may be separated, but carried on the same vector, e.g. the same plasmid.

Preferably the non-dog TERT antigenic fragment corresponds to a fragment absent or eliminated from the dog TERT sequence, to the extent it does not complement the loss of catalytic activity or the loss of the nucleolar localization signal.

The dog TERT sequence, or fragment thereof, can represent at least 30%, 35%, 40%, 45%, 50%, 55%, 60%, 65%, 70%, 75%, 80%, 85%, 90%, or at least 95% of all TERT sequences in the nucleic acid, plasmid, or other vector.

In a preferred embodiment, the dog TERT sequence or fragment represents at least 90% of the hybrid or chimeric TERT protein.

In another embodiment, the dog TERT sequence or fragment represents at least 60% of the hybrid or chimeric TERT protein.

The non-dog TERT antigenic fragment preferably originates from a cat TERT sequence.

The non-dog TERT antigenic fragment is advantageously processed by dendritic cells, thereby generating CD4 T cell help.

In a preferred embodiment, the invention employs a nucleic acid that encodes a protein sequence selected from the group consisting of SEQ ID NO: 2, 4, 5 or 6.

Such nucleic acid may comprise a sequence selected from the group consisting of SEQ ID NO:1 or 3, or nucleotides 241-3459 of SEQ ID NO: 1, or nucleotides 241-1413 or 241-1407 or nucleotides 3352-3456 or 3298-3456 of SEQ ID NO: 3.

In a particular embodiment, the nucleic acid may further encode a protein which enhances the addressing of the TERT protein to the proteasome and increases class I presentation of the derived peptides. Said protein may be preferably ubiquitin, or it may be any chaperon protein, e.g. calreticulin.

Genetic Constructs, Immunogenic Compositions and Administration

Preferably, the nucleic acid is a genetic contrast comprising a polynucleotide sequence as defined herein, and regulatory sequences (such as a suitable promoter(s), enhancer(s), terminator(s), etc.) allowing the expression (e.g. transcription and translation) of the protein product in the host cell or host organism.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, the genetic construct can be prepared by digesting the nucleic acid polymer with a restriction endonuclease and cloning into a plasmid containing a promoter such as the SV40 promoter, the cytomegalovirus (CMV) promoter or the Rous sarcoma virus (RSV) promoter. In a preferred embodiment, the TERT nucleic acid sequences are inserted into a pcDNA3.1 expression plasmid (see FIG. 2A).

Other vectors include retroviral vectors, lentivirus vectors, adenovirus vectors, vaccinia virus vectors, pox virus vectors, adenovirus-associated vectors and measle virus vectors.

Compositions can be prepared, comprising said nucleic acid or vector. The compositions are immunogenic. They can comprise a carrier or excipients that are suitable for administration in dogs (i.e. non-toxic, and, if necessary, sterile). Such excipients include liquid, semisolid, or solid diluents that serve as pharmaceutical vehicles, isotonic agents, stabilizers, or any adjuvant. Diluents can include water, saline, dextrose, ethanol, glycerol, and the like. Isotonic agents can include sodium chloride, dextrose, mannitol, sorbitol, and lactose, among others. Stabilizers include albumin, among others. Any adjuvant known in the art may be used in the vaccine composition, including oil-based adjuvants such as Freund's Complete Adjuvant and Freund's Incomplete Adjuvant, mycolate-based adjuvants, bacterial lipopolysaccharide (LPS), peptidoglycans, proteoglycans, aluminum hydroxide, saponin, DEAE-dextran, neutral oils (such as miglyol), vegetable oils (such as arachis oil), Pluronic® polyols.

The nucleic acid or composition can be administered directly or they can be packaged in liposomes or coated onto colloidal gold particles prior to administration. Techniques for packaging DNA vaccines into liposomes are known in the art, for example from Murray, 1991. Similarly, techniques for coating naked DNA onto gold particles are taught in Yang, 1992, and techniques for expression of proteins using viral vectors are found in Adolph, 1996.

For genetic immunization, the vaccine compositions are preferably administered intradermally, subcutaneously or intramuscularly by injection or by gas driven particle bombardment, and are delivered in an amount effective to stimulate an immune response in the host organism. In a preferred embodiment of the present invention, administration comprises an electroporation step, also designated herein by the term "electrotransfer", in addition to the injection step (as described in Mir 2008, Sardesai and Weiner 2011).

The compositions may also be administered ex vivo to blood or bone marrow-derived cells using liposomal transfection, particle bombardment or viral transduction (including co-cultivation techniques). The treated cells are then reintroduced back into the subject to be immunized While it will be understood that the amount of material needed will depend on the immunogenicity of each individual construct and cannot be predicted a priori, the process of determining the appropriate dosage for any given construct is straightforward. Specifically, a series of dosages of increasing size, starting at about 5 to 30 μg, or preferably 20-25 μg, up to about 500 μg for instance, is administered to the corresponding species and the resulting immune response is observed, for example by detecting the cellular immune response by an IFNγ Elispot assay (as described in the experimental section), by detecting CTL response using a chromium release assay or detecting CD4 T cell (helper T cell) response using a cytokine release assay.

In a preferred embodiment, the vaccination regimen comprises one to three injections, preferably repeated three or four weeks later.

In a particular embodiment, the vaccination schedule can be composed of one or two injections followed three or four weeks later by at least one cycle of three to five injections. In another embodiment, a primer dose is composed of one to three injections, followed by at least a booster dose every year, or every two or years for instance.

Prevention and Treatment of Tumors

The nucleic acid or immunogenic composition as described above is useful in a method for preventing or treating a tumor in a dog.

A method for preventing or treating a tumor in a dog is described, which method comprises administering an effective amount of said nucleic acid or immunogenic composition in a dog in need thereof. Said nucleic acid or immunogenic composition is administered in an amount sufficient to induce an immune response in the dog.

The tumor may be any undesired proliferation of cells, in particular a benign tumor or a malignant tumor, especially a cancer.

The cancer may be at any stage of development, including the metastatic stage. However preferably the cancer has not progressed to metastases.

In particular the tumor may be selected from the group consisting of bladder cancer, brain tumor, liver tumor, mammary tumors and carcinoma, mast cell tumors, malignant histiocytosis and histocytic sarcomas, squamous cell carcinomas, hemangiosarcoma, lymphoma, in particular B-cell lymphoma, melanoma, bone tumors (osteosarcoma), testicular tumors.

In a particular embodiment, the vaccination according to the invention may be combined with conventional therapy, including chemotherapy, radiotherapy or surgery. Combinations with adjuvant immunomodulating molecules such GM-CSF or IL-2 could also be useful.

The Figures and Examples illustrate the invention without limiting its scope.

EXAMPLES

The inventors have constructed DNA vaccines encoding an inactivated form of dog TERT and a cat/dog hybrid TERT (Example 1), and have assessed their functionality, safety and immunogenicity.

They have demonstrated that the plasmids were correctly processed in vitro after transfection in mammalian cells and that the plasmid product of expression (TERT protein) was well expressed. Moreover, no enzymatic activity was detected and TERT proteins were found excluded for the transfected cells nucleoli, which evidences safety of the constructs (Example 2).

Then, the plasmids were found to be immunogenic and to elicit specific efficient CD8 T cells and CD4 T cells in mice (Example 3).

Example 1: Construction of the DNA Plasmids

In all constructs, the TERT sequence is preceded by a DNA sequence encoding the human-ubiquitin. The presence of the ubiquitin will increase the addressing of the TERT protein to the proteasome and increase the class I presentation pathway of TERT derived peptides. TERT sequence is followed by the sequence of the influenza protein V5 to facilitate future purification or detection of the fusion protein by Western Blot or histochemistry for example. The DNA sequence coding for the TERT protein has been deleted of 47 amino-acids in the N-Ter region, which encodes the nucleolar importation signal. Moreover, three amino-acids have been removed in the catalytic site of TERT (VDD), to inhibit the protein enzymatic activity.

pDUV5 encodes the full-length of dog TERT nucleotide sequence, depleted of the N-term 47 amino acids (FIG. 1A), pCDT encodes 54.4% of the cat TERT sequence and 35.9% of the dog TERT sequence (FIG. 1B).

All TERT DNA sequences were synthesized from Genecust (Dudelange, Luxembourg). Then they were cloned into the pcDNA3,1 expression plasmid provided by Life technologies SAS (Saint-Aubin, France) using the HindIII and XbaI restriction sites (see FIG. 2A). Plasmids were stored at −20° C., in PBS 1×, at a concentration of 2 mg/mL prior use. The backbone plasmid was used as empty vector for western blot and Trap-Assay experiments. It consists of the pcDNA3.1 backbone plasmid deprived of the transgene protein DNA sequence (TERT).

Example 2: Functionality and Safety of the Plasmids 2.1. Materials and Methods

Cell Culture

The human 293T cell line used for transfection assays and immune-fluorescence experiments were kindly provided by Pr Simon Wain-Hobson (Pasteur Institute). The CrFK (Crandall-Reese feline kidney) cells used for the TRAP-assay were kindly provided by Pr J. Richardson (Ecole Vétérinaire de Maison Alfort). Cells were grown at 37° C., 5% $CO_2$ in Dulbecco's Modified Eagle Medium (DMEM) supplemented with 10% heat-inactivated Fetal Calf Serum (FCS), 1% sodium-pyruvate, 1% penicillin-streptomycin pyruvate and 0.1% β-mercaptoethanol. All components of the culture medium were purchased from Life technologies SAS (Saint-Aubin, France).

Transfection Assays

Transfection of 293T cells were performed with either pCDT or pDUV5 plasmids using the JetPRIME® transfection kit (Polyplus-transfection SA, Illkirch, France) according to manufacturer's instruction. In a 6-well plate, 400 000 HeLa cells or 293T cells per well were seeded in 2 mL of DMEM culture medium, and cultured 24 hours at 37° C., 5% $CO_2$ prior transfection. For each well, 2 µg of each plasmid diluted in 200 µL of jetPRIME® buffer, or 200 µL of jetPRIME® buffer only with respectively 4 µL of jetPRIME® agent were drop onto the cells. Transfection medium were removed 4 hours later and replaced by 2 mL of DMEM culture medium. Cells were put at 37° C., 5% $CO_2$ and recovered for analysis 24 hours later.

Western Blots

Transfected 293 T cells were lysed on ice with radioimmunoprecipitation assay (RIPA) lysis buffer (RIPA Buffer, Sigma Aldrich chimie SARL, Saint-Quentin Fallavier, France) containing protease inhibitors cocktail (Complete EDTA-free, Roche Diagnostic, Indianapolis, USA) for 10-20 minutes. Then, suspension was centrifuged 15 minutes at 14000 rpm at 4° C. in order to remove cellular debris. The supernatants were harvested and the protein concentration was measured using the Bradford method. Protein samples were denatured 5 minutes at 95° C., separated on Nu-PAGE® Novex 4-12% Bis-Tris gels (Invitrogen, Carlsbad, USA) and transferred to PVDF membranes (iBlot® transfer stack, Invitrogen, Carlsbad, USA) using the iBlot® device (Invitrogen, Carlsbad, USA). The membrane was cut approximately at 60 kDa. First, the upper part membrane was probed with an anti-V5 antibody (Invitrogen, Carlsbad, USA) while the other part was probed with an anti-(β-actin antibody (Sigma Aldrich chimie SARL, Saint-Quentin Fallavier, France), then samples were revealed by an ECL (Enhanced chemiluminescence) anti-mouse Horse Radish Peroxidase (HRP) linked antibody (GE Healthcare, Vélizy, France)) Immunoblot signals were reveled using 18×24 films and the corresponding cassette both products purchased from GE healthcare (Buckinghamshire, UK).

Immunofluorescence and Microscopy

Human 293T cells were seeded on 8-well Lab-Tek® chamber slides (Sigma Aldrich chimie SARL, Saint-Quentin Fallavier, France) at $20.10^3$ cells/well in 200 µL of culture medium and incubated overnight at 37° C. The next day, culture medium was discarded. Ten µL of a mix solution containing 1 µg of either pCDT or PUF2 plasmid, 50 µL of OptiMEM (Life technologies SAS, Saint-Aubin, France) and 2.5 µL of Fugene HD (Promega France, Charbonnières-les-bains, France) were added to the corresponding chamber. As control, $20.10^3$ HeLa cells were incubated with the 10 µL of the same mix without plasmid. Chamber slides were left in the incubator for 24 hours. Transfected 293T cells were carefully washed with PBS 1× and 200 µL 2% PFA were added to each well for 10 minutes at +4° C., in order to fix and permeabilize the cells. Then wells were washed two times with PBS 1× 0.05% Tween®20 and 293T cells were incubated 30 minutes at room temperature with 200 µL of Blocking solution (0.5% TritonX100; 3% BSA; 10% Goat Serum). Eventually, wells were incubated for 1.5 hours at room temperature with a primary mouse anti-V5 antibody (Life technologies SAS, Saint-Aubin, France) diluted in blocking solution at ½00, with slight agitation. After three washes in PBS 1× 0.05% Tween®20, a secondary goat anti-mouse-Alexa Fluor 488® antibody (Life technologies SAS, Saint-Aubin, France) diluted in blocking solution (⅕00) was put in the wells for 45 minutes at room temperature away from light and under slight agitation. Wells were washed three times with PBS 1× 0.05% Tween®20 and mounted with the Vectashield® mounting medium containing DAPI (Vector laboratories, Peterborough, UK). Slides were analyzed with a fluorescence microscope (Axio observer Z1, Carl Zeis MicroImaging GmbH, Jena, Germany) equipped with an image processing and analysis system (Axiovision, Carl Zeis MicroImaging GmbH, Jena, Germany).

TRAP Assay

Telomerase activity was measured by the photometric enzyme immunoassay for quantitative determination of telomerase activity, utilizing telomeric repeat amplification protocol (TRAP) (Yang et al, 2002). CrFK (Crandell Rees Feline Kidney) telomerase-negative cells (Yazawa et al., 2003) were transfected with plasmids encoding pDUV5, or pCDT TERT constructs. As a positive control CrFK cells were transfected with a plasmid encoding the wild type human TERT (fully active). Briefly, 24 hours after transfection, CrFK cells were harvested by mechanical scraping and then washed twice with 1 mL PBS and pelleted by centrifugation 5 minutes at 3000 g, at 4° C. Telomerase activity was assessed by TRAP-ELISA assay using the TeloTAGGG Telomerase PCR ELISAPLUS kit (Roche Diagnostics, Germany) according to the manufacturer's instructions. The protein concentration in the cell extract was measured by the Bradford method (Bio-Rad Laboratories). Three microliters of the cell extract (equivalent to 2.1, 0.21, 0.021 µg) was incubated in a Polymerase Chain reaction (PCR) mixture provided in the kit. The cycling program was performed with 30 minutes primer elongation at 25° C. and then the mixture was subjected to 30 cycles of PCR consisting of denaturation at 94° C. for 30 sec, annealing at 50° C. for 30 sec, polymerization at 72° C. for 90 sec and final extension at 72° C. for 10 minutes. 2.5 µl of amplification product was used for ELISA according to the manufacturer's instructions. The absorbance at 450 nm (with a reference of 690 nm) of each well was measured using Dynex MRX Revelation and Revelation TC 96 Well Microplate Reader.

Telomerase activity was calculated as suggested in the kit's manual and compared with a control template of 0.1 amol telomeric repeats, representing a relative telomerase activity (RTA) of 100. Inactivated samples and lysis buffer served as negative controls.

2.2. Results

New TERT Encoding Plasmids are Functional in vitro after Transfection

The functionality of the new plasmid constructs is shown by the presence of the plasmid encoded TERT protein in the total protein lysate of pCDT or pDUV5 transfected cells in vitro. The inventors performed western-blot assays on the total protein lysate of 293T cells plasmids transfected with pCDT or pDUV5 (24 h after transfection). As the TERT protein sequence encoded by each plasmid was tagged with the V5 protein sequence, anti-V5 antibody coupled with Horse Radish Peroxidase (HRP) was used to reveal the presence of the fusion protein of interest.

A highly positive V5 specific-signal was detected 24 h after transfection in the protein lysate of pCDT or pDUV5 transfected cells. The size of the protein band detected corresponds to the different TERT protein encoded by the plasmids which molecular weight is 123 kDa. Moreover no V5 specific signal was detected in untreated or empty plasmid transfected cells. The inventors demonstrated that pDUV5 and pCDT plasmids were correctly processed in vitro after transfection in mammalian cells and that the plasmid product of expression (TERT protein) was well expressed.

New TERT Encoding Plasmids Express a Non-Functional Enzyme of which Cellular Expression is Excluded from the Nucleoli after in vitro Transfection To test the absence of enzymatic activity, a TRAPeze assay was performed. As illustrated by FIG. 3, protein lysates from pDUV5 or pCDT transfected cells do not exhibit any telomerase activity. As a positive control, the protein extracts from CrFk cells transfected with the native human TERT (hTERT) were used. Thus the inventors demonstrated that the TERT proteins encoded by either pCDT or pDUV5 plasmids do not express any functional enzymatic activity after in vitro transfection.

The inventors have further investigated the intracellular location of the two plasmid products of expression. To this aim, an in vitro immunofluorescence assay was performed. Briefly, 24 h after in-vitro transfection of 293T cells with either pCDT or pDUV5, an anti-V5 antibody coupled to an Alexa-Fluor labeled secondary antibody were used to detect the TERT proteins within the cells. The pCDT and pDUV5 encoded TERTs were not detected inside the cell nucleoli contrary to what was observed with 293T cells transfected with the plasmid encoding the native human TERT.

To conclude, the inventors demonstrated that after in vitro transfection with either pDUV5 and pCDT plasmids, first the TERT protein expression is excluded from the nucleoli and secondly, these products of expression do not exhibit any enzymatic activity. These two criteria establish the safety of the plasmids and favour their use for in vivo vaccination.

Example 3: In Vivo Immune Response

3.1. Materials and Methods

Mice

Female Balb/cBy and C57BL/6J mice (6-8 week old) were purchased from Janvier laboratories (Saint-Berthevin, France). Animals were housed at the Specific Pathogen Free animal facility of the Pasteur Institute. Mice were anesthetized prior to intradermal (ID) or intramuscular (IM) immunizations, with a mix solution of xylazine 2% (Rompun, Bayer Santé, Loos, France) and Ketamine 8% (Imalgen 1000, Merial, Lyon, France) in Phosphate Buffer Saline 1× (PBS 1×, Life technologies SAS, Saint-Aubin, France), according to individual animal weight and duration of anesthesia (intraperitoneal route). All animals were handled in strict accordance with good animal practice and complied with local animal experimentation and ethics committee guidelines of the Pasteur Institute of Paris.

H2 Restricted Peptides

TERT peptides used in mouse studies (IFNγ ELIspot) were predicted by in-silico epitope prediction in order to bind mouse class I MHC, H2K$^b$, H2D$^b$ or mouse class II H2-IA$^d$ using four algorithms available online:

Syfpeithi (http://www.syfpeithi.de/), Bimas (http://www-bimas.cit.nih.gov/), NetMHCpan and SMM (http://tools.immuneepitope.org/main/).

All synthetic peptides were purchased lyophilized (>90% purity) from Proimmune (Oxford, United Kingdom). Lyophilized peptides were dissolved in sterile water at 2 mg/mL and stored in 35 μL aliquots at −20° C. prior use. Details of peptides sequence and H2 restriction is shown in table 1.

TABLE 1

H2 restricted peptides sequences determined by in silico prediction algorithms

| H2D$^b$ restricted TERT peptides | | |
|---|---|---|
| 621-629 (RPIVNMDYI) | 621 | SEQ ID NO: 8 |
| 580-589 (RQLFNSVHL) | 580 | SEQ ID NO: 9 |
| 987-996 (TVYMNVYKI) | 987 | SEQ ID NO: 10 |
| H2-IA$^d$ restricted TERT peptides | | |
| 1106-1121 (CLLGPLRAAKAHLSR) | 1106 | SEQ ID NO: 11 |
| 1105-1120 (RCLLGPLRAAKAHLS) | 1105 | SEQ ID NO: 12 |

TABLE 1-continued

H2 restricted peptides sequences determined by in silico prediction algorithms

| 951-966 (YSSYAQTSIRSSLTF) | 951 | SEQ ID NO: 13 |
|---|---|---|
| 1109-1124 (GPLRAAKAHLSRQLP) | 1109 | SEQ ID NO: 14 |

Mice Immunization and in vivo Electroporation

Intradermal (ID) immunization was performed on the lower part of the flank with Insulin specific needles (U-100, 29G×½"–0.33×12 mm, Terumo, Belgium) after shaving. No erythema was observed after shaving, during and after immunization procedure. Intramuscular immunization (IM) was performed in the anterior tibialis cranialis muscle, also using Insulin specific needles U-100. Each animal received a priming dose of either pCDT or pDUV5, independently of vaccine route, corresponding to 100 μg of DNA. All animals were boosted at day 14 post-prime using the same amount of plasmid and the same route of immunization. Directly after ID vaccination, invasive needle electrodes (6×4×2, 47-0050, BTX, USA) are inserted into the skin so that the injection site is placed between the two needle rows (the two needle rows are 0.4 cm apart). Two pulses of different voltages were applied (HV-LV): HV=1125 V/cm (2 pulses, 50 μs-0.2 μs pulse interval) and LV=250 V/cm (8 pulses, 100 V-10 ms-20 ms pulse interval). Immediately after IM immunization the muscle injection site was covered with ultrasonic gel (Labo FH, blue contact gel, NM Médical, France) and surrounded by tweezers electrodes (0.5 cm apart, tweezertrode 7 mm, BTXI45-0488, USA) and voltage was applied using the same parameters than for skin electroporation. The Agilepulse® in vivo system electroporator was used for all experiments (BTX, USA). For each route of immunization (IM, ID) control mice were treated with the same procedures using the same volume of PBS 1×.

IFNγ ELispot Assay

Briefly, PVDF microplates (IFN-γ Elispot kit, Diaclone, Abcyss, France, 10×96 tests, ref 862.031.010P) were coated overnight with capture antibody (anti-mouse IFN-γ) and blocked with PBS 2% milk. Spleens from pDNA-immunized mice were mashed and cell suspensions were filtered through a 70-mm nylon mesh (Cell Strainer, BD Biosciences, France). Ficoll-purified splenocytes (Lymphocyte Separation Medium, Eurobio, France) were numerated using the Cellometer® Auto T4 Plus counter (Ozyme, France) and added to the plates in triplicates at 2×10$^5$ or 4×10$^5$ cells/well and stimulated with 5 μg/ml of dTERT or hyTERT relevant peptides or Concanavalin A (10 μg/ml), or mock stimulated with serum free culture medium. After 19 hours, spots were revealed with the biotin-conjugated detection antibody followed by streptavidin-AP and BCIP/NBT substrate solution. Spots were counted using the Immunospot ELIspot counter and software (CTL, Germany).

Dog TERT peptide pools
The vast majority of peptides were 15 residues long. A few are 14 amino acids long.

Pool 2

PQKPGAARRMRRLPA (SEQ ID NO: 15), GAARRMRRLPARYWR (SEQ ID NO: 16), RMRRLPARYWRMRPL (SEQ ID NO: 17),
LPARYWRMRPLFQEL (SEQ ID NO: 18), YWRMRPLFQELLGNH (SEQ ID NO: 19), RPLFQELLGNHARCP (SEQ ID NO: 20),
QELLGNHARCPYRAL (SEQ ID NO: 21), GNHARCPYRALLRTH (SEQ ID NO: 22), RCPYRALLRTHCPLR (SEQ ID NO: 23),
RALLRTHCPLRAMAA (SEQ ID NO: 24), RTHCPLRAMAAKEGS (SEQ ID NO: 25), PLRAMAAKEGSGNQA (SEQ ID NO: 26),
MAAKEGSGNQAHRGV (SEQ ID NO: 27), EGSGNQAHRGVGICP (SEQ ID NO: 28), NQAHRGVGICPLERP (SEQ ID NO: 29),
RGVGICPLERPVAAP (SEQ ID NO: 30), ICPLERPVAAPQEQT (SEQ ID NO: 31), PQKPGAARRMRRLPA (SEQ ID NO: 32)

Dog TERT peptide pools
The vast majority of peptides were 15 residues
long. A few are 14 amino acids long.

Pool 4

AKLSLQELTWKMKVR (SEQ ID NO: 33), LQELTWKMKVRDCTW (SEQ ID NO: 34), TWKMKVRDCTWLHGN (SEQ ID NO: 35),
KVRDCTWLHGNPGAC (SEQ ID NO: 36), CTWLHGNPGACCVPA (SEQ ID NO: 37), HGNPGACCVPAAEHR (SEQ ID NO: 38),
GACCVPAAEHRRREE (SEQ ID NO: 39), VPAAEHRRREEILAR (SEQ ID NO: 40), EHRRREEILARFLVL (SEQ ID NO: 41),
REEILARFLVLVDGH (SEQ ID NO: 42), LARFLVLVDGHIYVV (SEQ ID NO: 43), LVLVDGHIYVVKLLR (SEQ ID NO: 44),
DGHIYVVKLLRSFFY (SEQ ID NO: 45), YVVKLLRSFFYVTET (SEQ ID NO: 46), LLRSFFYVTETTFQK (SEQ ID NO: 47),
FFYVTETTFQKNRLF (SEQ ID NO: 48), TETTFQKNRLFFYRK (SEQ ID NO: 49), FQKNRLFFYRKSVW (SEQ ID NO: 50)

Pool 6

EGGPPGTRPTTPAWH (SEQ ID NO: 51), PGTRPTTPAWHPYPG (SEQ ID NO: 52), PTTPAWHPYPGPQGV (SEQ ID NO: 53),
AWHPYPGPQGVPHDP (SEQ ID NO: 54), YPGPQGVPHDPAHPE (SEQ ID NO: 55), QGVPHDPAHPETKRF (SEQ ID NO: 56),
HDPAHPETKRFLYCS (SEQ ID NO: 57), HPETKRFLYCSGGRE (SEQ ID NO: 58), KRFLYCSGGRERLRP (SEQ ID NO: 59),
YCSGGRERLRPSFLL (SEQ ID NO: 60), GRERLRPSFLLSALP (SEQ ID NO: 61), LRPSFLLSALPPTLS (SEQ ID NO: 62),
FLLSALPPTLSGARK (SEQ ID NO: 63), ALPPTLSGARKLVET (SEQ ID NO: 64)

Pool 10

DCTWLHGNPGACCVP (SEQ ID NO: 65), LHGNPGACCVPAAEH (SEQ ID NO: 66), PGACCVPAAEHRRRE (SEQ ID NO: 67),
CVPAAEHRRREEILA (SEQ ID NO: 68), AEHRRREEILARFLV (SEQ ID NO: 69), RREEILARFLVLVDG (SEQ ID NO: 70),
ILARFLVLVDGHIYV (SEQ ID NO: 71), FLVLVDGHIYVVKLL (SEQ ID NO: 72), VDGHIYVVKLLRSFF (SEQ ID NO: 73),
IYVVKLLRSFFYVTE (SEQ ID NO: 74), KLLRSFFYVTETTFQ (SEQ ID NO: 75), SFFYVTETTFQKNRL (SEQ ID NO: 76),
VTETTFQKNRLFFYR (SEQ ID NO: 77), TFQKNRLFFYRKSVW (SEQ ID NO: 78)

Pool 19

QLPFNQPVRKNPSFF (SEQ ID NO: 79), NQPVRKNPSFFLRVI (SEQ ID NO: 80), RKNPSFFLRVIADTA (SEQ ID NO: 81),
SFFLRVIADTASCCY (SEQ ID NO: 82), RVIADTASCCYSLLK (SEQ ID NO: 83), DTASCCYSLLKARNA (SEQ ID NO: 84),
CCYSLLKARNAGLSL (SEQ ID NO: 85), LLKARNAGLSLGAKG (SEQ ID NO: 86), RNAGLSLGAKGASGL (SEQ ID NO: 87),
LSLGAKGASGLFPSE (SEQ ID NO: 88), AKGASGLFPSEAARW (SEQ ID NO: 89), SGLFPSEAARWLCLH (SEQ ID NO: 90),
PSEAARWLCLHAFL (SEQ ID NO: 91), ARWLCLHAFLLKLAH (SEQ ID NO: 92)

In vivo Cytotoxicity Assay

Briefly, for target cell preparation, splenocytes from naïve C57/B16 mice were labeled in PBS 1× containing high (5 µM), medium (1 µM) or low (0.2 µM) concentrations of CFSE (Vybrant CFDA-SE cell-tracer kit; Life technologies SAS, Saint-Aubin, France). Splenocytes labeled with 5 and 1 µM CFSE were pulsed with 2 different H2 peptides at 5 µg/ml for 1 hour and 30 minutes at room temperature. Peptides 987 and 621 were used for pulsing respectively CFSE high and medium labeled naïve splenocytes. CFSE low labeled splenocytes were left unpulsed. Each mouse previously immunized with either pCDT or pDUV5 received at day 10 post-boost injection $10^7$ CFSE-labeled cells of a mix containing an equal number of cells from each fraction, through the retro-orbital vein. After 15-18 hours, single-cell suspensions from spleens were analyzed by flow cytometry MACSQUANT® cytometer (Miltenyii, Germany).

The disappearance of peptide-pulsed cells was determined by comparing the ratio of pulsed (high/medium CFSE fluorescence intensity) to unpulsed (low CFSE fluorescence intensity) populations in pDNA immunized mice versus control (PBS 1× injected) mice. The percentage of specific killing per test animal was established according to the following calculation:

$$[1-[\text{mean } (CFSE^{low}PBS/CFSE^{high/medium}PBS)/(CFSE^{low}pDNA/CFSE^{high/medium}pDNA)]] \times 100.$$

Statistical Analysis and Data Handling

Prism-5 software was used for data handling, analysis and graphic representations. Data are represented as the mean±standard deviation. For statistical analyses of EliSPOT assays we used a Mann Whitney non parametric test, and a Kruskal-Wallis analysis with Dunn's multiple comparison test for in-vivo cytotoxicity assay. Significance was set at p-value<0.05.

3.2. Results pDUV5 Induces a Strong Cytotoxic CD8 T Cell Response after ID or IM Immunization and EP in Mice The inventors have assessed whether pDUV5 plasmid DNA plasmid was capable of eliciting efficient cellular immune responses (CD8) in mice. To this aim, different groups of 9-10 C57-B⅙ mice were injected ID or IM with pDUV5 immediately followed by electroporation. Two weeks later, mice received a boost injection with the same protocol. On day 10 post-boost, mice spleens were harvested and the induced immune response was monitored via an IFN-γ ELISPOT assay using H2 restricted peptides described in Table 1. Dog TERT peptides restricted to mouse MHC class I were predicted in silico as described in the material and methods section. As shown in FIG. 4, a significant augmentation in the frequency of dTERT specific IFN-γ secreting CD8 T-cells was observed in the spleen of ID and IM vaccinated animals in comparison with control mice. This was observed for 2 out of 3 peptides (p621 and p987) (p<0.05). No significant difference was observed between the 2 routes of administration.

pDUV5 construct is able to promote the expansion of dTERT specific CD8 T-cells in mice. The inventors next wanted to show that those specific T-cells exhibit a functional cytotoxic activity in vivo, which will be necessary to attack tumor cells. In order to measure the in vivo cytolytic strength of the CD8+ T-cell response elicited by pDUV5 immunization, the inventors performed in vivo cytotoxicity tests using carboxyfuorescein-diacetate succinimidyl ester (CFSE)—labelled, peptide-pulsed splenocytes as target cells. 7 week old C57/B16 mice which received a prime and boost vaccination with pDUV5 via the ID or IM route as described before or mock-immunized with phosphate-buffered saline (PBS) were intravenously injected with 10⁷ target cells. Target cells were splenocytes from naïve congenic mice separately labelled with three different concentrations of CFSE and pulsed with individual peptides (p621 or p987) or left un-pulsed as an internal control. After 15-18 hours, spleen cells were obtained and the disappearance of peptide-pulsed cells in control versus immunized mice was quantified by fluorescence-activated cell sorting.

Results show that mice develop CTLs against the 2 epitopes predicted in silico (FIGS. 5A and 5B). Peptide 621 gives the strongest in vivo lysis. Results were concordant with IFN-γ Elispot assays (FIG. 4). No significant difference was observed between the two routes of immunization.

pCDT Induces a Strong Cytotoxic CD8 T Cell Response Along with a Specific CD4 T Cell Response after ID or IM Immunization and Electroporation in Mice In light of the importance of cytotoxic CD8 T cells in antitumor immune responses, the inventors have assessed whether plasmid pCDT was able to promote such an immune response in vivo. Thus, different groups of 9-10 C57-B⅙ mice were immunized with pCDT by ID or IM injection of the plasmid immediately followed by electroporation. Two weeks later, mice received a boost injection with the same protocol. On day 10 post-boost, mice spleens were harvested and the induced immune response was monitored via an IFN-γ ELISPOT assay using H2 restricted peptides described in Table 1.

Hy-TERT peptides restricted to mouse MHC class I were predicted in silico as described in the material and methods section. As shown in FIG. 6A, a significant augmentation in the frequency of hyTERT specific IFN-γ secreting CD8 T-cells was observed in the spleen of ID and IM vaccinated animals in comparison with control mice. This was observed for 2 out of 3 class I restricted peptides (p621 and p987, p<0.05). No significant difference in the frequency of specific CD8 T cells was observed between IM and ID route for both peptides p921 and p987.

The inventors have further investigated the hyTERT restricted CD4 T cell response. To this aim, 9-10 Balb/C mice were immunized with pCDT by ID or IM injection immediately followed by electroporation and the CD4 specific T cell response was monitored in the spleen as described before using hyTERT IA$^d$ restricted peptides (in silico prediction). Balb/C mice were chosen because this mouse strain is known to develop good CD4 T cell responses. As shown in FIG. 6B, when performing the IFN-γ ELISPOT assay, a significant augmentation in the frequency of hyTERT specific IFN-γ secreting CD4 T-cells was observed in the spleen of ID and IM vaccinated Balb/C mice in comparison with control mice injected with PBS 1×. This was observed for 2 out of 3 class I restricted peptides (p1106 and p1105, with respectively for p1106 p<0.05 for ID route and p<0.001 for IM route and for 1105 the difference was not significant for ID route and p<0.01 for IM route). No significant difference in the frequency of specific CD4 T cells was observed between IM and ID route for both peptides p1105 and p1106.

Thus, pCDT construct is able to promote the expansion of hyTERT specific CD8 and CD4 T-cells in mice. The inventors next wanted to show that hyTERT specific CD8 T-cells exhibit a functional cytotoxic activity in vivo, which will be necessary to destroy tumor cells. In order to measure the in vivo cytolytic strength of the CD8+ T-cell response elicited by pCDT immunization, the inventors performed an in vivo cytotoxicity test using carboxyfluorescein-diacetate succinimidyl ester (CFSE)—labelled, peptide-pulsed splenocytes as target cells. 7 week old C57/B16 mice which received a prime and boost vaccination with pCDT via the ID or IM route as described before or mock-immunized with phosphate-buffered saline (PBS) were intravenously injected with 10⁷ target cells. Target cells were splenocytes from naïve congenic mice separately labelled with three different concentrations of CFSE and pulsed with individual peptides (p621 or p987) or left un-pulsed as an internal control. After 15-18 hours, spleen cells were obtained and the disappearance of peptide-pulsed cells in control versus immunized mice was quantified by fluorescence-activated cell sorting.

Results show that mice develop CTLs against the 2 peptides p621 and p987 which were predicted in silico. Peptide 987 gives the strongest in vivo lysis. Results were consistent with the ones from the IFN-γ Elispot assays (FIG. 6A). It is worth mentioning that for p621, the mean percent lysis was slightly superior when pCDT was injected via the ID route (mean ID=7.7% vs mean IM=0.2%), however, no significant difference was observed between the two routes of immunization.

Example 4: Dog TERT Specific T Cell Repertoire 4.1. Materials and Methods
Dog TERT Peptides Library Lyophilized dTERT peptides (purity>90%) were purchased from JPT Peptide Technologies (Berlin, Germany). Each peptide was resuspended in distilled H₂O, 5% DMSO at 2 mg/mL prior use according to supplier recommendation and kept frozen at −20° C. before use. One third of the dog TERT peptide (AA 281 to 571) was used to synthesized 70 peptides of 15 AA overlapping of 11 AA and recovering this sequence of the dog TERT as depicted in FIG. 3. Four pools of peptides were used for in vitro experiments and ELIspot assays in dogs.

Canine Blood Products

Canine blood samples were purchased from the Bourgelat Institute (Marcy l'Etoile, France). It was taken from a healthy 4-year-old beagle dog housed, fed and cared for in accordance with institutional and ethical guidelines. Heparinized blood samples was 4 time diluted in PBS 1× (Life technologies SAS, Saint-Aubin, France). Diluted samples were then layered on Lymphocyte Separation Medium (Eurobio, Courtaboeuf, France) and centrifuged 30 minutes at 2200 rpm (at room temperature) without break. Canine PBMCs were harvested and stored in Fetal Calf Serum (FCS, PAA Laboratories GmbH, Pashing, Austria) with 10% DMSO (Sigma Aldrich chimie SARL, Saint-Quentin Fallavier, France) in liquid nitrogen prior use.

In vitro Immunization Assays in Dogs PBMCs

On day 0, dog frozen PBMCs were recovered, counted using the Cellometer® Auto T4 Plus counter (Ozyme, France) and plated in duplicates or triplicates at 10⁶ cells/mL in 48-well flat-bottomed plates (BD, France) in AIM-V medium (Invitrogen) supplemented with either 100 ng/mL caGM-CSF and 5 ng/mL caIL-4 (R&DSystems) or 50 ng/mL human FlT3 L (Immunotools). Cells were cultured at 37° C., 5% CO₂ in an incubator.

After 24 hours (day 1), maturation stimuli were added, comprising the following reagent: 50 ng/mL rcTNFα, 20 ng/mL rcIL1-β (R&DSystems), 1 ng/mL hIL-7 (Miltenyi). Pools of peptides were also added. The final concentration used for each peptide was 10 µg/mL. Control wells received the cocktails of maturation cytokines only and no peptide. At day 3, culture medium was discarded and fresh AIM-V was added. Fresh AIM-V was added every 3 days until the day of testing. At either day 11 or day 18 after the beginning of culture, cells were recovered, washed in fresh AIM-V medium and used for the ELIspot assay.

Briefly cells were plated with the 4 pools of peptides (5 µg/mL of each peptide) in AIMV-5 or in AIMV only. Concanavalin A (10 µg/ml) and recombinant canine IFN-γ (16 ng/mL) was used for positive control wells. After 24 hours, spots were revealed with the biotin-conjugated detection antibody followed by streptavidin-AP and BCIP/NBT substrate solution. Spots were counted using the Immunospot ELIspot counter and software (CTL, Germany).

4.2. Results

In order to highlight the relevance of the vaccine technology of the invention, the inventors wanted to demonstrate the existence of a pre-existing dogTERT specific T-cell repertoire in the target species, i.e. dogs.

The inventors have investigated whether dTERT-specific T-cell responses could be enhanced in PBMCs incubated with either rcGM-CSF and rcIL-4 for 24 hours, or with hFlt3 ligand followed by maturation stimuli (rcIL1β, rcTNFα and IL-7) and peptides stimulation for another 24 hours and 11 or 18 days of in vitro cell expansion. This technique was described by Mallone and colleagues for human PBMCs and is called in vitro immunization (Martinuzzi et al. 2011). The principle of this experiment is exposed in FIG. 8. To stimulate specific T cells, 15 mer overlapping peptides recovering one third of the dog TERT protein (FIG. 3) were used in pools containing 17 to 18 peptides each.

Eleven or 18 days after the beginning of culture, cells were subsequently transferred into dog IFN-γ ELISPOT plates for 24 hours with 5 µg/mL of each pool of peptides. The inventors have noticed a threefold increase in the frequency of dTERT specific IFN-γ secreting T cells with pool 2/rcGMCSF+rcIL-4 and a twofold increase with pool 4/FlT-3 L after 11 days of culture in comparison with medium stimulated PBMCs (FIG. 9A). Moreover, a fourfold increase in the frequency of dTERT specific IFN-γ secreting T cells was observed after 18 days of culture with pool 4/Flt-3 L in comparison with PBMCs stimulated with culture medium (FIG. 9B).

These results demonstrate the existence of a naturally occurring repertoire of dog TERT specific IFN-γ secreting T-cell repertoire in peripheral blood of naïve experimentation dog.

Example 5: In Vivo Specific Cellular Immune Response in Dogs Vaccinated with pDUV5

Six naïve beagle dogs received a local anaesthetic of 2.5 mg/kg IV imalgene and 20-80 µg/kg IV dorbene 15-20 minutes before vaccination and 100-400 µg/kg IM post vaccination. The dogs were injected intradermally with 400 µg of pDUV5 DNA followed by electroporation. pDU5 DNA was electroporated at days 0, 29, 57 and 142. Peripheral blood was drawn and mononuclear cells tested for dog telomerase specific peptides belonging either to pool 6 or pool 19 according to the method of Martinuzzi et al., 2011.

FIGS. 10A and 10B show that IFNγ specific T cell responses were detected. As shown on FIGS. 11A and 11B, pDUV5 DNA vaccination at days 57 and 142 show classical long term memory responses, that is rising sharply and decaying more slowly.

Example 6: Specific dTERT T Cell Responses in Animals with Neoplasias

To show that pDUV5 DNA electroporation can induce specific dTERT T cell responses in animals with neoplasias, five pet dogs with neoplasias and three pet dogs as controls were used. The diseased animals presented with widely different tumours. See Table 2 below.

TABLE 2

Data for healthy and tumor bearing dogs:

| Name of dog | Dog breed | Age (years) | Sex | Pathology |
|---|---|---|---|---|
| Belka | Boxer | 7 | F | Healthy |
| Choupette | Jack Russel | 5 | F | Healthy |
| Tequila | Rottweiler | 9 | F | Healthy |
| Bambou | Labrador | 8 | F | Mastocytoma grade II |
| Lambert | Labrador | 12 | M | Tumor Hypothesis (liver/right adrenal) |
| Maury | Bernese Mountain dog | 9 | M | Neoplastic process + lung metastasis |
| Semelaigne | Cavalier King Charles | 10 | F | Bone tumor |
| Fidji | Shetland sheepdog | 2.5 | M | Histiocytoma |

Peripheral blood was drawn and the in vitro stimulation protocol as described in Example 4 and in Martinuzzi et al., 2011, was performed, using pool 4 peptides.

As can be seen in FIG. 12, specific peptide responses well over medium controls were identified for all animals. This means that the immunological repertoire is not depleted, biased or suppressed by the neoplasias. The latter finding is particularly important for it shows that even if there was some degree of immunosuppression or excessive Treg induction in diseased dogs, the vaccination of the invention is nonetheless capable of inducing T cell responses.

REFERENCES

Adolph, K. 1996 ed. "Viral Genome Methods" CRC Press, Florida de Fornel P, Delisle F, Devauchelle P, Rosenberg D. 2007. Effects of radiotherapy on pituitary corticotroph macrotumors in dogs: a retrospective study of 12 cases. Can Vet J 48: 481-486.

Dillman R O. 2011. Cancer Immunotherapy. Cancer Biotherapy and Radiopharmaceuticals 26: 1-64.

Disis M L, Bernhard H, Jaffee E M. 2009. Use of tumour-responsive T cells as cancer treatment. Lancet 373: 673-683.

Finn O J. 2008. Cancer immunology. N Engl J Med 358: 2704-2715.

Fridman W H, Pages F, Sautes-Fridman C, Galon J. 2012. The immune contexture in human tumours: impact on clinical outcome. Nat Rev Cancer 12: 298-306.

Gentilini F. 2010. "Masitinib" is safe and effective for the treatment of canine mast cell tumors. J Vet Intern Med 24: 6; author reply 7.

Hanahan D, Weinberg R A. 2011. Hallmarks of cancer: the next generation. Cell 144: 646-674.

Jourdier T M, Moste C, Bonnet M C, Delisle F, Tafani J P, Devauchelle P, Tartaglia J, Moingeon P. 2003. Local immunotherapy of spontaneous feline fibrosarcomas using recombinant poxviruses expressing interleukin 2 (IL2). Gene Therapy 10: 2126-2132.

Manley C A, Leibman N F, Wolchok J D, Riviere I C, Bartido S, Craft D M, Bergman P J. 2011. Xenogeneic murine tyrosinase DNA vaccine for malignant melanoma of the digit of dogs. J Vet Intern Med 25: 94-99.

Marconato L. 2011. The staging and treatment of multicentric high-grade lymphoma in dogs: a review of recent developments and future prospects. Vet J 188: 34-38.

Martinez P, Blasco M A. 2011. Telomeric and extra-telomeric roles for telomerase and the telomere-binding proteins. Nature Reviews Cancer 11: 161-176.

Martinuzzi E, et al. 2011. acDCs enhance human antigen-specific T-cell responses. Blood 118: 2128-2137.

Merlo D F, et al. 2008. Cancer incidence in pet dogs: findings of the Animal Tumor Registry of Genoa, Italy. J Vet Intern Med 22: 976-984.

Mir L M. 2008. Application of electroporation gene therapy: past, current, and future. Methods Mol Biol 423: 3-17.

Murray, 1991, ed. "Gene Transfer and Expression Protocols" Humana Pres, Clifton, N.J.

Sardesai N Y, Weiner D B. 2011. Electroporation delivery of DNA vaccines: prospects for success. Curr Opin Immunol 23: 421-429.

Topalian S L, Weiner G J, Pardoll D M. 2011. Cancer Immunotherapy Comes of Age. Journal of Clinical Oncology 29: 4828-4836.

Vascellari M, Baioni E, Ru G, Carminato A, Mutinelli F. 2009 Animal tumour registry of two provinces in northern Italy: incidence of spontaneous tumours in dogs and cats. BMC Vet Res 5: 39.

Yang, 1992, "Gene transfer into mammalian somatic cells in vivo", Crit. Rev. Biotech. 12: 335-356

Yang Y, Chen Y, Zhang C, Huang H, Weissman S M. 2002. Nucleolar localization of hTERT protein is associated with telomerase function. Exp Cell Res 277: 201-209.

Yazawa M, et al, 2003, J. Vet. Med. Sci 65(5):573-577

---

The invention claimed is:

1. A nucleic acid molecule that comprises a sequence encoding a fusion protein which comprises at least 80% of the amino acid sequence of a full length wild-type dog telomerase reverse transcriptase (TERT), wherein said protein (i) does not contain amino acids VDD within the TERT catalytic site, (ii) does not contain a nucleolar localization signal sequence, and (iii) comprises an amino acid sequence which enhances the addressing of said TERT to a proteasome.

2. The nucleic acid molecule of claim 1, wherein the fusion protein further comprises a non-dog TERT antigenic fragment.

3. The nucleic acid of claim 1, wherein said nucleic acid is a DNA plasmid.

4. The nucleic acid molecule of claim 1, wherein the amino acid sequence which enhances the addressing of TERT to the proteasome is a sequence of ubiquitin.

5. The nucleic acid molecule of claim 1, wherein the amino acid sequence which enhances the addressing of TERT to the proteasome is a sequence of calreticulin.

6. The nucleic acid molecule of claim 1, wherein the nucleolar localization signal sequence consists of 47 N-terminal amino acids of the full-length wild-type dog TERT.

7. The nucleic acid molecule of claim 1, herein the amino acid sequence of the fusion protein consists of SEQ ID NO: 2.

8. The nucleic acid molecule of claim 2, wherein the non-dog TERT antigenic fragment originates from a cat TERT sequence.

9. An immunogenic composition comprising:
(a) the nucleic acid molecule of claim 1, and
(b) a carrier and/or excipient.

10. A nucleic acid molecule comprising a sequence that encodes a protein which comprises (i) the amino acid sequence of a mutant dog telomerase reverse transcriptase (TERT) consisting of SEQ ID NO: 6 and optionally (ii) an amino acid sequence which enhances the addressing of said mutant TERT to a proteasome.

11. The nucleic acid molecule of claim 10 comprising nucleotides 241-3459 of SEQ ID NO: 1.

12. The nucleic acid molecule of claim 10, wherein the amino acid sequence which enhances the addressing of the TERT to the proteasome is a sequence of ubiquitin.

13. The nucleic acid molecule of claim 10, wherein the amino acid sequence which enhances the addressing of the TERT to the proteasome is a sequence of calreticulin.

14. The nucleic acid molecule of claim 10, wherein said nucleic acid molecule is a DNA plasmid.

15. An immunogenic composition comprising:
(a) the nucleic acid molecule of claim 10, and
(b) a carrier and/or excipient.

16. A method for triggering an immune response in a dog, against cells that overexpress telomerase, wherein the method comprises administering to the dog an effective amount of the immunogenic composition of claim 9.

17. The method of claim 16, wherein said cells that overexpress telomerase are dysplasia cells or tumor cells.

18. A method for preventing or treating a tumor in a dog, which method comprises administering to the dog an effective amount of the immunogenic composition of claim 9.

19. The method of claim 18, wherein the tumor is selected from the group consisting of bladder cancer, brain tumors, mammary tumors, mast cell tumors, malignant histiocytosis, histocytic sarcomas, squamous cell carcinomas, hemangiosarcoma, lymphomas, melanoma, osteosarcoma, and testicular tumors.

20. The method of claim 16, wherein the composition is administered by intradermal or intramuscular route.

21. The method of claim 16, wherein the composition is administered by electroporation.

22. The method of claim 16, wherein the dog is at risk of developing a tumor.

23. The method of claim 16, wherein the dog is healthy.

24. The method of claim 16, wherein the effective amount of the composition induces a long term memory immune response in the dog.

25. The method of claim 23, wherein the dog is 10 years of age or more.

26. A method for triggering an immune response in a dog, against cells that overexpress telomerase, wherein the method comprises administering to the dog an effective amount of the immunogenic composition of claim 15.

27. The method of claim 26, wherein said cells that overexpress telomerase are dysplasia cells or tumor cells.

28. The method of claim 26, wherein the nucleic acid molecule is administered by intradermal or intramuscular route.

29. The method of claim 26, wherein the nucleic acid molecule is administered by electroporation.

30. The method of claim 26, wherein the dog is at risk of developing a tumor.

31. The method of claim 26, wherein the dog is healthy.

32. The method of claim 26, wherein the effective amount of the composition induces a long term memory immune response in the dog.

33. The method of claim 31, wherein the dog is 10 years of age or more.

34. A method for preventing or treating a tumor in a dog, which method comprises administering to the dog an effective amount of the immunogenic composition of claim 15.

35. The method of claim 34, wherein the tumor is selected from the group consisting of bladder cancer, brain tumors, mammary tumors, mast cell tumors, malignant histiocytosis, histocytic sarcomas, squamous cell carcinomas, hemangiosarcoma, lymphomas, melanoma, osteosarcoma, and testicular tumors.

* * * * *